United States Patent [19]
Hogness et al.

[11] Patent Number: 5,514,578
[45] Date of Patent: May 7, 1996

[54] POLYNUCLEOTIDES ENCODING INSECT STEROID HORMONE RECEPTOR POLYPEPTIDES AND CELLS TRANSFORMED WITH SAME

[75] Inventors: David S. Hogness, Stanford; Michael R. Koelle, Menlo Park; William A. Segraves, San Diego, all of Calif.

[73] Assignee: The Board of Trustees of Leland Stanford University, Stanford, Calif.

[21] Appl. No.: 954,937

[22] Filed: Sep. 30, 1992

Related U.S. Application Data

[63] Continuation of Ser. No. 485,749, Feb. 26, 1990, abandoned.
[51] Int. Cl.$^6$ .............................. C12N 5/00; C12N 1/20; C07H 21/04
[52] U.S. Cl. .................................. 435/240.2; 435/252.3; 536/23.5
[58] Field of Search .................................. 536/23.1, 23.5; 935/9, 33, 34; 435/69.1, 172.3, 320.1, 240.2

[56] References Cited

U.S. PATENT DOCUMENTS 4,704,362 11/1987 Itakura et al. ........................... 435/253
4,818,684 4/1989 Edelman et al. ........................... 435/7

FOREIGN PATENT DOCUMENTS

WO90/06364 6/1990 WIPO.

OTHER PUBLICATIONS

Ashburner et al. (1974) *Cold Spring Harbor Symp. Quant. Biol.,* 38:655–662. The Temporal Control of Puffing Activity in Polytene Chromosomes.
Evans (1988) *Science* 240:889–895 The Steroid and Thyroid Hormone Receptor Superfamily.
Green and Chambon (1988) *Trends in Genetics* 4:309–314 Nuclear Receptors Enhance Our Understanding of Transcription Regulation.
Segraves (1988) Ph.D. Thesis, Stanford University Molecular and Genetic Analysis of the E75 Ecdysone–Responsive Gene of *Drosophila melanogaster.*
Krust et al. (1986) *EMBO J.* 5:891–897 The chicken oestrogen receptor sequence: homology with v–erbA and the human oestrogen and glucocorticoid receptors.
M. Kanehisa (1984) *Nucleic Acids Res.* 12:203–213 Use of statistical criteria for screening potential homologies in nucleic acid sequences.
Hershko and Ciechanover (1982) *Ann. Rev. Bioch.* 51:335–364 Mechanisms of Intracellular Protein Breakdown.
Miller et al. (1985) *EMBO J.* 4:1609–1614 Receptor zinc–binding domains in the protein transcription factor IIIA from Xenopus oocytes.
Freedman et al. (1988) *Nature* 334:543–546 The function and structure of the metal coordination sites within the glucocorticoid receptor DNA binding domain.

Severne et al. (1988) *EMBO J.* 9:2503–2508 Metal binding "finger" structures in the glucocorticoid receptor defined by site–directed mutagenesis.
Giguere et al. (1986) *Cell* 46:645–652 Functional Domains of the Human Glucocorticoid Receptor.
Danielson et al. (1987) *Mol. Endocrinol.* 1:816–822 Domains of the Glucocorticoid Receptor Involved in Specific and Nonspecific Deoxyribonucleic Acid Binding, Hormone Activation, and Transcriptional Enhancement.
Rusconi et al. (1987) *EMBO J.* 6:1309–1315 Functional dissection of the hormone and DNA binding activities of the glucocorticoid receptor.
Mader et al. (1989) *Nature* 338:271–274 Three amino acids of the oestrogen receptor are essential to its ability to distinguish an oestrogen from a glucocorticoid–responsive element.
Umesono and Evans (1989) *Cell* 57:1139–46 Determinants of Target Gene Specificity for Steroid/Thyroid Hormone Receptors.
Umesono et al (1988) *Nature* 336:262–265 Retinoic acid and thyroid hormone induce gene expression through a common responsive element.
Kumar and Chambon (1988) *Cell* 55:145–156 The Estrogen Receptor Binds Tightly to Its Responsive Element as a Ligand–Induced Homodimer.
Guiochon et al. (1989) *Cell* 57:1147–1154 Mechanisms of Nuclear Localization of the Progesterone Receptor: Evidence for Interaction between Monomers.
Picard and Yamamoto (1987) *EMBO J.* 6:3333–3340 Two signals mediate hormone–dependent nuclear localization of the glucocorticoid receptor.
Pratt et al. (1988) *J. Biol. Chem.* 263:267–273 A Region in the Steroid Binding Domain Determines Formation of the Non–DNA–Binding, 9 S Glucocorticoid Receptor Complex.
Nauber et al. (1988) *Nature* 336:489–492 Abdominal segmentation of the Drosophila embryo requires a hormone receptor–like protein encoded by the gap gene knirps.
Oro et al. (1988) *Nature* 336:493–496 The Drosophila gene knirps–related is a member of the steroid–receptor gene superfamily.
Rothe et al. (1989) *EMBO J.* 8:3097–3094 Three hormone receptor–like Drosophila genes encode an identical DNA–b- inding finger.
Petkovich et al. (1987) *Nature* 330:444–450 A human retinoic acid receptor which belongs to the family of nuclear receptors.
Dieckmann and Tzagaloff (1985) *J. Biol. Chem.* 260:1513–1520 Assembly of the Mitochondrial Membrane System.
Riddihough and Pelham (1987) *EMBO J.* 6:3729–3734 An ecdysone response element in the Drosophila hsp27 promoter.

(List continued on next page.)

Primary Examiner—Jacqueline M. Stone
Assistant Examiner—Deborah Crouch
Attorney, Agent, or Firm—Townsend and Townsend and Crew

[57] ABSTRACT

Polynucleotide sequences which encode ecdysone receptors have been isolated and expressed in host cells.

8 Claims, 6 Drawing Sheets

OTHER PUBLICATIONS

Strangmann–Diekmann et al. (1990) *Eur. J. Biochem.* 189:137–143. Affinity Labeling of Partially Purified Ecdysteroid Receptor with Bromoacetylated 20–OH–ecdysone Derivative.

Lehmann et al. (1988) *Molecular and Cellular Endocrinology* 57:239–249 Ecdysteroid Receptors of the blowfly.

Poole et al. (1985) *Cell* 40:37–40 The engrailed Locus of Drosophila: Structural Analysis of an Embryonic Transcript.

Feigl et al. (1989) *Nucleic Acids Research* 17(18):7167–7178 A member of the steroid hormone receptor gene family is expressed in the 20–OH–ecdysone inducible puff 75B in *Drosophila melanogaster*.

Ronald M. Evans (1988) *Science* 240:889–895 The Steroid and Thyroid Hormone Receptor Superfamily.

Bidmon and Koolman (1989) *Experientia* 45:106–109 Ecdysteroid receptors located in the central nervous system of an insect.

Meyerowitz and Hogness (1982) *Cell* 28:165–176 Molecular Organization of a Drosophila Puff Site That Responds to Ecdysone.

Lehmann et al (1988) Molec. & Cell. Endocrinol. Ecdysteroid receptors of the blowfly, 57, 239–249.

Suggs et al (1981) Proced. Nat. Acad. Sci. 78, 6613–6617.

Reeck et al. (1987) Cell 50, 667.

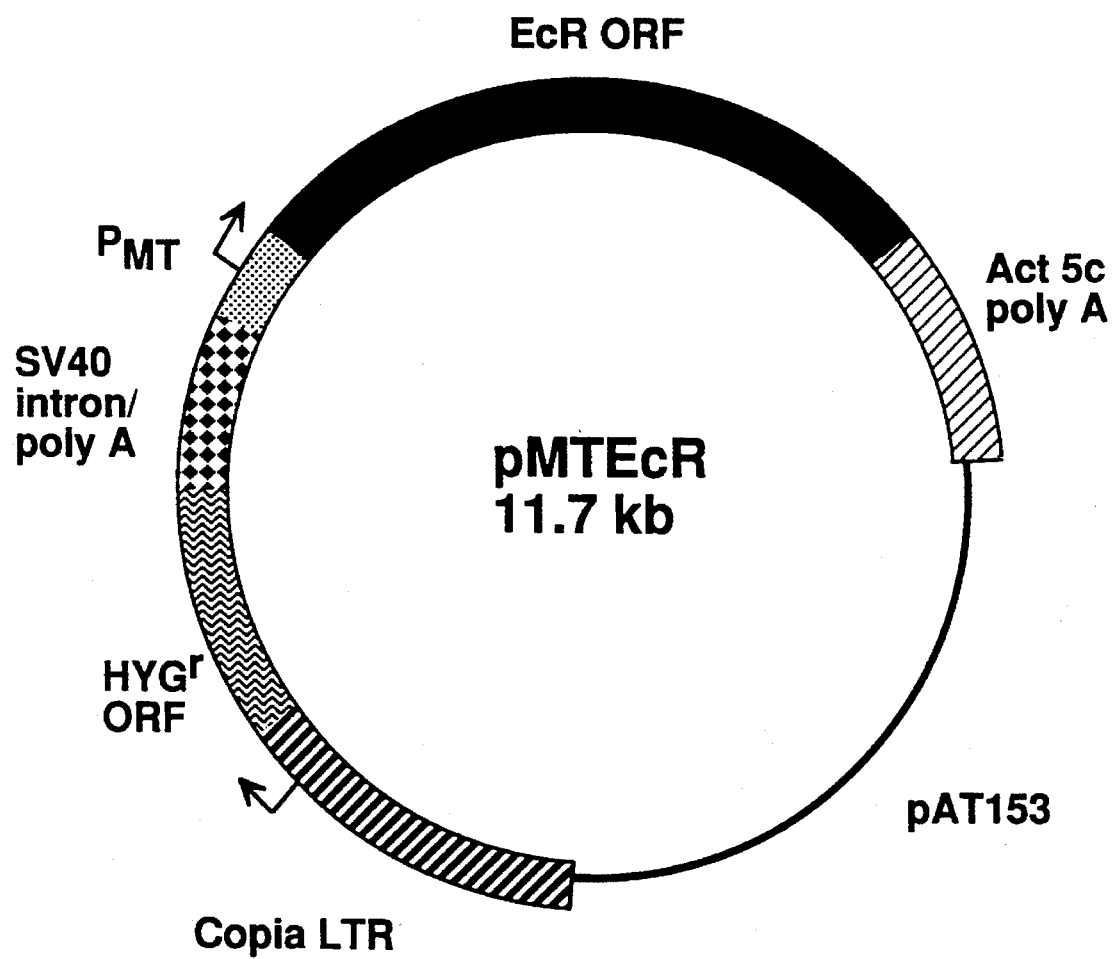

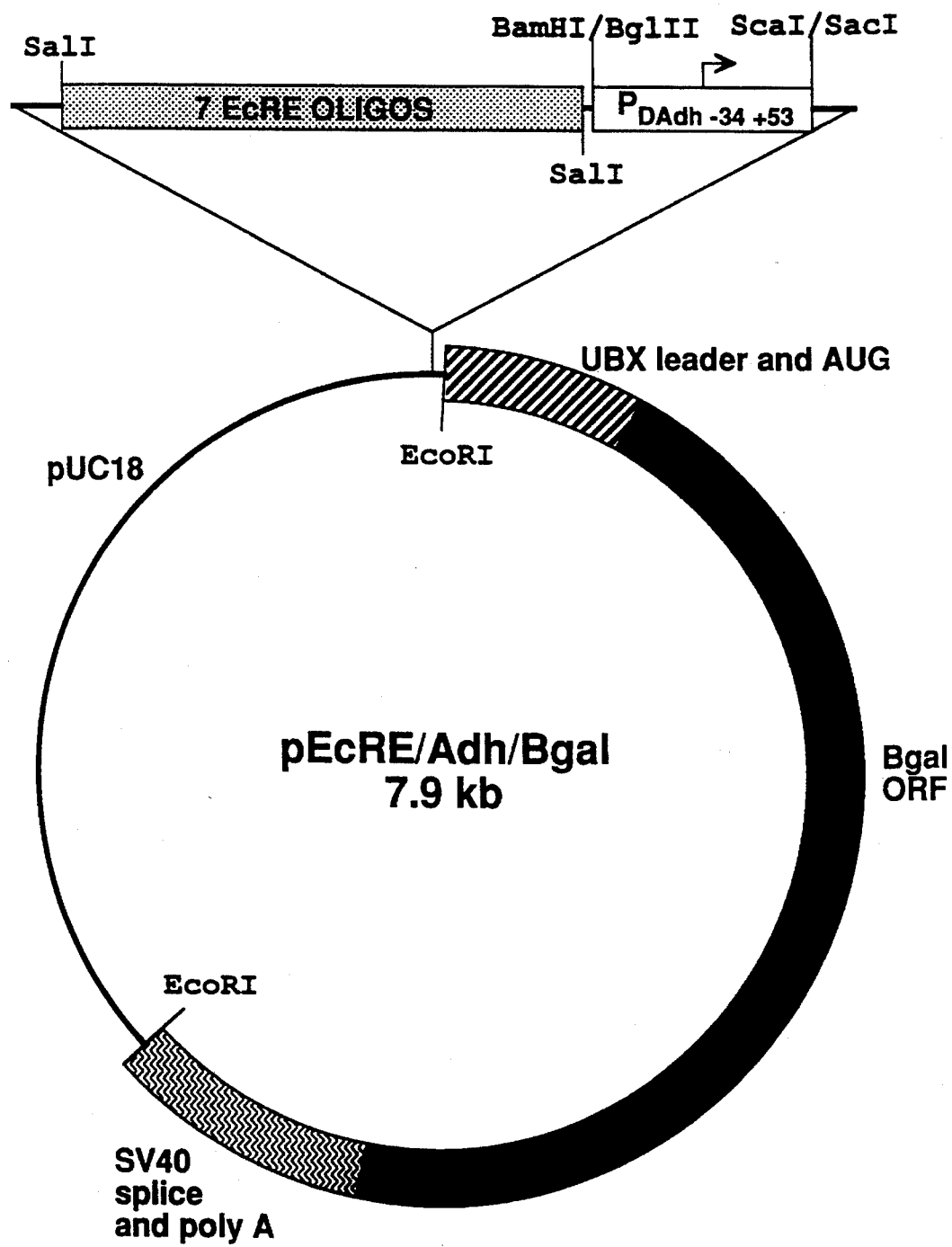

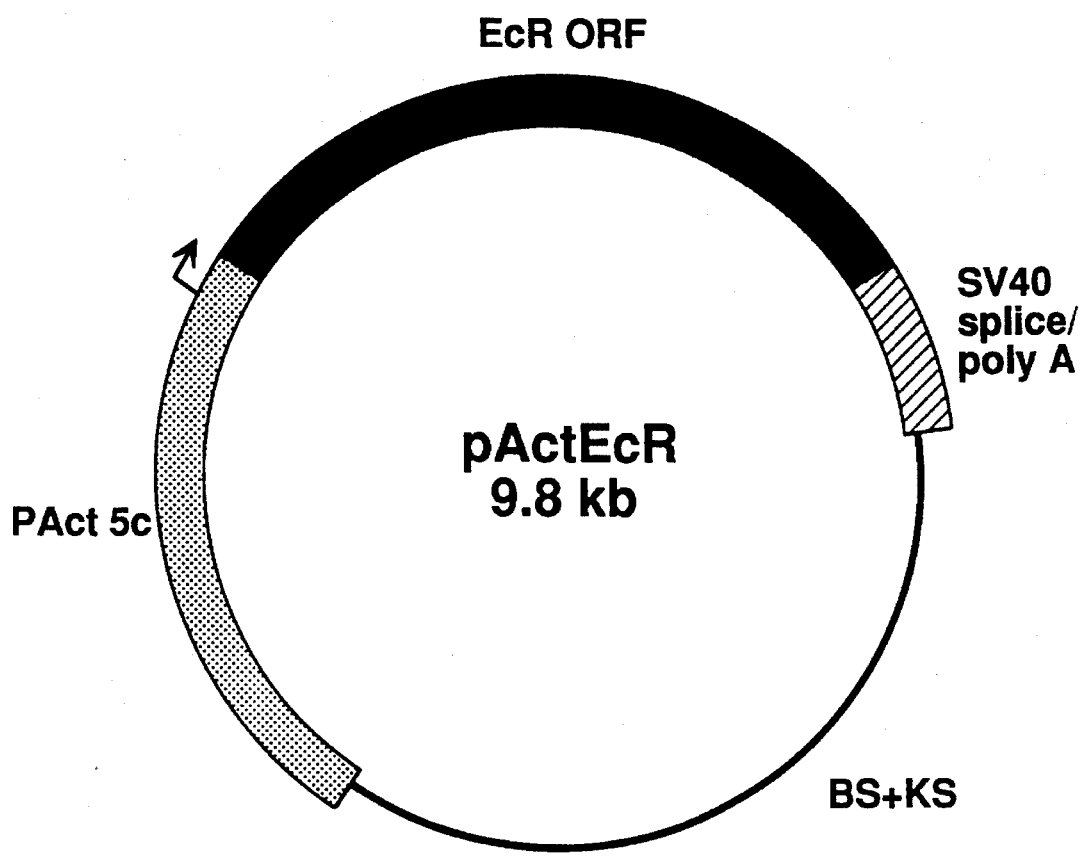

```
   1 GAATTCGGCAAATACAGCACACAATTGAAACGACAACCTAACATTTCAAAACGAAAACCCCAAATAAGTTGTAACCAAATAAGTTTAAATCAC
 125 ATATACACTTACATATATTAAGAAAAATTGTTAGACAACAATCCCAATAACCGCAACACCGCAATCATCGGCAAAATCATCGCAAAATGCAAATGCA
 249 TTGTAGCTGAAACTCAAACAATAGTAAAATACATAAATAGTGGTGAAGAAGCAAAAGAAAATAGTTCTTAAAATAACGAATCGAGACATATTCATATTGTACAGATATTATGCC
 373 GGCTGCATAGTGCAAACTGCGGCTGAGGGATACAGCGTGAGGGAATACAACGCGTATCGGAACGCTGAGGGAATACAGCGTGAGGTGAATACAGCGTGAGGGAATACAAGCTCAGCGTGAGATAGACGCCGTCT
 497 AGTCGTGGTCTGTGAACGCTAGCTCCCGCTTTGCCAGGACGAGACTTTTCCGCATCCAAATATGTGCTTTGTCAATAATGTGCTTGTCAACTGGAATACGCCGAGTGAGTGAGGGATTGTGCCGTG
 621 GATCCCGATCCCTTACATAGTATATAAGGTAGTGAAAGATTTTACTGAAAGATTTTACTGAACTGGAATGGAATACGCCAGTGGGCCCATGGATACTTGTCGA (gtgagt···v···ttacag)
 745 TTAGTAGCGAACTGGCACTATATCGACGCATATGCTCTGATTGTTCCCGACTAAATGAGCAGGATTCGGGCGAAAATGTATTTGAACGCAAACAAGTCGCAAAAATACTAGTCC
 869 ACCACGAAACTGCACAAAACACCGCCAGACGAGCAGAACCTCGGGCCGCACGACCGAGCTTCGTAAAGCAACAGAGGATCTTACCAGGAGATAGCTCTCCACATAGACCAACTGCCAGG
 993 GACAAGCTCCTTGTCCCAGCCGACGCTAGTGAACGGAAAACGCCACAAAACGGGCACTATCGGCTGCCAGAGG ATG CGG TCG AAC AAC GGC GGC TTC ATG
                                                                              Met Lys Arg Trp Ser Asn Asn Gly Gly Phe Met    12

1105 CGC CTA CCG GAG GAG TCG TCC GAG GTC ACG TCC TCG AAC GGG CTC GTC CTG CCC TCG ATG AAC ATG TCG CCC TCG GAC
     Arg Leu Pro Glu Glu Ser Ser Glu Val Thr Ser Ser Asn Gly Leu Val Leu Pro Ser Met Asn Met Ser Pro Ser Leu Asp    43

1198 TCG CAC GAC TAT TGC GAT CAG GAC CTT CTC TGG CTC TGC GGT TCG TTT GGC TCC AAC GAG CAT GGC CTA AGT CAG CAG CAG
     Ser His Asp Tyr Cys Asp Gln Asp Leu Leu Trp Leu Cys Gly Ser Phe Gly Ser Asn Glu His Gly Leu Ser Gln Gln Gln    74

1291 CAG AGC GTC ATC ACG CTG GCC ATG CAC GGG TGC TCC AGC ACT CTG CCC GCG ATC ATT CCG ATC AAC GGC AAC GCG AAT GGG AAT
     Gln Ser Val Ile Thr Leu Ala Met His Gly Cys Ser Ser Thr Leu Pro Ala Ile Ile Pro Ile Asn Gly Asn Ala Asn Gly Asn    105

1384 GGA GGC TCC ACC AAT CAG GCC CAA TAT GTG CCG GGT GCC ACT AAT CTG GGA GCG TTG GCC ATG GGG CTC AAC GGC TTC AAT GGA ATG CAG
     Gly Gly Ser Thr Asn Gly Gly Gln Tyr Val Pro Gly Ala Thr Asn Leu Gly Ala Leu Ala Met Gly Gly Phe Asn Gly Met Gln    136

1477 CAA CAG ATT CAG AAT GGC CAC CAC GGT ATT CTT CAT CAC CAC CTT CAG CAG CAG CTG GGG GGC GCG
     Gln Gln Ile Gln Asn Gly His His Gly Ile Leu His His His His Leu Gln Gln Gln Leu Gly Gly Ala    167

1570 GGC GGC GGT GGT ATC GGT GGA ATG GGT ATT CTT CAC CAC CAC GCG AAT GGC ACC CCA AAT GGC GTT ATC GGA GTT GTG GGC GGC GGC GTA
     Gly Gly Gly Gly Ile Gly Gly Met Gly Ile Leu His His His Ala Asn Gly Thr Pro Asn Gly Val Ile Gly Val Val Gly Gly Gly Val    198

1663 GGT CTT GGA GTA GGC GGA GGC GGA GTG GGA GGC CTG GGA GTG GGA ATG CAG CAC ACA CCC CGA AGC CAG ATG TCG GTG AAT TCT ATA TCT TCA GGT CGC GAT
     Gly Leu Gly Val Gly Gly Gly Gly Val Gly Gly Leu Gly Val Gly Met Gln His Thr Pro Arg Ser Gln Met Ser Val Asn Ser Ile Ser Ser Gly Arg Asp    229
```

Fig. 4A

```
1756  GAT CTC TCG CCT TCG AGC AGC TTG AAC GGA TAC TCG GCG AAC GAA AGC TGC GAT GCG AAG AAG AGC AAG CCT GCG CCA CGG GTG CAA  260
      Asp Leu Ser Pro Ser Ser Ser Leu Asn Gly Tyr Ser Ala Asn Glu Ser Cys Asp Ala Lys Lys Ser Lys Pro Ala Pro Arg Val Gln

1849  GAG GAG CTG TGC GTT GTG TGC GAC AGG CGC TCC GGC TAC CAC AAC GCC CTC ACC TGT GAG GGC TGC AAG GGG TTC TTT CGA CGC AGC  291
      Glu Glu Leu Cys Val Cys Gly Asp Arg Arg Ser Gly Tyr His Asn Ala Leu Thr Cys Glu Gly Cys Lys Gly Phe Phe Arg Arg Ser

1942  GTT ACG AAG AGC GCC GTC TAC TGC TGC AAG TTC GGG CGC TGC GAA ATG GAC ATG TAC ATG AGG CGA AAG CGA AAG TGT CAG GAG CTG CGC CTG AAA  322
      Val Thr Lys Ser Ala Val Tyr Cys Cys Lys Phe Gly Arg Cys Glu Met Asp Met Tyr Met Arg Arg Lys Arg Lys Cys Arg Leu Lys

2035  AAG TGC CTG GCC GTG GGT ATG GGC GAA TGC CGG CCG GTC GTC CCG GAG AAC CAA TGT GCG ATG AAG CGG AAG GCC CAG AAG GAG AAG  353
      Lys Cys Leu Ala Val Gly Met Gly Glu Cys Arg Pro Val Val Pro Glu Asn Gln Cys Ala Met Lys Arg Lys Ala Gln Lys Glu Lys

2128  GAC AAA ATG ACC ACT TCG CCG AGC TCT CAG CAT GGC AAT GGC TTG GCC TCT GGT GGC GGC CAA GAC TTT GTT AAG AAG GAG ATT CTT  384
      Asp Lys Met Thr Thr Ser Pro Ser Ser Gln His Gly Asn Gly Ser Leu Ala Ser Gly Gly Gln Asp Phe Val Lys Lys Glu Ile Leu

2221  GAC CTT ATG ACA TGC GAG CCG CCC CAG CAT GCC ACT ATT CCG CTA CTA CCT GAT GAA ATA TTG GCC AAG TGT CAA GCG CGC AAT ATA CCT TCC  415
      Asp Leu Met Thr Cys Glu Pro Pro Gln His Ala Thr Ile Pro Leu Leu Pro Asp Glu Ile Leu Ala Lys Cys Gln Ala Arg Asn Ile Pro Ser
                                                            (gtaggg..v..gtacag)                                    (gtgggt..v..ttgcag)

2314  TTA ACG TAC AAT CAG TTG GCC GTT ATA TAC AAG TTA ATT TGG TAC CAG GAT GGC TAT GAG GAT GGC TCT GAA GAG CAG GAT CTC AGG CGT ATA ATG  446
      Leu Thr Tyr Asn Gln Leu Ala Val Ile Tyr Lys Ile Ile Trp Tyr Gln Asp Gly Tyr Glu Gln Pro Ser Glu Glu Arg Leu Arg Ile Met

2407  AGT CAA CCC GAT GAG AAC GAG ACG GCC AGC GTC CAT ATA ACC GAG ATA ACC ATA CTC ACG GTC CAG TTG ATT GTT GAG TTT  477
      Ser Gln Pro Asp Glu Asn Glu Thr Ala Ser Val His Ile Thr Glu Ile Thr Ile Leu Thr Val Gln Leu Ile Val Glu Phe
                                     (gtgagt..v..cgttag)

2500  GCT AAA GGT CTA CCA GCG TTT ACA AAG ATA CCC CAG GAG GAC CAG ATC ACG TTA CTA AAG GCC TGC TCG GAG GTG ATG ATG CTG CGT ATG  508
      Ala Lys Gly Leu Pro Ala Phe Thr Lys Ile Pro Gln Glu Asp Gln Ile Thr Leu Leu Lys Ala Cys Ser Ser Glu Val Met Met Leu Arg Met

2593  GCA CGA CGC TAT GAC CAC CAC TCG GAC TCA ATA TTC TTC GCG AAT AAT AGA TCA TAT ACG CGG GAT TCT TAC AAA ATG GCC GGA ATG GCT GAT  539
      Ala Arg Arg Tyr Asp His His Ser Asp Ser Ile Phe Phe Ala Asn Asn Arg Ser Tyr Thr Arg Asp Ser Tyr Lys Met Ala Gly Met Ala Asp

2686  AAC ATT GAA GAC CTG CAT TTC TGC CGC CAA ATG TTC TCG ATG AAG GTG GAC AAC GTC GAA TAC GCG CTT CTC ACT GCC ATT GTG ATC TTC  570
      Asn Ile Glu Asp Leu His Phe Cys Arg Gln Met Phe Ser Met Lys Val Asp Asn Val Glu Tyr Ala Leu Leu Thr Ala Ile Val Ile Phe
```

Fig. 4B

```
2779  TCG GAC CGG CCG GGC CTG GAG AAG GCC CAA CTA GTC GAA GCG ATC CAG AGC TAC ATC GAC ACG CTA ATT TAT ATA CTC AAC CGC CAC   601
      Ser Asp Arg Pro Gly Leu Glu Lys Ala Gln Leu Val Glu Ala Ile Gln Ser Tyr Ile Asp Thr Leu Ile Tyr Ile Leu Asn Arg His

2872  TGC GGC GAC TCA AAG AGC CTC GTC TTC GCA AAG CTG CTC TCG ATC CTC ACC GAG CTG CGT ACG CTG GGC AAC CAG AAC GCC GAG TGT   632
      Cys Gly Asp Ser Met Ser Leu Val Phe Ala Lys Leu Leu Ser Ile Leu Thr Glu Leu Arg Thr Leu Gly Asn Gln Asn Ala Glu Met Cys

2965  TTC TCA AAG CTC AAA AAC CGC AAG TTC CTC GAG GAG ATC TGG GAC GTT CAT GCC ATC CCG CCA GTC CAG TCG CAC CTT   663
      Phe Ser Leu Lys Asn Arg Lys Phe Leu Glu Glu Ile Trp Asp Val His Ala Ile Pro Pro Val Gln Ser His Leu

3058  CAG ATT ACC CAG GAG AAC CGT GAG ATG CGG GCA TCG GTT GGG GGC GCC ATT ACC GCC GGC ATT GAT TGC GAC   694
      Gln Ile Thr Gln Glu Asn Arg Glu Met Arg Ala Ser Val Gly Gly Ala Ile Thr Ala Gly Ile Asp Cys Asp

3151  TCT GCC TCC ACT TCG GCG GCG GCA GCC GCC GCG CAT CAG CCT CAG CCC CAA CCC TCC CTG ACC CTG TCC TCC CAG AAC GAT TCC   725
      Ser Ala Ser Thr Ser Ala Ala Ala Ala Ala His Gln Pro Gln Pro Gln Pro Ser Leu Thr Leu Ser Ser Gln Asn Asp Ser

3244  CAG CAC CAG ACA CAG CCG CAG CTA CAA CCT CAG GGT CAA CTG CAA CCA CAG CTC CAA CAG CTT CAG ACG CAA   756
      Gln His Gln Thr Gln Pro Gln Leu Gln Pro Gln Gly Gln Leu Gln Pro Gln Leu Gln Gln Leu Gln Thr Gln

3337  CTC CAG CCA CAG ATT CAA CAG CCA CAG CTC CTC CTT CCC GCT CCC GTG CCC GCC TCC GTA ACC GCA CCT GGT TCC TTG GCG GTC   787
      Leu Gln Pro Gln Ile Gln Gln Pro Gln Leu Leu Leu Pro Ala Pro Val Pro Ala Ser Val Thr Ala Pro Gly Ser Leu Ala Val

3430  AGT ACG AGC AGC GAA TAC ATG GGC GGA AGT GCG GCC ATA GGA CCC GCA ACC ACC AGT ATC ACG GCT ACC GTT ACC GCT AGC   818
      Ser Thr Ser Ser Glu Tyr Met Gly Gly Ser Ala Ala Ile Gly Pro Ala Thr Thr Ser Ile Thr Ala Thr Val Thr Ala Ser

3523  TCC ACC ACA TCA GCG GTA CCG ATG GGC AAC GGA GTT GGA GTC GGT GTG GGC AAC GTC AGC ATG TAT GCG AAC GCC CAG ACG GCG   849
      Ser Thr Thr Ser Ala Val Pro Met Gly Asn Gly Val Gly Val Gly Val Gly Gly Asn Val Ser Met Tyr Ala Asn Ala Gln Thr Ala

3616  ATG GCC TTG ATG GGT GTA GCC CAT TCG CAC CAA GAG CAG CTT ATC GGG GGA GTG GCG GTT AAG TCG GAG CAC TCG ACT GCA TAG CAG   878
      Met Ala Leu Met Gly Val Ala His Ser His Gln Glu Gln Leu Ile Gly Gly Val Ala Val Lys Ser Glu His Ser Thr Ala   -

3709  GCGCAGAGTCAGCTCGACATCGACGTCCTGCTGAGTAGAAAGCCAGCTGAACCACACAGACATAGGGAAGTTCTCTCCAGAGAGTTCGACCGA
3833  ACTAAATAGTAAAAGTGAATAACTAGTGGACAAGCGTAAAATGCAGTTATTAGTCTTAAGCTGCAAATATTACCTATTATTCATACAAATTAACAGCCTATTAACATTACG
3957  CTAAAGCTTAATTGAATAAAGCTTCAACAACAATTGGACAAGCGGTTGAGGAACCGGAGAAATTTAGAAAAAAGATCATTGAAACAGATACAGAATTATGAAGATTATCATTTTTTGGGTGGA
4081  TGTATGTCGCATCAGATCTGTTTATATTTAAAAATAAATATAAAAAAATATAAAAAAATATATATAAAATCTAAACGTAAACAACAGATCCGAAACAATCCTCCAAACTGCAATGTCAAACATAAGAATGAGAACAGAGCACGACTAGGCGTGAACAGAGCAGGGAAGAGAGA
4205  AGAGAATAAGATTGTTTATATTTAAAAATAAATATAAAAATAATACTACTCTAAACGTAATGAAAGCAACTGTATATATCTAACTATAACGAATCTATATCTATTAACCACGCAAAACTCTTTAAAACACGCAAAACACTTTAAAACACGAATTTAAATTCGTACTGTAGGGAAGTGAGAA
4329  AATCTGTTAAATGAAACAAAAAATGATAATCATTATCACCATATAAATCATTGATAATAATATATCAAAACAAAACACTTTAAAACACGAATTTAAATTCGTACTGTAGGGAAGTGAGAATA
4453  TTTTTAATCATAAAGGATAAGAAGCCAACCTGAAAAAACCTTTATTATTGGCATTGTTTTCAAAAAAACATGTTCAAAAAACTTTGAATATATTGAAATATTTAGAGATGTATTCAAAAAGAATCGAGAATTTAAATTCTAGATTCTTATATATT
4577  CATCCAAAATATTAGCCAGCAAAAATCAAAAGGTATTAAATAAATATATTATTAATTCGAGTTCAGAGAACACTTTTCAATCACTTTGATAAAAACACACAAATTAATAAA
4701  TCAAAACCAAAAGGCATCAAAAGGTATTAAATAAATATATTATTAATTCGAGTTCAGAGAACACTTTTCAATCACTTTGATAAAAACACACAAATTAATAAA
4825  TACATGCATACACCAAAAGACTTACTTTGGCCTTATTTGAAAATTCAATATATATTTTAAAAGACAAAAAAATATCTTACGTAGTTTTTACTTTTACTAATCCTAATTAAATAATATTTACACACGCAT
4949  AAACGTGCAAATTGTTACTTTGGCCCTTATTTGAAAATTCAATATATATATATCTTTGAATTGTTATACAAATTTATGCAATGATTTCAACTAATTAATATGACGAACTAAATTGATATCGAATGACGAACTAAAATTTGTATAATGACGAACATGAAGTT
5073  AATTTTACTTTAAATGTTTGGCCTTATTTGAACTTAACTTAAATCAAATTTATTCTAGTAAAATAACAACACTGTAAAATATTAATAAATAAAAATTAAAGT
5197  TAAAGTGATTCTTTATTATGTAAAAGAAGACAAAAAATATCTTACGTAGTCTTTTACTTTTTACTGTCCAATTTTACTTTTACTAATCCTAATTTAATTATCTAATCCTTAATTAAATATTACACACGCAT
5321  ACACACGCATCACACCCTACACATACGGCTAAATGCTAATTTAATTTAAGTCAACCTAATTTATAAATTGTTATAATGACGAACTAAAATTGTATAATGACATGAACATGGACATATACTTGGA
5445  AATAACTCTATCAAACGAGCTAATGTTTAAATCTCTTGTTAAATATAGTCTGCACTTCGACAAACGAAAATCAGTGAATTC
```

Fig. 4C

POLYNUCLEOTIDES ENCODING INSECT STEROID HORMONE RECEPTOR POLYPEPTIDES AND CELLS TRANSFORMED WITH SAME

This invention was made in part with Government support under Grant DCB 8405370 from the National Science Foundation. The Government may have certain rights in this invention.

This is a continuation Ser. No. 07/485,749 filed Feb. 26, 1990, now abandoned.

FIELD OF THE INVENTION

This invention relates generally to the use of recombinant DNA methods as applied to the nucleic acid sequences and polypeptides characteristic of insect steroid receptor superfamily members and, more particularly, to uses of such receptors and the DNA regulatory elements associated with genes whose expression they regulate for the production of proteins in cultured cells and, and to uses of such hormone receptor proteins and genes in identifying new hormones that control insect development.

BACKGROUND OF THE INVENTION

The temporal sequence of gene expression determines the nature and sequence of steps in the development of the adult animal from the fertilized egg. The common fruit fly, *Drosophila melanogaster*, provides a favorable model system for studying this genetic control of development. Various aspects of Drosophila development are representative of general insect and, in many respects, vertebrate development.

The steroid hormone 20-OH ecdysone, also known as β-ecdysone, controls timing of development in many insects. See generally, Koolman (ed.), *Ecdysone: From Chemistry to Mode of Action*, Thieme Medical Pub., N.Y. (1989), which is hereby incorporated herein by reference. The generic term "ecdysone" is frequently used as an abbreviation for 20-OH ecdysone. Pulses, or rises and falls, of the ecdysone concentration over a short period of time in insect development are observed at various stages of Drosophila development.

These stages include embryogenesis, three larval stages and two pupal stages. The last pupal stage ends with the formation of the adult fly. One studied effect of ecdysone on development is that resulting from a pulse at the end of the third, or last, larval stage. This pulse triggers the beginning of the metamorphosis of the larva to the adult fly. Certain tissues, called imaginal tissues, are induced to begin their formation of adult structures such as eyes, wings and legs.

During the larval stages of development, giant polytene chromosomes develop in the non-imaginal larval tissues. These cable-like chromosomes consist of aggregates comprising up to about 2,000 chromosomal copies. These chromosome aggregates are extremely useful because they provide the means whereby the position of a given gene within a chromosome can be determined to a very high degree of resolution, several orders of magnitude higher than is typically possible for normal chromosomes.

A "puff" in the polytene chromosomes is a localized expansion or swelling of these cable-like polytene chromosome aggregates that is associated with the transcription of a gene at the puff locus. A puff is, therefore, an indicator of the transcription of a gene located at a particular position in the chromosome.

A genetic regulatory model was proposed to explain the temporal sequence of polytene puffs induced by the ecdysone pulse which triggers the larval-to-adult metamorphosis. See, Ashburner et al., "On the Temporal Control of Puffing Activity in Polytene Chromosomes," *Cold Spring Harbor Symp. Quant. Biol.* 38:655–662 (1974). This model proposed that ecdysone interacts reversibly with a receptor protein, the ecdysone receptor, to form an ecdysone-receptor complex. This complex would directly induce the transcription of a small set of "early" genes responsible for a half dozen immediately induced "early" puffs. These early genes are postulated to encode regulatory proteins that induce the transcription of a second set of "late" genes responsible for the formation of the "late" puffs that appear after the early puffs. The model thus defines a genetic regulatory hierarchy of three ranks, where the ecdysonereceptor gene is in the first rank, the early genes in the second rank and the late genes in the third. While this model derived form the puffing pattern observed in a non-imaginal tissue, similar genetic regulatory hierarchies may also determine the metamorphic changes in development of the imaginal tissues that are also targets of ecdysone, as well as the changes in tissue development induced by the pulses of ecdysone that occur at other developmental stages.

Various structural data have been derived from vertebrate steroid and other lipophilic receptor proteins. A "superfamily" of such receptors has been defined on the basis of their structural similarities. See, Evans, "The Steroid and Thyroid Hormone Receptor Superfamily," *Science* 240:889–895 (1988); Green and Chambon, "Nuclear Receptors Enhance Our Understanding of Transcription Regulation," *Trends in Genetics* 4:309–314 (1988), both of which are hereby incorporated herein by reference. Where their functions have been defined, these receptors, complexed with their respective hormones, regulate the transcription of their primary target genes, as proposed for the ecdysone receptor in the above model.

Cultivated agriculture has greatly increased efficiency of food production in the world. However, various insect pests have found it advantageous to seek out and exploit cultivated sources of food to their own advantage. These insect pests typically develop by a temporal sequence of events which are characteristic of their order. Many, including Drosophila, initially develop in a caterpillar or maggot-like larval form. Thereafter, they undergo a significant metamorphosis from which an adult emerges having characteristic anatomical features. Anatomic similarity is a reflection of developmental, physiological and biochemical similarities shared by these creatures. In particular, the principles of the insect ecdysteroid-hormone receptors and development, as described by Ashburner above, likely would be shared by many different types of insects.

As one weapon against the destruction of cultivated crops by insects, organic molecules with pesticidal properties are used commonly in attempts to eliminate the insect populations. However, the ecological side effects of these pesticides, due in part to their broad activity and lack of specificity, and in part, to the fact that some of these pesticides are not easily biodegradable, significantly affect populations of both insect and other species of animals. Some of these organisms may be advantageous from an ecological or other perspective. Furthermore, as the insect populations evolve in directions to minimize the effects of the applied pesticides, the amounts of pesticides applied are often elevated so high as to cause significant effects on other animals, including humans, which are affected directly or indirectly by the application of the pesticides. Thus, an important need exists for both highly specific pesticides or highly active pesticides which have biological effects only on the species of animals targeted by the pesticides, and are biodegradable. Novel insect hormones which, like the ecdysteroids, act by complexing with insect members of the steroid receptor superfamily to control insect development, are likely candidates for pesticides with these desirable properties.

From a different perspective, many medically and commercially important proteins can be produced in a usable form by genetically engineered bacteria. However, many expressed proteins are processed incorrectly in bacteria and are preferably produced by genetically engineered eucaryotic cells. Typically, yeast cells or mammalian tissue-culture cells are used. Because it has been observed that protein processing of foreign proteins in yeast cells is also frequently inappropriate, mammalian cultured cells have become the central focus for protein production. It is common that the production of large amounts of foreign proteins makes these cells unhealthy, which may affect adversely the yield of the desired protein. This problem may be circumvented, in part, by using an inducible expression system. In such a system, the cells are engineered so that they do not express the foreign protein, and therefore are not unhealthy, until an inducing agent is added to the growth medium. In this way, large quantities of healthy cells can be produced and then induced to produce large amounts of the foreign protein. Unfortunately, in the presently available systems, the inducing agents themselves, such as metal ions or high temperature, adversely affect the cells, thus again lowering the yield of the desired foreign protein the cells produce. A need therefore exists for the development of innocuous inducing factors for efficient production of recombinant proteins. Such innocuous factors could also prove invaluable for human therapy, where the individual suffers from lack of the ability to produce particular proteins. by using methods similar to those for producing proteins in cultured cells, such innocuous factors for inducing thee synthesis of the required protein could be used for controlling both the timing and the abundance of the protein produced in the affected individual.

The hormones that complex with mammalian or other vertebrate members of the steroid receptor superfamily are unlikely candidates for such innocuous factors, nor have they been found to satisfy the required properties of such factors, because mammalian cells contain these receptors, or highly homologous proteins, that would alter the expression of many target genes in the presence of the respective hormone, thereby adversely affecting the host cells.

For these and other reasons, obtaining steroid receptors or nucleic acid information about them has been a goal of researchers for several years. Unfortunately, efforts have been unsuccessful despite significant investment of resources. The absence of information on the structure and molecular biology of steroid receptors has significantly hindered the ability to produce such products.

Thus, there exists a need for detailed sequence information on insect members of the steroid receptor superfamily, and the genes that encode these receptors and for resulting reagents useful in finding new molecules which may act as agonists or antagonists of natural insect members of the steroid receptor superfamily, or as components of systems for highly specific regulation of recombinant proteins in mammalian cells.

SUMMARY OF THE INVENTION

In accordance with the present invention, isolated recombinant nucleic acids are provided which, upon expression, are capable of coding for other than a native vertebrate steroid receptor or fragment thereof. These nucleic acids typically comprise a segment having a sequence substantially homologous to one or more coding regions of domains A, B, D, E or F from an insect steroid receptor superfamily member gene having steroid binding domain homology. Preferably, the nucleic acids encode a polypeptide capable of binding to a ligand for an insect steroid receptor superfamily member and are capable of hybridizing to an insect steroid receptor superfamily member gene segment under selective hybridization conditions, usually stringent hybridization conditions. Mammalian cells transformed with the nucleic acids are also provided.

In another embodiment, isolated recombinant nucleic acids are included that have sequence exhibiting identity over about 20 nucleotides of a coding segment of an insect steroid receptor superfamily member having steroid binding domain homology. The nucleic acids can be transformed into cells to express a polypeptide which binds to a control element responsive to a ligand of an insect steroid receptor superfamily.

Alternatively, an isolated DNA molecule is provided comprising a DNA sequence capable of binding to an insect steroid receptor superfamily member other than 20-OH ecdysone receptor, such as DHR3, E75A or E75B. The DNA sequence may be present in an expression vector and promote transcription of an operably linked sequence (e.g., encoding a polypeptide) in response to binding by an insect steroid receptor superfamily member. Also contemplated are recombinant nucleic acids comprising a controlling element responsive to a ligand of an insect steroid receptor superfamily member ligand responsive controlling element (e.g., an alcohol dehydrogenase promoter), a non-heat shock promoter sequence (e.g., an alcohol dehydrogenase promoter) and a sequence comprising a reporter gene.

Additional embodiments of the present invention include polypeptides comprising an insect steroid receptor superfamily member or fragment thereof, wherein such polypeptide is substantially free of naturally-associated insect cell components and exhibits a biological activity characteristic of an insect steroid receptor superfamily member with a hormone binding domain. Preferably, the insect steroid receptor superfamily member or fragment thereof also comprises a DNA binding domain and the polypeptide is capable of binding to a hormone analogue selected from the group consisting of an insect hormone, an insect hormone agonist and an insect hormone antagonist. The polypeptide can comprise a zinc-finger domain and usually is capable of binding to a DNA controlling element responsive to an insect hormone. As desired, the polypeptide may be fused to a second polypeptide, typically a heterologous polypeptide which comprises a second steroid receptor superfamily member.

Fragments of such polypeptides can have a sequence substantially homologous to consensus E1, E2 or E3 region sequences. By way of example, a preferred fragment has a sequence comprising:

a segment at least about 25% homologous to a consensus E1 region sequence;

a segment at least about 30% homologous to a consensus E2 region sequence; and a segment at least about 30% homologous to a consensus E3 region sequence.

The polypeptides of the present invention have a variety of utilities. For example, a method for selecting DNA sequences capable of being specifically bound by an insect steroid receptor superfamily member can comprise the steps of screening DNA sequences for binding to such polypeptides and selecting DNA sequences exhibiting such binding. Alternatively, methods for selecting ligands specific for binding to a hormone binding domain of an insect steroid receptor superfamily member can comprise the steps of screening compounds for binding to one or more superfamily members and selecting compounds exhibiting specific binding to the members. Also included are methods for modulating insect physiology or development (e.g., killing) comprising the steps of screening compounds for binding to an insect steroid receptor superfamily member, selecting compounds exhibiting said binding and administering the ligand to an insect.

Additionally provided are methods for selecting ligands specific for binding to a ligand binding domain of an insect steroid receptor superfamily member comprising combining:

(i) a fusion polypeptide which comprises a ligand binding domain functionally linked to a DNA binding domain of a second steroid receptor superfamily member; and (ii) a second nucleic acid sequence encoding a second polypeptide, wherein expression of the second nucleic acid sequence is responsive to binding by the DNA binding domain;

screening compounds for an activity of inducing expression of said second polypeptide; and selecting said compounds.

Also provided are methods for producing a polypeptide comprising the steps of:

selecting a cell, typically a mammalian or plant cell which is substantially insensitive to exposure of an insect steroid receptor superfamily ligand;

introducing into said cell:

(i) a receptor for the ligand; and (ii) a nucleic acid sequence encoding the polypeptide, the nucleic acid sequence operably linked to a controlling element responsive to presence of the selected ligand, wherein a transformed cell is produced; and exposing the transformed cell to the ligand.

BRIEF DESCRIPTION OF THE DRAWINGS

FIG. 1. pMTEcR, a $Cu^{2+}$-inducible EcR expression plasmid. The $P_{MT}$, EcR ORF and Act 5c poly A elements are defined in Experimental Example III, part A. The HYG$^r$ ORF confers hygromycin resistance and is under control of the promoter in the LTR of Drosophila transposable elements, copia. The SV40 intron/poly A element provides an intron for a possible splicing requirement, as well as a polyadenylation/cleavage sequence for the HYG$^r$ ORF mRNA. The pAT153 DNA derives from a bacterial plasmid.

FIG. 2. The ecdysone-inducible pEcRE/Adh/βgal reporter plasmid. See the text of Experimental Example III, part B, for the construction of this plasmid and the definitions of all symbols (except the SV40 splice and poly A) which are defined in the figure legend.

FIG. 3. The constitutive EcR expression plasmid, pAct-EcR. The construction of this plasmid and the definition of the symbols are given in Experimental Example III, part B.

FIG. 4(A–C). The cDNA sequence of the EcR gene. Numerals at the left refer to the nucleotide sequences; those on the right to the amino acid sequence in the EcR protein. Nucleotides 1–5194 are the sequence of EcR-17 eDNA, while nucleotides 5195–5534 derive from the EcR-9 cDNA.

The underlined sequences in the 5' and 3' untranslated regions refer, respectively, to the ATG codons and the AATAAA consensus polyadenylation signals. Positions of the introns and the donor and acceptor splice sequences are indicated above the cDNA sequence in small type. The amino acid sequences homologous to the conceived DNA-binding (C region) and hormone-binding (E region) domains of the steroid receptor superfamily are underlined.

DESCRIPTION OF THE PREFERRED EMBODIMENTS

The present invention provides novel isolated nucleic acid sequences encoding polypeptide products exhibiting the structure and/or activities of insect members of the steroid receptor superfamily. Having elucidated the structures of these insect steroid receptors from their genes, the separate ligand-binding domains and DNA-binding domains are used individually or in combination to screen for new ligands or DNA sequences which bind to these domains. Thus, for example, receptors may be used to control expression of reporter genes for which sensitive assays exist. Or, the hormone-binding domains serve as reagents for screening new molecules, useful as either agonists or antagonists of steroid receptor superfamily members. Either new classes of molecules may be screened, or selected modifications from known ligands may be used. These new ligands find use as highly specific and highly active, naturally occurring pesticides. Alternatively, structural information about interactions between the ligand and binding domains directs methods for mutagenizing or substituting particular residues in the binding domains, thereby providing for altered binding specificity. Thus, inter alia, the present invention provides for screening for new ligand molecules, for the design of new ligand-binding domain interactions, for producing novel chimaeric steroid receptor superfamily members and for generating new combinations of ligands and binding domains.

The present invention also provides for the isolation or identification of new steroid hormone-responsive elements and associated genes. By appropriate operable linkage of selected sequences to DNA controlling elements which are responsive to binding by the DNA-binding domains of steroid receptor superfamily members, new regulatory combinations result. The present invention further provides for the design of either a binding domain in a member of the insect steroid receptor superfamily that will recognize given DNA sequences, or conversely for the modification of DNA sequences which will bind to particular DNA-binding domains. Both the DNA-binding domain of a superfamily-member polypeptide and its DNA recognition sequence can be coordinately modified to produce wholly new receptor-DNA interactions.

In an alternative embodiment, a DNA-binding sequence recognized by a selected receptor may be operably linked to a desired genetic sequence for inducible expression. Thus, upon administration of a ligand specific for that selected receptor, the desired genetic sequence is appropriately regulated. Expression systems are constructed that are responsive to administration of insect steroid receptor superfamily-specific ligands. By identifying and isolating new members of the insect steroid receptor superfamily, new regulatory reagents become available, both with respect to usable hormones, and with respect to useable controlling elements.

In another embodiment, highly regulatable expression of a gene may be achieved by use of regulatory elements responsive to ligands specific to the superfamily members.

If transformed cells are grown under conditions where expression is repressed or not induced, the cells may grow to higher densities and enjoy less stressful conditions. Upon reaching high density, the regulatory ligand molecule will adjust to cause high expression. If the selected cells are otherwise insensitive to the inducing ligand, the cells will not be affected by exposure to the ligand used to regulate expression. This provides a means both for highly efficient regulatable expression of genes, and for introduction of these genes into intact organisms.

In accordance with specific embodiments of the present invention, nucleic acid sequences encoding portions of insect steroid hormone receptor hormone receptor superfamily members have been elucidated. For example, certain ecdysone receptor polypeptides have been isolated and characterized; specifically, DNA's encoding four different members of the Drosophila steroid receptor superfamily have been characterized. One is the 20-OH ecdysone receptor, also called the ecdysone receptor (EcR), for which a full-length encoding sequence has been determined. A second member is Drosophila hormone receptor 3 (DHR3), a protein with sequence homology to various steroid receptor superfamily members. The third and fourth members of the superfamily are E75A and E75B, closely related proteins. These members are encoded by segments of the same gene, and each possesses sequence homology to other steroid receptor superfamily members.

The DNA sequences encoding each of these members of the insect steroid receptor superfamily provide probes for screening for homologous nucleic acid sequences, both in Drosophila and other genetic sources. This screening allows isolation of homologous genes from both vertebrates and invertebrates. Production of large amounts of the encoded proteins is effected by inserting those sequences into expression systems.

The EcR, DHR3, E75A and E75B genes are each linked to similar DNA sequences which likely function as controlling, or regulatory, elements. These controlling elements are regulated in a fashion characteristic of response to binding by proteins homologous to members of the steroid receptor superfamily. The present invention provides for the isolation of these hormone-responsive control elements, and for their use in regulating gene expression. One embodiment of a DNA construct comprises: (1) multiple copies of an insect steroid receptor superfamily controlling element linked to (2) a minimal gene promoter, preferably not a heat shock gene promoter, which provides highly inducible expression of (3) an operably linked gene. This construct provides a very sensitive assay for the presence of the controlling molecule of the receptor.

Another aspect of the present invention involves cells comprising: (1) isolated recombinant gene segments encoding biologically active fragments of insect steroid receptor superfamily proteins; (2) DNA sequences which bind insect steroid receptors, e.g., the elements involved in hormone-responsive control; or (3) modified receptor proteins. Progeny of cells which are transformed are included within transformed cells generally. In particular, the present invention provides for a system whereby expression of polypeptides is responsive to steroid induction. For instance, a system which expresses the desired protein in response to exposure to ecdysone analogues is constructed by operably linking an ecdysone-responsive enhancer to a peptide encoding segment.

The present invention also provides insect steroid receptor proteins substantially free from naturally-associated insect cell components. Such receptors will typically be either full-length proteins, functional fragments, or fusion proteins comprising segments from an insect steroid receptor protein fused to a heterologous, or normally non-contiguous, protein domain.

The present invention further provides a number of methods for utilizing the subject receptor proteins. One aspect of the present invention is a method for selecting new hormone analogues. The isolated hormone-binding domains specifically bind hormone ligands, thereby providing a means to screen for new molecules possessing the property of binding with high affinity to the ligand-binding region. Thus, a binding domain of an insect steroid receptor superfamily member may be used as a reagent to develop a binding assay. On one level, the binding domains can be used as affinity reagents for a batch or in a column selective process, to selectively retain ligands which find. Alternatively, a functional assay is preferred for its greater sensitivity to ligand-binding. By using a reporter molecule for binding, either through a direct assay for binding, or through an expression or other functional linkage between binding and another function, an assay for binding may be developed. For example, by operable linkage of an easily assayable reporter gene to a controlling element responsive to binding by an insect steroid receptor superfamily member, and where ligand-binding is functionally linked to protein induction, an extremely sensitive assay for the presence of a ligand or of a receptor results. Such a construct useful for assaying the presence of 20-OH ecdysone is described below. This construct is useful for screening for agonists or antagonists of the 20-OH ecdysone ligand.

In particular, this method may be used to detect the ligan which bind to a receptor, i.e., an "orphan receptor," whose ligand is unknown. Binding domains with "unknown" ligands may originate from either newly identified insect steroid receptor superfamily members, or from mutagenesis. A hybrid receptor may be created with a ligand-binding domain and DNA-binding domain from different sources. This would allow screening for ligands for "orphan receptor" binding domains functionally linked to known DNA-binding domains which will control known reporter gene constructs as described below. This system for ligand-receptor binding provides and extremely sensitive assay for ligand-receptor interactions.

Alternatively, the tertiary structure and spatial interactions between a ligand-binding domain from an insect steroid receptor superfamily member and its ligand will direct design for new combinations of ligand-binding domains with ligands. Either method provides for selecting highly specific and unusual ligands which may be bound only by a modification of a natural receptor polypeptide-binding domain. Alternatively, novel steroid hormone analogues may be selected which exhibit modified specificity for binding to a limited group of steroid receptors.

The present invention also provides for new and useful combinations of the various related components. The recombinant nucleic acid sequences encoding the polypeptides, the polypeptide sequences, and the DNA sites to which the receptors bind (i.e., the regulatory, or control, elements) together provide for combining particular components in novel fashions. For instance, upon expression, fusing nucleic acid sequences encoding peptides from different sources will provide polypeptides exhibiting hybrid properties. In particular, hybrid receptors comprising segments from other members of the superfamily, or from other sources, will be made. Hybrid genetic constructs provide for genes exhibiting unusual control and expression characteristics. Combining an insect steroid receptor-responsive enhancer segment with a different polypeptide encoding segment will produce a steroid-responsive expression system for that polypeptide.

The isolation of insect steroid receptors provides for isolation or screening of new ligands for receptor binding. Some of these will interfere with, or disrupt, normal insect development. It may sometimes be important to either accelerate or decelerate insect development, for instance, in preparing sterile adults for release. Alternatively, in certain circumstances, a delay or change in the timing of development may be lethal or may dramatically modify the ability of an insect to affect an agricultural crop. Thus, naturally occurring, biodegradable and highly active molecules to disrupt the timing of insect development will result.

Furthermore, these polypeptides provide the means by which antibodies have been raised. These antibodies possess specificity for binding to particular steroid receptor classes. Thus, reagents for determining qualitative or quantitative presence of these or homologous polypeptides may be produced. Alternatively, these antibodies may be used to separate or purify receptor polypeptides.

Transcription sequences of insect steroid receptor superfamily members

The ecdysone receptor gene is a member of the steroid and thyroid hormone receptor gene superfamily. The steroid receptors and thyroid hormone receptors are components of a collective group of ligand-responsive transcription factors. See, Evans, *Science* 240:889–895 (1988), and Segraves, *Molecular and Genetic Analysis of the E75 Ecdysone-Responsive Gene of Drosophila melanogaster* (Ph.D. thesis, Stanford University 1988), both of which are hereby incorporated herein by reference for all purposes. These receptors show extensive sequence similarity, especially in their "zinc finger" DNA-binding domains, and also in a ligand, or hormone, binding domain. Modulation of gene expression occurs apparently in response to receptor binding to specific control, or regulatory, elements in the DNA. The cloning of receptor cDNAs provides the first opportunity to study the molecular bases of steroid action. The steroid receptor superfamily is a class of receptors which exhibit similarities in structural and functional features. While the term insect is used herein, it will be recognized that the same methods and molecules may be derived form other species of animals, in particular, within the class Insecta, but more broadly should be applicable to all members of the phylum Arthropoda, which use ecdysteroids as hormones. Thus, although the term insect is used herein, it will be recognized that in some circumstances the larger group of arthropods may be also included. Members of the insect steroid receptor superfamily (superfamily) are characterized by functional domains involved in ligand-binding and DNA binding, both of which interact to effect a change in the regulatory state of a gene operably linked to the DNA-binding site of the receptor. Thus, the receptors of the insect steroid receptor superfamily seem to be ligand-responsive transcription factors. The receptors of the present invention exhibit at least a hormone-binding domain characterized by sequence homology to particular regions, labeled E1, E2 and E3.

The members of the insect steroid receptor superfamily are typically characterized by structural homology of particular domains, such as defined initially in the estrogen receptor. Specifically, a DNA-binding domain, C, and a ligand-binding domain, E, are separated and flanked by additional domains as identified by Krust et al. (Krust et al. (1986), *EMBO J.* 5:891–897), which is incorporated herein by reference.

The C domain, or zinc-finger DNA-binding domain, is usually hydrophilic, having high cysteine, lysine and arginine content—a sequence suitable for the required tight binding. The E domain is usually hydrophobic and characterized as regions E1, E2 and E3. The ligand-binding domains of the present invention are typically characterized by having significant homology in sequence and structure to these three regions. Amino proximal to the C domain is a region initially defined as separate A and B domains. Region D separates the more conserved domains C and E. Region D typically has a hydrophilic region whose predicted secondary structure is rich in turns and coils. The F region is carboxy proximal to the E region (see, Krust et al., supra).

The ligand-binding domain of the members of the insect steroid receptor superfamily is typically carboxyl-proximal, relative to a DNA-binding domain described below. See, Evans, *Science* 240:889–895. The entire hormone-binding domain is typically between about 200 and 250 amino acids but may be less. This domain has the subregions of high homology, termed the E1, E2 and E3 regions. See Table 4.

The E1 region is 19 amino acids long with a consensus sequence AKX(L/I)PGFXXLT(L/I)(D/E)DQITLL, where X represents any amino acid and the other letters are the standard single-letter code. Positions in parentheses are alternatives. Typically, members of the insect steroid receptor superfamily will have at least about five matches out of the sixteen assigned positions, preferably at least about nine matches, and in preferred embodiments, at least about ten matches. Alternatively, these insect steroid receptor superfamily members will have homologous sequences exhibiting at least about 35% homology, preferably at least about 55% homology and more preferably at least about 60% to 70% homology at positions assigned preferred amino acids.

The E2 region is a 19 amino-acid segment with a consensus sequence:

E(F/Y)(A/V)(L/C)(L/M)KA(I/L)(V/L)L(L/I)
(N/S)(S/P)D(P/–)(R/K)(P/D)GL, where - represents an optional absence of an amino acid. Typically, an insect steroid receptor superfamily member will exhibit at least about six matches, preferably at least about eight matches and more preferably at least about nine matches. Alternatively, E2 sequences of insect steroid receptor superfamily members exhibit at least about 30% homology, preferably at least about 40% homology, and more preferably at least about 45% homology.

The E3 region is a 12 amino-acid segment with a consensus sequence

LXKLLXXLPDLR.

The insect steroid receptor superfamily members will typically show at least about four matches out of the nine assigned preferences in the E3 region, preferably at least about five matches and more preferably at least about six matches. Alternatively, over the assigned positions, members of the insect steroid receptor superfamily will typically exhibit at least about 45% homology, usually at least about 55% homology and preferably at least about 65% homology.

In preferred embodiments, the insect steroid receptor superfamily members will exhibit matching of at least about five positions in an E1 region, at least about six positions in an E3 region and at least about four positions in an E3 region. Thus, a combination of all three regional sequence constraints is especially preferred.

The DNA-binding domain of these insect steroid receptor superfamily members is characterized by a "zinc fingers" motif. See, Evans, *Science* 240:889–895. The domain is typically amino proximal to the ligand, or hormone, binding site. Typically, the DNA-binding domain of the insect steroid receptor superfamily members is characterized by clustering of basic residues, a cysrich composition and homology in sequence. See, Evans, R. M. (1988), *Science* 240:889–89; and Experimental section below. Significant sequence homology among superfamily members exists. Typically, the insect steroid receptor superfamily members will exhibit at least about [30]% homology in the 67±1 amino acid region of this domain, usually at least about 40% homology, and preferably at least about 45% homology.

Steroids are derivatives of the saturated tetracyclic hydrocarbon perhydrocyclopentanophenanthrene. Among the molecules in the group "steroids" are the bile acids, cholic acid and deoxycholic acid, the adrenocortical steroids, such as corticosterone and aldosterone, the estrogens such as estrone and β-estradiol, the androgens, such as testosterone and progesterone, and the ecdysteroids. The terms steroid or steroid hormones are used interchangeably herein and are intended to include all steroid analogues. Typically, steroid analogues are molecules which have minor modifications of various peripheral chemical groups. See, Koolman (ed.) (1989), cited above, for details on ecdysteroids.

Although ligands for the insect steroid receptor superfamily members have historically been characterized as steroids, the term "steroid" in the label "insect steroid receptor superfamily" is not meant literally. The use of "steroid" has resulted from a historical label of members of a group recognized initially to include only steroids. However, the limitation no longer is applicable. Thus, there may be members of the insect steroid receptor superfamily, as defined herein, whose ligand-binding specificity is not directed to "steroids." Typically, the ligands for members of the insect steroid receptor superfamily are lipophilic molecules.

The term "ligand" is meant herein to exclude the DNA sequence to which the DNA-binding domain binds. Thus, the term ligand is meant to refer to the molecules that bind the domain described here as the "hormone-binding domain." Also, a ligand for an insect steroid receptor superfamily member is a ligand which serves either as the natural ligand to which the member binds, or a functional analogue which may serve as an agonist or antagonist. However, the functional term "hormone" is used, again, because of the historic usage to describe the receptors, but is meant to apply to virtually any chemical messenger used to communicate between cell types. These molecules are typically used in intercellular signal transduction, but are not limited to those molecules having slow or systemic effects.

Substantial homology in the nucleic acid context means either that the segments, or their complementary strands, when compared, are identical when optimally aligned, with appropriate nucleotide insertions or deletions, in at least about 60% of the residues, usually at least about 80% and preferably at least 90% of the nucleotides. Alternatively, substantial homology exists when the segments will hybridize under selective hybridization conditions, to a strand, or its complement, typically using a sequence derived from Table 1, 2 or 3. Selectivity of hybridization exists when hybridization occurs which is more selective than total lack of specificity. Typically, selective hybridization will occur when there is at least about 55% homology over a stretch of at least about 14/25 nucleotides, preferably at least about 65%, more preferably at least about 75%, and most preferably at least about 90%. See, Kanehisa, M. (1984), *Nucleic Acids Res.* 12:203–213, which is incorporated herein by reference. Stringent hybridization conditions will typically include salt concentrations of less than about 1M, more usually less than about 500 mM and preferably less than about 200 mM. Temperature conditions will typically be greater than 20° C., more usually greater than about 30° C. and preferably in excess of about 37° C. As other factors may significantly affect the stringency of hybridization, including, among others, base composition and size of the complementary strands, presence of organic solvents and extent of base mismatching, the combination of parameters is more important than the absolute measure of any one.

A gene for an insect steroid receptor superfamily member gene includes its upstream (e.g., promoter) and downstream operably linked controlling elements, as well as the complementary strands. It also comprises the segment encoding the transcription unit, including both introns and exons. Thus, an isolated gene allows for screening for new steroid receptor genes by probing for genetic sequences which hybridize to either controlling or transcribed segments of a receptor gene of the present invention. Three segments of particular interest are the controlling elements, both upstream and downstream, and segments encoding the DNA-binding segments and the hormone-binding segments.

Insect steroid receptor superfamily member polypeptides

A polypeptide sequence of the ecdysone receptor is represented in Table 2. Other insect steroid receptor superfamily member polypeptide sequences are set forth in Tables 1 and 3. Preferred nucleic acid sequences of the cDNAs encoding these insect steroid receptor superfamily member polypeptides are also provided in the corresponding tables. Other nucleic acids may be used to encode the proteins, making use of the degeneracy or non-universality of the genetic code.

As used herein, the term "substantially pure" describes a protein or other material which has been separated from its native contaminants. Typically, a monomeric protein is substantially pure when at least about 60 to 75% of a sample exhibits a single polypeptide backbone. Minor variants or chemical modifications typically share the same polypeptide sequence. Usually a substantially pure protein will comprise over about 85 to 90% of a protein sample, and preferably will be over about 99% pure. Normally, purity is measured on a polyacrylamide gel, with homogeneity determined by staining. Alternatively, for certain purposes high resolution will be necessary and HPLC or a similar means for purification will be used. For most purposes, a simple chromatography column or polyacrylamide gel will be used to determine purity.

The term "substantially free of naturally-associated insect cell components" describes a protein or other material which is separated from the native contaminants which accompany it in its natural insect cell state. Thus, a protein which is chemically synthesized or synthesized in a cellular system different from the insect cell from which it naturally originates will be free from its naturally-associated insect cell components. The term is used to describe insect steroid receptor superfamily members and nucleic acids which have been synthesized in mammalian cells or plant cells, *E. coli* and other procaryotes.

The present invention also provides for analogues of the insect steroid receptor superfamily members. Such analogues include both modifications to a polypeptide backbone and variants and mutants of the polypeptides. Modifications include chemical derivatizations of polypeptides, such as acetylations, carboxylations and the like. They also include glycosylation modifications and processing variants of a typical polypeptide. These processing steps specifically include enzymatic modifications, such as ubiquinization. See, e.g., Hershko and Ciechanover (1982), "Mechanisms of Intracellular Protein Breakdown," *Ann. Rev. Bioch.,* 51:335–364.

Other analogues include genetic variants, both natural and induced. Induced mutants may be derived from various techniques including both random mutagenesis using reagents such as irradiation or exposure to EMS, or may take the form of engineered changes by site-specific mutagenesis or other techniques of modern molecular biology. See, Sambrook, Fritsch and Maniatis (1989), *Molecular Cloning: A Laboratory Manual* (2d ed.), CSH Press.

As described above, the DNA-binding zinc fingers segment of a receptor shows high specificity of recognition of specific target DNA sequences. An understanding of the DNA protein-binding interactions provides for the modification in a rational manner either DNA or protein characteristics, or both, to effect specificity of binding for modulation of enhancer activity. More importantly, isolation of genes for new members of the insect steroid receptor superfamily allows their use to produce the receptor polypeptides and to isolate and isolate new controlling elements. By using the DNA-binding domains, as described above, controlling elements which are responsive to the ligands bound by the corresponding superfamily members may be identified and isolated. This shall yield a variety of controlling elements responsive to ligands. By the methods described above, the ligands for any particular member of the insect steroid receptor superfamily may be identified.

The controlling elements typically are enhancers, but may also include silencers or various other types of ligand-responsive elements. They may operate at large distances, but will typically be within about 50 kb, usually within about 35 kb, more usually within about 20 kb and preferably within about 7 kb of the genes that these elements regulate.

Polypeptide fragments and fusions

Besides substantially full-length polypeptides, the present invention provides for biologically active fragments of the polypeptides. Significant biological activities include ligand-binding, DNA binding, immunological activity and other biological activities characteristic of steroid receptor superfamily members. Immunological activities include both immunogenic function in a target immune system, as well as sharing of immunological epitopes for binding, serving as either a competitor or substitute antigen for asteroid receptor epitope.

For example, ligand-binding or DNA-binding domains may be "swapped" between different new fusion polypeptides or fragments. Thus, new chimaeric polypeptides exhibiting new combinations of specificities result from the functional linkage of ligand-binding specificities are DNA-binding domains. This is extremely useful in the design of inducible expression systems.

For immunological purposes, immunogens may be produced which tandemly repeat polypeptide segments, thereby producing highly antigenic proteins. Alternatively, such polypeptides will serve as highly efficient competitors for specific binding. Production of antibodies to insect steroid receptor superfamily members is described below.

The present invention also provides for other polypeptides comprising fragments of steroid receptor superfamily members. Thus, fusion polypeptides between the steroid receptor segments and other homologous or heterologous proteins are provided. Homologous polypeptides may be fusions between different steroid receptor superfamily members, resulting in, for instance, a hybrid protein exhibiting ligand specificity of one member and DNA-binding specificity of another. Likewise, heterologous fusions may be constructed which would exhibit a combination of properties or activities of the derivative proteins. Typical examples are fusions of a reporter polypeptide, e.g., luciferase, with another domain of a receptor, e.g., a DNA-binding domain, so that the presence or location of a desired ligand may be easily determined. See, e.g., Dull et al., U.S. Pat. No. 4,859,609, which is hereby incorporated herein by reference. Other typical gene fusion partners include "zinc finger" segment swapping between DNA-binding proteins, bacterial β-galactosidase, trpE Protein A, β-lactamase, alpha anylase, alcohol dehydrogenase and yeast alpha mating factor. See, e.g., Godowski et al. (1988), *Science* 241:812–816; and Experimental section below.

Insect steroid receptor superfamily member expression

With the sequence of the receptor polypeptides and the recombinant DNA sequences encoding them, large quantities of members of the insect steroid receptor superfamily will be prepared. By the appropriate expression of vectors in cells, high efficiency production may be achieved. Thereafter, standard purification methods may be used, such as ammonium sulfate precipitations, column chromatography, electrophoresis, centrifugation, crystallization and others. See various volumes of *Methods in Enzymology* for techniques typically used for protein purification. Alternatively, in some embodiments high efficiency of production is unnecessary, but the presence of a known inducing protein within a carefully engineered expression system is quite valuable. For instance, a combination of: (1) a ligand-responsive enhancer of this type operably linked to (2) a desired gene sequence with (3) the corresponding insect steroid receptor superfamily member together in an expression system provides a specifically inducible expression system. Typically, the expression system will be a cell, but an in vitro expression system may also be constructed.

The desired genes will be inserted into any of a wide selection of expression vectors. The selection of an appropriate vector and cell line depends upon the constraints of the desired product. Typical expression vectors are described in Sambrook et al. (1989). Suitable cell lines may be selected from a depository, such as the ATCC. See, ATCC Catalogue of Cell Lines and Hybridomas (6th ed.) (1988); ATCC Cell Lines, Viruses, and Antisera, each of which is hereby incorporated herein by reference. The vectors are introduced to the desired cells by standard transformation or transfection procedures as described, for instance, in Sambrook et al. (1989).

Fusion proteins will typically be made by either recombinant nucleic acid methods or by synthetic polypeptide methods. Techniques for nucleic acid manipulation are described generally, for example, in Sambrook et al. (1989), *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield, *J. Amer. Chem. Soc.* 85:2149– 2156 (1963).

The recombinant nucleic acid sequences used to produce fusion proteins of the present invention may be derived from natural or synthetic sequences. Many natural gene sequences are obtainable from various cDNA or from genomic libraries using appropriate probes. See, GenBank™, National Institutes of Health. Typical probes for steroid receptors may be selected from the sequences of Tables 1, 2 or 3 in accordance with standard procedures. Suitable synthetic DNA fragments may be prepared by the phosphoramidite method described by Beaucage and Carruthers, *Tetra. Letts.* 22:1859–1862 (1981). A double stranded fragment may then be obtained either by synthesizing the complementary strand and annealing the strand together under appropriate conditions or by adding the complementary strand using DNA polymerase with an appropriate primer sequence.

With the isolated steroid receptor genes, segments of the transcribed segments may be used as probes for isolating homologous sequences from different sources, either different animals, or different but homologous genes exhibiting sequence homology. By selection of the segment used as a probe, particular functionally associated segments will be isolated. Thus, for example, other nucleic acid segments encoding either ligand-binding or DNA-binding domains of new receptors will be isolated. Alternatively, by using steroid-responsive controlling elements as a probe, new steroid-responsive elements will be isolated, along with the associated segment of DNA whose expression is regulated. This method allows for the isolation of ligand-responsive genes, many of which are, themselves, also members of the insect steroid receptor superfamily.

The natural or synthetic DNA fragments coding for a desired steroid receptor fragment will be incorporated into DNA constructs capable of introduction to and expression in an in vitro cell culture. Usually the DNA constructs will be suitable for replication in a unicellular host, such as yeast or bacteria, but may also be intended for introduction to, with and without and integration within the genome, cultured mammalian or plant or other eucaryotic cell lines. DNA constructs prepared for introduction into bacteria or yeast will typically include a replication system recognized by the host, the intended DNA fragment encoding the desired receptor polypeptide, transcription and translational initiation regulatory sequences operably linked to the polypeptide encoding segment and transcriptional and translational termination regulatory sequences operably linked to the polypeptide encoding segment. The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known. See, Sambrook et al. (1989). Conveniently available expression vectors which include the replication system and transcriptional and translational regulatory sequences together with the insertion site for the steroid receptor DNA sequence may be employed. Examples of workable combinations of cell lines and expression vectors are described in Sambrook et al. (1989); see also, Metzger et al. (1988), *Nature* 334:31–36.

Genetic constructs

The DNA segments encoding the members of the insect steroid receptor superfamily will typically be utilized in a plasmid vector. Two separate embodiments exist, the first having an expression control DNA sequence operably linked to the insect steroid receptor superfamily member coding sequences for expression of the insect steroid receptor superfamily member alone. A second includes an insect steroid receptor superfamily member as a component of an expression system for another gene to make expression of that other gene ligand responsive. This latter embodiment is separately described just below. The expression control sequences will be commonly eucaryotic enhancer or promoter systems in vectors capable of transforming or transfecting eucaryotic host cells. Once the vector has been incorporated into the appropriate host, the host, depending on the use, will be maintained under conditions suitable for high level expression of the nucleotide sequences.

Steroid-responsive expression of selected genes

For steroid-responsive expression of other genes, the steroid receptor gene will typically be cotransformed with a recombinant construct comprising a desired gene for expression operably linked to the steroid-responsive enhancer or promoter element. In this use, a single expression system will typically comprise a combination of (1) a controlling element responsive to a ligand of an insect steroid receptor superfamily member, (2) a desired gene for expression, operably linked to the controlling element, and (3) an insect steroid receptor superfamily member which can bind to the controlling element. Usually, this system will be within a cell, but an in vitro system is also possible. The insect steroid receptor superfamily member will typically be provided by expression of a nucleic acid encoding it, though it need not be expressed at particularly high levels. Thus, in one preferred embodiment, the system will be achieved through cotransformation of a cell with both the regulatable construct and another segment encoding the insect steroid receptor superfamily member. Usually, the controlling element will be an enhancer element, but it may work in reverse and be used to repress expression. In this embodiment, the ligand for the insect steroid receptor superfamily member will be provided or withheld as appropriate for the desired expression properties.

A particularly useful genetic construct comprises an alcohol dehydrogenase promoter operably linked to an easily assayable reporter gene, e.g., β-galactosidase. In a preferred embodiment of this construct, a multiplicity of copies of the insect steroid receptor superfamily member is used. For example, operable linkage of controlling elements responsive to insect steroid receptor superfamily members, e,g., EcR, DHR3, E75A and E75B, to the alcohol dehydrogenase (ADH) promoter, or others as described above, and protein coding sequences for a particular reporter protein, as described above leads to steroid-responsive expression of that protein. This controlling element responsive to the construct provides a very sensitive system for the detection of responsive expression. This will be used in sensitive assays for the presence of a receptor-ligand interaction, allowing for detection of either ligand or receptor or both.

DNA sequences will normally be expressed in hosts after the sequences have been operably linked to (i.e., positioned to ensure the functioning of) an expression control sequence. These expression vectors are typically replicable in the host organisms either as episomes or as an integral part of the host chromosomal DNA. Commonly, expression vectors will contain selection markers, e.g., tetracycline or neomycin, to permit detection of those cells transformed with the desired DNA sequences (see, e.g., U.S. Pat. No. 4,704,362, which is incorporated herein by reference).

*E. coli* is one procaryotic host useful for cloning the DNA sequences of the present invention. Other microbial hosts suitable for use include bacilli, such as *Bacillus subtilis*, and other enterobacteriaceae, such as Salmonella, Serratia, and various Pseudomonas species.

Other eucaryotic cells may be used, including yeast cells, insect tissue culture cells, avian cells or the like. Preferably, mammalian tissue cell culture will be used to produce the inducible polypeptides of the present invention (see, Winnacker, *From Genes to Clones,* VCH Publishers, N.Y. (1987), which is incorporated herein by reference). Mammalian cells are preferred cells in which to use the insect steroid receptor superfamily member ligand-responsive gene constructs because they naturally lack the molecules which confer responses to the ligands for insect steroid receptor superfamily members.

Since mammalian cells are insensitive to many ligands for insect steroid receptor superfamily members, exposure of these cells to the ligands of the insect steroid receptor superfamily members typically will have negligible physiological or other effects on the cells, or on a whole organism. This insensitivity of the cells to the ligands provides preferred combination of ligand induction with an otherwise insensitive cell. This provides for transformation of insensitive cells with the controlling element operably linked to a derived gene, resulting in an expression system whose ligand for eliciting response causes minimal physiological effects. Therefore, cells can grow and express substantially unaffected by the presence of the ligand. The ligand may cause response either in the positive or negative direction. For example, cells might be desired to be grown to high density before expression. In a positive induction system, the inducing ligand would be added upon reaching high density, but since the ligand itself is innocuous to the cells, the only physiological imbalances result from the expression itself. Alternatively, in a negative repression system, the ligand is supplied until the cells reach a high density, but again, the presence of the ligand is innocuous. Upon reaching a high density, the ligand would be removed. Introduction of these cells into whole organisms may be performed so that the products of expression may be provided to the whole organism. In this circumstance, the natural insensitivity of cells to the ligands will also be advantageous.

Expression vectors for these cells can include expression control sequences, such as an origin of replication, a promoter, an enhancer and necessary processing information sites, such as ribosome-binding sites, RNA splice sites, polyadenylation sites, and transcriptional terminator sequences. Preferably, the enhancers or promoters will be those naturally associated with genes encoding the steroid receptors, although it will be understood that in many cases others will be equally or more appropriate. Other preferred expression control sequences are enhancers or promoters derived from viruses, such as SV40, Adenovirus, Bovine Papilloma Virus, and the like.

Similarly, preferred promoters are those found naturally in immunoglobulin-producing cells (see, U.S. Pat. No. 4,663,281, which is incorporated herein by reference), but SV40, polyoma virus, cytomegalovirus (human or murine) and the LTR from various retroviruses (such as murine leukemia virus, murine or Rous sarcoma virus and HIV) may be utilized. See, *Enhancers and Eukaryotic Gene Expression,* Cold Spring Harbor Press, N.Y., 1983, which is incorporated herein by reference.

The vectors containing the DNA segments of interest (e.g., the steroid receptor gene, the recombinant steroid-responsive gene, or both) can be transferred into the host cell by well-known methods, which vary depending on the type of cellular host. For example, calcium chloride transfection is commonly utilized for procaryotic cells, whereas calcium phosphate treatment may be used for other cellular hosts. (See, generally, Sambrook et al. (1989), *Molecular Cloning: A Laboratory Manual* (2d ed.), Cold Spring Harbor Press, which is incorporated herein by reference.) The term "transformed cell" is meant to also include the progeny of a transformed cell.

As with the purified polypeptides, the nucleic acid segments associated with the ligand-binding segment and the DNA-binding segment are particularly useful. These gene segments will be used as probes for screening for new genes exhibiting similar biological activities, though the controlling elements of these genes are of equal importance, as described below.

Many types of proteins are preferentially produced in eucaryotic cell types because of abnormal processing or modification in other cell types. Thus, mammalian proteins are preferably expressed in mammalian cell cultures. Efficient expression of a desired protein may be achieved, as described above, by placing: (1) a desired protein encoding DNA sequence adjacent to controlling elements responsive to ligands for insect steroid receptor superfamily members and an appropriate promoter. Furthermore, unhealthy cells are particularly difficult to maintain alive and efficiency of expression of exogenous proteins falls. Inducible expression systems partly solve this problem, but the presently available inducing molecules have direct side effects on the cells. By selecting an inducing molecule which otherwise has no effects on the cell, a more natural physiological state of the cells may be achieved in growing the cells to high density. Upon exposure to such an inducing molecule, the cells initially in a healthy state will produce the desired protein at high levels without the harmful effects resulting from the action of the inducing molecule itself. Ecdysteroids and other ligands for insect steroid receptor superfamily members are not normally found in mammalian cells, and thus serve as favorable candidates for a role as innocuous inducing molecules. Cyclic pulses of ligands in a cell culture may provide periods for cells to recover from effects of production of large amounts of exogenous protein.

Additional steroid responsive gene elements have also been isolated using the techniques of the present invention. Other genes adjacent to, and operably linked to, steroid responsive gene controlling elements are selectable by locating DNA segments to which steroid receptors specifically bind or by hybridization to homologous controlling elements. For example, other steroid responsive genes have been isolated. Many of the genes which are ligand-responsive may also be new members of the insect steroid receptor superfamily.

Having provided for the substantially pure polypeptides, biologically active fragments thereof and recombinant nucleic acids comprising genes for them, the present invention also provides cells comprising each of them. By appropriate introduction techniques well known in the field, cells comprising them may be produced. See, e.g., Sambrook et al. (1989).

In particular, cells comprising the steroid responsive controlling elements are provided, and operable linkage of standard protein encoding segments to said controlling elements produce steroid responsive systems for gene expression. Cells so produced may be introduced into intact organisms, for example, plants, insects (including caterpillars and larvae) and animals. This may provide for a form of regulable expression of desired genes but where the regulating ligand has no other effects on the cells because they otherwise lack the receptors and responsive genes. For example, plants the receptors and responsive genes. For example, plants may be induced to fruit at desired times by administration of the appropriate ligand, or animals may be ligand-responsive in production of particular products. And, in fact, biochemical deficiencies may be overcome by ligand-responsive expression of cells introduced into an intact organism which, itself, also otherwise lacks genes responsive to the presence of such a ligand. Cells containing these expression systems may be used in gene therapy procedures, including in humans.

Once a sufficient quantity of the desired steroid receptor polypeptide has been obtained, the protein may be used for various purposes. A typical use is the production of antibodies specific for binding to steroid receptors. These antibodies may be either polyclonal or monoclonal and may be produced by in vitro or in vivo techniques.

For production of polyclonal antibodies, an appropriate target immune system is selected, typically a mouse or rabbit. The substantially purified antigen is presented to the immune system in a fashion determined by methods appropriate for the animal and other parameters well known to immunologists. Typical sites for injection are in the footpads, intramuscularly, intraperitoneally, or intradermally. Of course, another species may be substituted for a mouse or rabbit.

An immunological response is usually assayed with an immunoassay. Normally such immunoassays involve some purification of a source of antigen, for example, produced by the same cells and in the same fashion as the antigen was produced. The immunoassay may be a radioimmunoassay, an enzyme-linked assay (ELISA), a fluorescent assay, or any of many other choices, most of which are functionally equivalent but may exhibit advantages under specific conditions.

Monoclonal antibodies with affinities of $10^8$ $M^{-1}$ preferably $10^9$ to $10^{10}$, or stronger will typically be made by standard procedures as described, e.g., in Harlow and Lane (1988), *Antibodies: A Laboratory Manual,* Cold Spring Harbor Laboratory; or Goding (1986), *Monoclonal Antibodies: Principles and Practice* (2d ed) Academic Press, New York, which are hereby incorporated herein by reference. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter the cells are clonally separated and the supernatants of each clone are tested for their production of an appropriate antibody specific for the desired region of the antigen.

Other suitable techniques involve in vitro exposure of lymphocytes to the antigenic polypeptides or alternatively to selection of libraries of antibodies in phage or similar vectors. See, Huse et al., (1989) "Generation of a Large Combinatorial Library of the Immunoglobulin Repertoire in Phage Lambda," *Science* 246:1275–1281, hereby incorporated herein by reference.

The polypeptides and antibodies of the present invention may be used with or without modification. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescens, chemiluminescers, magnetic particles and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567.

Another use of purified receptor polypeptides is for determination of the structural and biosynthetic aspects of the polypeptides. Structural studies of interactions of the ligand-binding domains with selected ligands may be performed by various methods. The preferred method for structural determination is X-ray crystallography but may include various other forms of spectroscopy or chromatography. See, e.g., Connolly, M. L., *J. Appl. Crystall.,* 16:548 (1983); and Connolly, M. L., *Science* 221:709 (1983), which are hereby incorporated herein by reference. For example, the structure of the interaction between hormone ligand and hormone-binding segments may be determined to high resolution. From this information, minor substitutions or modifications to either or both of the ligand and ligand-binding segment may be made. This information enables the generation of modified interactions between a ligand and its binding segment to either increase or decrease affinity of binding and perhaps increase or decrease response to binding. Likewise, the interaction between the zinc fingers DNA-binding segments with the specific nucleic acid-binding sequence may be similarly modified.

As a separate and additional approach, isolated ligand-binding polypeptide domains may be utilized to screen for new ligands. This permits screening for new agonists or antagonists of a particular steroid receptor. Isolated DNA-binding segments may be used to screen for new DNA sequences which will specifically bind to a particular receptor-binding segment. Typically, these receptor-specific binding sites will be controlling elements for steroid responsive genes. Thus, having isolated these DNA-binding sequences, genes which are responsive to the binding of a given receptor can be isolated. This provides a method for isolating genes which are responsive to induction or inhibition by a given hormone receptor.

In another aspect of the present invention, means for disrupting insect development are provided where new ligand agonists or antagonists are discoverd. These compounds are prime candidate as agonists or antagonists to interfere with the normal insect development. By application of new steroid analogues of ligands for insejct steroid receptor superfamily members, it is possible to modify the normal temporal sequence of developmental events. For example, accelerating insect development will minimize generation time. This may be very important in circumstances where large numbers of insects are desired finally, for instance, in producing sterile males in Mediterranean fly infestations. Alternatively, it may be useful to slow development in a pest infestation, such that the insects reach destructive stages of development only after commercial crops may have passed sensitive stages.

In another commercial application, ligands discovered by methods provided by the present invention may be used in the silk-production industry. Here, the silkworms are artificially maintained in a silk-producing larvae stage, thereby being silk productive for extended time periods. The development of larvae may also be accelerated to reach the silk-producing stage in their life cycle earlier than naturally.

Other analogues of ligands for insect steriod receptor superfamily members may be selected which, upon application, may be completely disruptive of normal development, leading to a lethal result. However, the use of slightly modified natural substances will often have greater specificity of action and much higher activities, thus allowing for lower levels of application. Also, because the ligands may be more lipophilic, they may be more readily absorbed directly into the insect surface or article. Extremely low amounts of natural ligands may be effective in controlling pests. Furthermore, many of these ligands are likely top be relatively easily manufacture, perhaps by biological methods using enzymatic production methods. There may be new ligands for insect steroid receptor superfamily members which may be more species specific or may exhibit a particularly useful spectrum of effectiveness, for example, being lethal to harmful insects. The greater specificity of the hormones will allow avoidance of use of non-specific pesticides possessing undesired deleterious ecological side effects. For instanc,e residue of pesticides accumulate in food, often having deleterious effects on humans. Furthermore, compounds having structures closely analogous to natural compounds may be susceptible to natural mechanisms of biological degradation.

Another aspect of the present invention provides for the isolation or design of new gene segments which are responsive to ligands for insect steroid receptor superfamily members. For example, use of the nucleic acids to screen for homologous sequences by standard techniques will provide genes having similar structural features. Similarly arranged intron structures will typically be characteristic of larger superfamily categories. The preferred domains for screening will be the ligand-binding or DNA-binding segments, however, the DNA segments which are recognized by the DNA-binding domains, i.e., the controlling elements, will also be of particular interest. By screening for new controlling elements, by either sequence homology to other known ones, or by screening with the DNA zinc finger-binding domains of other receptors, additional receptors can be isolated. Receptors and genes important in the general developmental sequence of expression will be discovered. Using this set of developmentally regulated genes will allow selection of particular molecules which are responsible for controlling expression of developmentally regulated genes.

The following experimental section is offered by way of example and not by limitation.

EXPERIMENTAL

EXAMPLE I

CLONING STRUCTURE AND EXPRESSION OF THE DROSOPHILA E75 GENE THAT ENCODES TWO MEMBERS OF THE STEROID RECEPTOR SUPERFAMILY

A. Cloning of Genomic DNA Encompassing the Ecdysone-Inducible 75B Puff Locus
  Methods
    Genomic DNA libraries
    In situ hybridization
B. Identification of a 50-kb Region of Cloned Genomic DNA that Contains Sequences Homologous to Ecdysone-induced Transcripts
  Methods
    Organ culture and RNA isolation
    Southern blot analysis
C. The E75 Gene Contains Two Overlapping Transcription Units: E75A and E75B
  Methods
    cDNA libraries
    Northern blot analysis
    S1 nuclease protection and primer extension analysis
    DNA sequence analysis
D. The E75 Gene Encodes Two Members of the Steroid Receptor Superfamily
    Protein sequence analysis
E. Expression Vectors for E75 Proteins

EXAMPLE II

CLONING, STRUCTURE AND EXPRESSION OF THE ECR AND DHR3 GENES THAT ENCODE ADDITIONAL MEMBERS OF THE STEROID RECEPTOR SUPERFAMILY

Identification and Chromosomal Mapping of EcR and DHR3 Genomic Clones
    Structure of the EcR and DHR3 Genes and Their cDNAs
    Methods
      Isolation of cDNA and additional genomic clones
      DNA sequence analysis
C. The Predicted Amino Acid Sequence of the EcR and DHR3 Proteins and their Implications
D. In Situ Labeling of the EcR and DHR3 Proteins with Antibodies Induced by Proteins Produced in *E. coli*

EXAMPLE III.

THE ECDYSTEROID-BINDING, DNA-BINDING AND GENETIC REGULATORY PROPERTIES OF THE ECR PROTEIN DEMONSTRATE THAT IT IS AN ECDYSONE RECEPTOR

A. The EcR Protein Binds Ecdysteroids
  Methods
    Extracts
    Hormone-binding assays
B. Genetic Regulatory Activity of the EcR Protein in vivo
  Methods
    Construction of the pAdh/βgal, pEcRE/Adh/βgal and pActEcR plasmids
    Transfection and generation of the cell line SRS 1.5
C. Specific Binding of the EcR Protein to Ecdysone Response Elements
  Methods
    Conditions for the DNA binding assay

EXAMPLE IV

RECEPTOR GENE MUTAGENESIS

A. Deletion Mutations
B. E75 Mutations Generated by Ethyl Methane Sulfonate
  Methods
    Strains, markers and chromosomes
    Quantitative Southern blot mapping for detection of mutant lesions
    Molecular cloning of mutant lesions
    Gamma ray mutagenesis
    EMS mutagenesis
    In situ hybridization and cytological analysis

EXPERIMENTAL

EXAMPLE I

CLONING STRUCTURE AND EXPRESSION OF THE DROSOPHILA E75 GENE THAT ENCODES TWO MEMBERS OF THE STEROID RECEPTOR SUPERFAMILY.

The following experiments demonstrate that the E75 gene encodes two members of the steroid receptor superfamily. This is due to the receptor amino acid sequence homology to the conserved DNA-binding and ligand-binding domains of this superfamily, and that E75 is an ecdysone-inducible gene that occupies and is responsible for the ecdysone-inducible early puff at the 75B locus in the Drosophila polytene chromosome.

A. Cloning of Genomic DNA Encompassing the Ecdysone-Inducible 75B Puff Locus

We have used the method of chromosomal walking (Bender, W., P. Spierer, and D. S. Hogness, 1983. Chromosomal walking and jumping to isolate DNA from the Ace and rosy loci and the Bithorax complex in *Drosophila melanogaster*. *J. Mol. Biol.* 168:17–33) to isolate the genomic DNA encompassing the 75B puff region. The starting point for the walk was a genomic clone, λ8253 (a gift of J. Burke), which had been localized by in situ hybridization to the proximal end of 75B. Isolated restriction fragments of λ8253 were used to screen a library of genomic DNA from the Canton S ($C^S$) strain of *D. melanogaster* (Maniatis, T., R. C. Hardison, E. Lacy, J. Lauer, C. O'Connell, D. Quon, G. K. Sim, and A. Efstradiatis, 1978. The isolation of structural genes from libraries of eucaryotic DNA. *Cell* 15:687–701). Genomic clones λcDm3504 and λcDm3505 were isolated by homology to λ8253.

The walk was then extended in both directions until ~100 kb of genomic DNA had been isolated, when the orientation of the walk was determined by in situ hybridization of the terminal segments to polytene chromosomes. Thereafter, the walk was extended in the rightward direction on the molecular map, or distally relative to the centromere. The 350 kb of genomic DNA encompassed by the walk corresponds to the chromosomal region between bands 75A6–7 and 75B11–13, as determined by in situ hybridization. This region includes the 75B puff, which appears to initiate by simultaneous decondensation of chromosomal bands 75B3–5 and then spreads to surrounding bands.

Methods
Genomic DNA libraries

Canton S genomic DNAs were isolated from a library of sheared, EcoRI-linkered Canton S DNA cloned into the Charon 4 λ phage vector (Maniatis, T., R. C. Hardison, E. Lacy, J. Lauer, C. O'Connell, D. Quon, G. K. Sim, and A. Efstradiatis, 1978. The isolation of structural genes from libraries of eucaryotic DNA. *Cell* 15:687–701). $O^r$ genomic DNAs were isolated from a library of sheared DNA, GC-tailed into the sep6 λ vector (Meyerowitz, F. M., and D. S. Hogness, 1982. Molecular organization of a Drosophila puff site that responds to ecdysone. *Cell* 28:165–176). One step in the chromosomal walk was taken using a cosmid library (prepared in collaboration with S. Gemeraad) of Sau IIIa partially digested $O^r$ DNA cloned into the cosmid p14B1 by the method of Ish-Horowicz and Burke (Ish-Horowicz, D., and J. F. Burke, 1982. Rapid and efficient cosmid cloning. *Nucleic Acids Res.* 9:2989–2998).

In Situ hybridization

In situ hybridization to polytene chromosomes was carried out with DNA probes that were nick-translated in the presence of $^3H$-labeled TTP (NEN), as described by Bonner and Pardue (Bonner, J. J., and M. L. Pardue, 1976. Ecdysone-stimulated RNA synthesis in imaginal discs of *Drosophila melanogaster*. Assay by in situ hybridization. *Chromosoma* 58:87–99), with the following modifications: Heat and RNAase treatments of the slides were omitted, and hybridization and washing were at 63° C. in 2XSSPE for 18 and 2 hours, respectively.

B. Identification of a 50 kb Region of Cloned Genomic DNA that Contains Sequences Homologous to Ecdysone-induced Transcripts Restriction fragments of the above genomic clones were tested for their ability to hybridize with each of two cDNA probes: one derived from the RNA in ecdysone-induced cells, and the other from the RNA in noninduced cells. Two such differential screens were carried out. In the first, genomic DNA covering the entire 350 kb walk was examined with cDNA probes synthesized with reverse transcriptase from an oligo(dT) primer annealed to poly(A)+ RNA. The poly(A)+ RNA was prepared from total inner tissues that were mass-isolated from late third instar larvae and incubated in the presence of ecdysone plus cycloheximide, or cycloheximide alone. (See Methods, below. Cycloheximide was included because higher levels of ecdysone-induced transcripts accumulate in its presence.)

Each of the $^{32}P$-labeled cDNA probes made from these two poly(A)+ RNAs was applied to one of two duplicate Southern blots that contained, in addition to the genomic fragments from the walk, a control DNA consisting of sequences from the ribosomal protein 49 gene (O'Connell, P., and M. Rosbash, 1984. Sequence, structure and codon preference of the Drosophila ribosomal protein 49 gene. *Nucleic Acids Res.* 12:5495–5513), which was used to normalize the hybridization intensities of the duplicate blots. This screen revealed sequences specific to ecdysone-induced RNAs only within the λcDm3522 genomic clone that is centered at approximately +220 kb on the molecular map.

Because the above probes will preferentially detect sequences near the 3' termini of the RNAs, particularly in the case of long transcripts, a second differential screen was carried out with cDNA probes primed with random hexamers (see Methods, below). This screen, which was restricted to the 135 kb of genomic DNA between +105 kb and +240 kb, revealed ecdysone-inducible sequences in fragments spread out over an ~50 kb region between +170 kb and +220 kb. This region represents the E75 gene.

Methods
Organ culture and RNA isolation

Late third instar $O^r$ larvae were harvested, washed in 0.7% NaCl, resuspended in Robb's phosphate-buffered saline (PBS) (Robb, J. A., 1968. Maintenance of imaginal discs of *Drosophila melanogaster* in chemically defined media. *J. Cell. Biol.* 41:876–885), preaerated with a blender, and passed through a set of rollers to extrude the organs. This "grindate" was filtered through a coarse Nitex screen to remove carcasses, and settled five times (3–5 minutes per settling) by gravity to remove floating and microscopic debris. Isolated tissues (primarily salivary glands, imaginal discs, gut, and Malphigian tubules) were cultured at 25° C. in plastic petri dishes in aerated Robb's PBS. β-ecdysone (Sigma) (0.2 μl/ml of 10 mg/ml) in ethanol and/or cycloheximide (2 μl/ml of 35 mM) in water was added to the appropriate cultures. Incubations in the presence of cycloheximide were for ~8 hours. Isolated tissues were homogenized in 10 volumes of 6M guanidine-HCl/0.6M sodium acetate (pH 5.2), centrifuged at 5000 g for 10 minutes to remove debris, and layered onto a 5.7M CaCl shelf, as described previously (Chirgwin, J. M., A. E. Przbyla, R. J. MacDonald, and W. J. Rutter, 1979. Isolation of biologically active ribonucleic acid from sources enriched in ribonuclease. *Biochemistry* 18:5294–5299). Poly(A)+ RNA was purified by oligo(dT) chromatography.

Southern blot analysis

Southern blots were performed on nitrocellulose, as described previously (Segraves, W. A., C. Louis, S. Tsubota, P. Schedl, J. M. Rawls, and B. P. Jarry, 1984. The rudimentary locus of *Drosophila melanogaster*. *J. Mol. Biol.* 175:1–17). cDNA probes were prepared by reverse transcription (AMV reverse transcriptase; Seikagaku) of 2 μg of poly(A)+ RNA with 700 ng of oligo(dT)$^{12-16}$ (Collaborative Research) or 15 μg of random hexamers (Pharmacia) in a 20 μl reaction mixture containing 80 mM Tris Cl (pH 8.3 at 42° C.), 10 mM MgCl$_2$, 100 mM KCl, 0.4 mM DTT, 0.25 mM each of dATP, dGTP, and dTTP, and 100 μCi of [$^{32}P$]dCTP (800 Ci/mole; Amersham). After incubation at 37° C. for 45 minutes, 80 μl of 10 mM EDTA and 2 μl of 5 N NaOH were added before incubation at 70° C. for 10 minutes to denature the products and hydrolyze the RNA. After the addition of 10 μl of 1M Tris Cl (pH 7.5) and 5 μl of 1N HCl, unincorporated label was removed by chromatography on Biogel P60.

C. The E75 Gene Contains Two Overlapping Transcription Units: E75A and E75B

Northern blot analysis of ecdysone-induced and noninduced RNAs, prepared as described above and hybridized with strand-specific DNA probes derived from cloned restriction fragments in the 60 kb region (+166 to 226 kb) containing the E75 gene, demonstrated that this gene produces two classes of ecdysone-inducible mRNAs, both derived from rightward transcription. The E75A class of mRNAs hybridized with probes from both the 5' (left) and 3' (right) ends of the 50 kb E75 gene. The E75B class hybridized only with probes from the 3' proximal 20 kb of the gene. These results suggest that the A and B classes of ecdysone-inducible RNAs are initiated by different promoters, located about 30 kb apart and that the two transcription units defined by these promoters overlap in the region downstream from the B promoter.

This suggestion was confirmed by analysis of the structure of cloned cDNAs from the E75A and E75B mRNAs. Approximately $10^6$ clones from an early pupal cDNA library (Poole, S. J., L. M. Kauvar, B. Drees, and T. Kornberg, 1985. The engrailed locus of Drosophila: Structural analysis of an embryonic transcript. *Cell* 40:37–40) were screened at low resolution with genomic DNA probes from the E75 gene region. The 116 cDNA clones identified by this screen were analyzed by restriction digestion and hybridization to a panel of probes derived from the 60 kb (+166 to +226 kb) region. One of the clones, λDm4925, was thereby selected as a representative of the E75A class of mRNAs, and another, λDm4745, as a representative of the E75B mRNA class.

The genomic regions homologous to these two cDNA clones were further localized by Southern blot analysis, and the nucleotide sequence of these regions and of both cDNA clones was determined. These sequences are given in Table 1, along with those derived from 5' and 3' terminal sequence determinations for each transcription unit. These data demonstrate that the 50 kb E75A transcription unit consists of six exons, labeled in 5' to 3' order: A0, A1, 2, 3, 4 and 5, of which exons A0 and A1 are specific to this unit, while the remaining four are shared with the 20 kb E75B transcription unit. Similarly, the E75B unit contains a specific exon, labeled B1, at its 5' end, which is located just upstream of the shared exon 2. Thus, the E75 gene consists of two transcription units, of which the shorter E75B unit occupies the 3' proximal 20 kb of the longer E75A unit.

TABLE 1

Sequences of the E75 exons and flanking DNA. The sequence is that of the C' genomic DNA, which was identical to that of the cDNAs, except for the T→G change indicated at position +2691. This change would convert a leucine to an arginine in the protein sequences. The Dm4925 cDNA extends from just 5' of the EcoRV site at +939 to +4267 in A. The Dm4745 cDNA extends from +804 in B to a point near the HindIII site at +4246 in A. (A) The E75 A exons and flanking DNA. The sequences of the A0, A1 and common exons 2–5 are interrupted by intron sequences (lowercase), which are limited to those near the splice sited and are in agreement with consensus sequences for donor (5') and acceptor (3') splice sites. Numbers at the right end of each line refer to the number of base pairs upstream of the E75 A initiation site if negative, positive numbers refer to positions in the E75 A mRNAs, continuing into the 3' flanking DNA. Numbers at the left end of each line refer to amino acid residues in the E75 A protein. The underlined 14 bp sequence at −159 to −172 exibits a 13/14 bp match to a sequence (CGTAGCGGGTCTC) found 47 bp upstream of the ecdysone-inducible E74 A transcription unit responsible for the early puff at 74EF. This sequence represents the proximal part of a 19 bp sequence in the E74 A promoter that binds the protein encoded by the D. melanogaster zeste gene. Another underlined sequence in the E75 A promoter at −74 to −82 is also found in the E75 B promoter, where it is part of a tandemly repeated octanucleotide (GAGAGAGC) located at −106 to −121 in B. This repeat matches the consensus sequence for the binding sites of the GAGA transcription factor which also binds to the E74 A promoter. Other underlined sequences represent, at −27 to −33, the best match to the TATA box consensus at an appropriate position, three AUG codons that are closely followed by in-frame stop codons in the 5'-leader sequence of the E75 mRNAs, and alternative polyadenylation-cleavage signals at 4591 and 5365 that are used by both E75 A and E75B mRNAs. (B) The B1 exon and its 5'-flanking DNA. The numbering at the right and left ends of the lines follows the same convention as in A. Exons 2–5 shown in A are also used in E75 B, but the amino acid residues and base pair numbers shown in A must be increased by 157 and 375, respectively, to apply to the E75 B protein and mRNA. The first ten nucleotides of the 136-nucleotide E75 B-intron linking the B1 exon to Exon 2 are gtaggttag, whereas the last ten are shown upstream of nucleotide 1178 in A. The underlined sequences represent, in order, the region of homology to a sequence upstream of E75 A, noted above, the best match to the TATA box consensus at −21 to −27, and three AUG codons followed by in-frame stop codons in the 5' leader of the E75 B mRNA.

Panel 1

A

ACTTACTAGTGAAAAACATGATAATAAACAACTTGCCAAAAAAAATCCAATGAAATTGACA

CTTATGTTAAAAAAATAGGTGAGATTGTAACCGTTGATGTACACTTACGAAGTACGTAACAAGTTCATGA

−141
ACTGATTTCGTGAGCAGGTCTCTCCATAATCGCCGTATCTGTGGGATCGCGCGCTCCTGCTCGCACTCGC

TGGGTGGATGGCAGCACATGTTCGAAGTGCGAGAGAGTGCAAAGCGGAGAGCGCCGACGTCGACGCCGAA

+1
AAAACTGAACAAGATCCGCCGCGAATGTTGATTTTCCTTTCATTGACTAACTGCCACTCGCAGCGCGCAG
                                  └─→ mRNA start site

ATCGTCGGCTCCGCTTGTTCCGTTCCGTTCGTTTCGTTTCGTTTCGTTCGATCTACTTCGAGTCGCGAGT

TTTAAGCAGTGTAGTGAGTGCCCCGTGAAAAGGATAACCCAAAAAGTGATTTCTACTATTTTCCAATAGT

+211
TTTTATCAGTGTGAAGAAAACATGTAAACTTGGCTCAAAAAGGGCTTTAAAAGATACAAAGCTTCAATGC

TABLE 1-continued

GAAGGAT AAAAT AAT AT CGCACCAGT GCTT CAAAAACCAAAACT <u>AT</u>GCCT AAGGCT GGAAAT TT AAATT A

AAAT T T T T T T AAT AAAT AT T CC AAAAAT AT T GCCCCT GAAAAGT GT T GAT AAACCCCCAACCGAGCAAA

```
380
ATG TTA ATG TCC GCG GAC AGT TCA GAT AGC GCC AAG ACT TCT GTG ATC TGC AGC
MET Leu MET Ser Ala Asp Ser Ser Asp Ser Ala Lys Thr Ser Val Ile Cys Ser
1

ACG GTG AGT GCC AGC ATG CTA GCA CCA CCA GCT CCA GAA CAG CCC AGC ACC ACA
Thr Val Ser Ala Ser MET Leu Lal Pro Pro Ala Pro Glu Gln Pro Ser Thr Thr

GCA CCA CCC ATT TTG GGG GTA ACA GGT CGA TCT CAC CTG GAA AAT GCC CTG AAA
Ala Pro Pro Ile Leu Gly Val Thr Gly Arg Ser His Leu Glu Asn Ala Leu Lys
                                                                      54

542
CTA CCG CCA AAC ACA AGT GTT TCG GCT TAC TAC CAG CAC AAC AGC AAG CTG GGC
Leu Pro Pro Asn Thr Ser Val Ser Ala Tyr Tyr Gln His Asn Ser Lys Leu Gly

ATG GGC CAG AAT TAC AAT CCG GAA TTC AGG AGC CTG GTA GCA CCT GTC ACA GAT
MET Gly Gln Asn Tyr Asn Pro Glu Phe Arg Ser Leu Val Ala Pro Val Thr Asp

CTG GAT ACT GTG CCA CCC ACA GGT GTG ACC ATG GCG AGT TCT TCG AAT TCT CCC
Leu Asp Thr Val Pro Pro Thr Gly Val Thr Met Ala Ser Ser Ser Asn Ser Pro
                                                                       108

AAC TCC TCC GTC AAG CTG CCC CAC AGC CGC GTG ATC TTT GTC AGC AAA TCG AGT
Asn Ser Ser Val Lys Leu Pro His Ser Gly Val Ile Phe Val Ser Lys Ser Ser

GCC GTC AGC ACC ACC GAT GGT CCC ACT GCA GTG TTG CAA CAG CAG CAG CCG CAG
Ala Val Ser Thr Thr Asp Gly Pro Thr Ala Val Leu Gln Gln Gln Gln Pro Gln

812
CAG CAA ATG CCC CAG CAC TTC GAG TCC CTG CCC CAC CAC CAC CCC CAG CAG GAA
Gln Gln MET Pro Gln His Phe Glu Ser Leu Pro His His His Pro Gln Gln Glu
                                                                      162

CAC CAG CCA CAG CAG CAG CAG CAA CAA CAT CAC CTT CAG CAC CAC CCA CAT CCA
His Gln Pro Gln Gln Gln Gln Gln Gln His His Leu Gln His His Pro His Pro

CAT GTG ATG TAT CCG CAC GGA TAT CAG CAG GCC AAT CTG CAC CAC TCG GGT GGT
His Val MET Tyr Pro His Gly Tyr Gln Gln Ala Asn Leu His His Ser Gly Gly

ATT GCT GTG GTT CCG GCG GAT TCG CGT CCC CAG ACT CCC GAG TAC ATC AAG TCC
Ile Ala Val Val Pro Ala Asp Ser Arg Pro Gln Thr Pro Glu Tyr Ile Lys Ser
                                                                       216

TAC CCA GTT ATG GAT ACA ACT GTG GCT AGT TCG GTA AAG GGG GAA CCA GAA CTC
Tyr Pro Val MET Asp Thr Thr Val Ala Ser Ser Val Lys Gly Glu Pro Glu Leu
```

GTGAGTTGTG .. intron 1 .. TTCTTTGCAG

```
1082
AAC ATA GAA TTC GAT GGC ACC ACA GTG CTG TGC CGC GTT TGC CGG GAT AAG GCC
Asn Ile Glu Phe Asp Gly Thr Thr Val Leu Cys Arg Val Cys Gly Asp Lys Ala
```

GTAAGTTCGT .. intron 2 .. ATCGTTTCAG

```
TCC GGT TTC CAT TAC GGC GTG CAT TCC TGC GAG GGT TGC AAG GGA TTC TTC CGC
Ser Gly Phe His Tyr Gly Val His Ser Cys Glu Gly Cys Lys Gly Phe Phe Arg
                                                                       270

CGC TCC ATC CAG CAA AAG ATC CAG TAT CGC CCG TGC ACC AAG AAT CAG CAG TGC
Arg Ser Ile Gln Gln Lys Ile Gln Tyr Arg Pro Cys Thr Lys Asn Gln Gln Cys

AGC ATT CTG CGC ATC AAT CGC AAT CGT TGT CAA TAT TGC CGC CTG AAA AAG TGC
Ser Ile Leu Arg Ile Asn Arg Asn Arg Cys Gln Tyr Cys Arg Leu Lys Lys Cys
```

GTGAGTACCT .. intron 3 .. CCAATTGCAG

```
ATT GCC GTG GGC ATG AGT CGC GAT GCT GTG CGT TTT GGA CGC GTG CCG AAG CGC
Ile Ala Val Gly MET Ser Arg Asp Ala Val Arg Phe Gly Arg Val Pro Lys Arg
                                                                       324
```

TABLE 1-continued

```
1352
GAA AAG GCG CGT ATC CTG GCG GCC ATG CAA CAG AGC ACC CAG AAT CGC GGC CAG
Glu Lys Ala Arg Ile Leu Ala Ala MET Gln Gln Ser Thr Gln Asn Arg Gly Gln

CAG CGA GCC CTC GCC ACC GAG CTG GAT GAC CAG CCA CGC CTC CTC GCC GCC GTG
Gln Arg Ala Leu Ala Thr Glu Leu Asp Asp Gln Pro Arg Leu Leu Ala Ala Val

CTG CGC GCC CAC CTC GAG ACC TGT GAG TTC ACC AAG GAG AAG GTC TCG GCG ATG
Leu Arg Ala His Leu Glu Thr Cys Glu Phe Thr Lys Glu Lys Val Ser Ala MET
                                                                    378
```

GTAAGTCTCA..intron 4..ATTTCTTCAG

```
CGG CAG CGG GCG CGG GAT TGC CCC TCC TAC TCC ATG CCC ACA CTT CTG GCC TGT
Arg Gln Arg Ala Arg Asp Cys Pro Ser Tyr Ser MET Pro Thr Leu Leu Ala Cys

CCG CTG AAC CCC GCC CCT GAA CTG CAA TCG GAG CAG GAG TTC TCG CAG CGT TTC
Pro Leu Asn Pro Ala Pro Glu Leu Gln Ser Glu Gln Glu Phe Ser Gln Arg Phe

1622
GCC CAC GTA ATT CGC GGC GTG ATC GAC TTT GCC GGC ATG ATT CCC GGC TTC CAG
Ala His Val Ile Arg Gly Val Ile Asp Phe Ala Gly MET Ile Pro Gly Phe Gln
                                                                    432

CTG CTC ACC CAG GAC GAT AAG TTC ACG CTC CTG AAG GCG GGA CTC TTC GAC GCC
Leu Leu Thr Gln Asp Asp Lys Phe Thr Leu Leu Lys Ala Gly Leu Phe Asp Ala

CTG TTT GTG CGC CTG ATC TGC ATG TTT GAC TCG TCG ATA AAC TCA ATC ATC TGT
Leu Phe Val Arg Leu Ile Cys MET Phe Asp Ser Ser Ile Asn Ser Ile Ile Cys

CTA AAT GGC CAG GTG ATG CGA CGG GAT GCG ATC CAG AAC GGA GCC AAT GCC CGC
Leu Asn Gly Gln Val MET Arg Arg Asp Ala Ile Gln Asn Gly Ala Asn Ala Arg
                                                                    486

TTC CTG GTG GAC TCC ACC TTC AAT TTC GCG GAG CGC ATG AAC TCG ATG AAC CTG
Phe Leu Val Asp Ser Thr Phe Asn Phe Ala Glu Arg MET Asn Ser MET Asn Leu

1892
ACA GAT GCC GAG ATA GGC CTG TTC TGC GCC ATC GTT CTG ATT ACG CCG GAT CGC
Thr Asp Ala Glu Ile Gly Leu Phe Cys Ala Ile Val Leu Ile Thr Pro Asp Arg

CCC GGT TTG CGC AAC CTG GAG CTG ATC GAG AAG ATG TAC TCG CGA CTC AAG GGC
Pro Gly Leu Arg Asn Leu Glu Leu Ile Glu Lys MET Tyr Ser Arg Leu Lys Gly
                                                                    540

TGC CTG CAG TAC ATT GTC GCC CAG AAT AGG CCC GAT CAG CCC GAG TTC CTG GCC
Cys Leu Gln Tyr Ile Val Ala Gln Asn Arg Pro Asp Gln Pro Glu Phe Leu Ala

AAG TTG CTG GAG ACG ATG CCC GAT CTG CGC ACC CTG AGC ACC CTG CAC ACC GAG
Lys Leu Leu Glu Thr MET Pro Asp Leu Arg Thr Leu Ser Thr Leu His Thr Glu

AAA CTG GTA GTT TTC CGC ACC GAG CAC AAG GAG CTG CTG CGC CAG CAG ATG TGG
Lys Leu Val Val Phe Arg Thr Glu His Lys Glu Leu Leu Arg Gln Gln MET Trp
                                                                    594

2162
TCC ATG GAG GAC GGC AAC AAC AGC GAT GGC CAG CAG AAC AAG TCG CCC TCG GGC
Ser MET Glu Asp Gly Asn Asn Ser Asp Gly Gln Gln Asn Lys Ser Pro Ser Gly

AGC TGG GCG GAT GCC ATG GAC GTG GAG GCG GCC AAG AGT CCG CTT GGC TCG GTA
Ser Trp Ala Asp Ala MET Asp Val Glu Ala Ala Lys Ser Pro Leu Gly Ser Val

TCG AGC ACT GAG TCC GCC GAC CTG GAC TAC GGC AGT CCG AGC AGT TCG CAG CCA
Ser Ser Thr Glu Ser Ala Asp Leu Asp Tyr Gly Ser Pro Ser Ser Ser Gln Pro
                                                                    648

CAG GGC GTG TCT CTG CCC TCG CCG CCT CAG CAA CAG CCC TCG GCT CTG GCC AGC
Gln Gly Val Ser Leu Pro Ser Pro Pro Gln Gln Gln Pro Ser Ala Leu Ala Ser

TCG GCT CCT CTG CTG GCG GCC ACC CTC TCC GGA GGA TGT CCC CTG CGC AAC CGG
Ser Ala Pro Leu Leu Ala Ala Thr Leu Ser Gly Gly Cys Pro Leu Arg Asn Arg

2432
GCC AAT TCC GGC TCC AGC GGT GAC TCC GGA GCA GCT GAG ATG GAT ATC GTT GGC
Ala Asn Ser Gly Ser Ser Gly Asp Ser Gly Ala Ala Glu MET Asp Ile Val Gly
                                                                    702

TCG CAC GCA CAT CTC ACC CAG AAC GGG CTG ACA ATC ACG CCG ATT GTG CGA CAC
Ser His Ala His Leu Thr Gln Asn Gly Leu Thr Ile Thr Pro Ile Val Arg His
```

TABLE 1-continued

GTAGTATCTT..intron 5..TTTCTTACAG

| CAG | CAG | CAG | CAA | CAA | CAG | CAG | CAG | CAG | ATC | GGA | ATA | CTC | AAT | AAT | GCG | CAT | TCC |
|---|---|---|---|---|---|---|---|---|---|---|---|---|---|---|---|---|---|
| Gln | Gln | Gln | Gln | Gln | Gln | Gln | Gln | Gln | Ile | Gly | Ile | Leu | Asn | Asn | Ala | His | Ser |

| CGC | AAC | TTG | AAT | GGG | GGA | CAC | GCG | ATG | TGC | CAG | CAA | CAG | CAG | CAG | CAC | CCA | CAA |
|---|---|---|---|---|---|---|---|---|---|---|---|---|---|---|---|---|---|
| Arg | Asn | Leu | Asn | Gly | Gly | His | Ala | MET | Cys | Gln | Gln | Gln | Gln | Gln | His | Pro | Gln 756 |

G (Dm4925)

| CTG | CAC | CAC | CAC | TTG | ACA | GCC | GGA | GCT | GCC | CGC | TAC | AGA | AAG | CTA | GAT | TCG | CCC |
|---|---|---|---|---|---|---|---|---|---|---|---|---|---|---|---|---|---|
| Leu | His | His | His | Leu | Thr | Ala | Gly | Ala | Ala | Arg | Tyr | Arg | Lys | Leu Arg | Asp | Ser | Pro |

2702
| ACG | GAT | TCG | GGC | ATT | GAG | TCG | GGC | AAC | GAG | AAG | AAC | GAG | TGC | AAG | GCG | GTG | AGT |
|---|---|---|---|---|---|---|---|---|---|---|---|---|---|---|---|---|---|
| Thr | Asp | Ser | Gly | Ile | Glu | Ser | Gly | Asn | Glu | Lys | Asn | Glu | Cys | Lys | Ala | Val | Ser |

| TCG | GGG | GGA | AGT | TCC | TCG | TGC | TCC | AGT | CCG | CGT | TCC | AGT | GTG | GAT | GAT | GCG | CTG |
|---|---|---|---|---|---|---|---|---|---|---|---|---|---|---|---|---|---|
| Ser | Gly | Gly | Ser | Ser | Ser | Cys | Ser | Ser | Pro | Arg | Ser | Ser | Val | Asp | Asp | Ala | Leu 810 |

| GAC | TGC | AGC | GAT | GCC | GCC | GCC | AAT | CAC | AAT | CAG | GTG | GTG | CAG | CAT | CCG | CAG | CTG |
|---|---|---|---|---|---|---|---|---|---|---|---|---|---|---|---|---|---|
| Asp | Cys | Ser | Asp | Ala | Ala | Ala | Asn | His | Asn | Gln | Val | Val | Gln | His | Pro | Gln | Leu |

| AGT | GTG | GTG | TCC | GTG | TCA | CCA | GTT | CGC | TCG | CCC | CAG | CCC | TCC | ACC | AGC | AGC | CAT |
|---|---|---|---|---|---|---|---|---|---|---|---|---|---|---|---|---|---|
| Ser | Val | Val | Ser | Val | Ser | Pro | Val | Arg | Ser | Pro | Gln | Pro | Ser | Thr | Ser | Ser | His |

| CTG | AAG | CGA | CAG | ATT | GTG | GAG | GAT | ATG | CCC | GTG | CTG | AAG | CGC | GTG | CTG | CAG | GCT |
|---|---|---|---|---|---|---|---|---|---|---|---|---|---|---|---|---|---|
| Leu | Lys | Arg | Gln | Ile | Val | Glu | Asp | MET | Pro | Val | Leu | Lys | Arg | Val | Leu | Gln | Ala 864 |

2972
| CCC | CCT | CTG | TAC | GAT | ACC | AAC | TCG | CTG | ATG | GAC | GAG | GCC | TAC | AAG | CCG | CAC | AAG |
|---|---|---|---|---|---|---|---|---|---|---|---|---|---|---|---|---|---|
| Pro | Pro | Leu | Tyr | Asp | Thr | Asn | Ser | Leu | MET | Asp | Glu | Ala | Tyr | Lys | Pro | His | Lys |

| AAA | TTC | CGG | GCC | CTG | CGG | CAT | CGC | GAG | TTC | GAG | ACC | GCC | GAG | GCG | GAT | GCC | AGC |
|---|---|---|---|---|---|---|---|---|---|---|---|---|---|---|---|---|---|
| Lys | Phe | Arg | Ala | Leu | Arg | His | Arg | Glu | Phe | Glu | Thr | Ala | Glu | Ala | Asp | Ala | Ser |

| AGT | TCC | ACT | TCC | GGC | TCG | AAC | AGC | CTG | AGT | GCC | GGC | AGT | CCG | CGG | CAG | AGC | CCA |
|---|---|---|---|---|---|---|---|---|---|---|---|---|---|---|---|---|---|
| Ser | Ser | Thr | Ser | Gly | Ser | Asn | Ser | Leu | Ser | Ala | Gly | Ser | Pro | Arg | Gln | Ser | Pro 918 |

| GTC | CCG | AAC | AGT | GTG | GCC | ACG | CCC | CCG | CCA | TCG | GCG | GCC | AGC | GCC | GCC | GCA | GGT |
|---|---|---|---|---|---|---|---|---|---|---|---|---|---|---|---|---|---|
| Val | Pro | Asn | Ser | Val | Ala | Thr | Pro | Pro | Pro | Ser | Ala | Ala | Ser | Ala | Ala | Ala | Gly |

| AAT | CCC | GCC | CAG | AGC | CAG | CTG | CAC | ATG | CAC | CTG | ACC | CGC | AGC | AGC | CCC | AAG | GCC |
|---|---|---|---|---|---|---|---|---|---|---|---|---|---|---|---|---|---|
| Asn | Pro | Ala | Gln | Ser | Gln | Leu | His | MET | His | Leu | Thr | Arg | Ser | Ser | Pro | Lys | Ala |

3242
| TCG | ATG | GCC | AGC | TCG | CAC | TCG | GTG | CTG | GCC | AAG | TCT | CTC | ATG | GCC | GAG | CCG | CGC |
|---|---|---|---|---|---|---|---|---|---|---|---|---|---|---|---|---|---|
| Ser | MET | Ala | Ser | Ser | His | Ser | Val | Leu | Ala | Lys | Ser | Leu | MET | Ala | Glu | Pro | Arg 972 |

| ATG | ACG | CCC | GAG | CAG | ATG | AAG | CGC | AGC | GAT | ATT | ATC | CAA | AAC | TAC | TTG | AAG | CGC |
|---|---|---|---|---|---|---|---|---|---|---|---|---|---|---|---|---|---|
| MET | Thr | Pro | Glu | Gln | MET | Lys | Arg | Ser | Asp | Ile | Ile | Gln | Asn | Tyr | Leu | Lys | Arg |

| GAG | AAC | AGC | ACA | GCA | GCC | AGC | AGC | ACC | ACC | AAT | GGC | GTG | GGC | AAC | CGC | AGT | CCC |
|---|---|---|---|---|---|---|---|---|---|---|---|---|---|---|---|---|---|
| Glu | Asn | Ser | Thr | Ala | Ala | Ser | Ser | Thr | Thr | Asn | Gly | Val | Gly | Asn | Arg | Ser | Pro |

| AGC | AGC | AGC | TCC | ACA | CCG | CCG | CCG | TCG | GCG | GTC | CAG | AAT | CAG | CAG | CGT | TGG | GGC |
|---|---|---|---|---|---|---|---|---|---|---|---|---|---|---|---|---|---|
| Ser | Ser | Ser | Ser | Thr | Pro | Pro | Pro | Ser | Ala | Val | Gln | Asn | Gln | Gln | Arg | Trp | Gly 1026 |

| AGC | AGC | TCG | GTG | ATC | ACC | ACC | ACC | TGC | CAG | CAG | AGC | CAG | CAG | TCC | GTG | TCG | CCG |
|---|---|---|---|---|---|---|---|---|---|---|---|---|---|---|---|---|---|
| Ser | Ser | Ser | Val | Ile | Thr | Thr | Thr | Cys | Gln | Gln | Arg | Gln | Gln | Ser | Val | Ser | Pro |

3512
| CAC | AGC | AAC | GGT | TCC | AGC | TCC | AGT | TCG | AGC | TCT | AGC | TCC | AGC | TCC | AGT | TCG | TCA |
|---|---|---|---|---|---|---|---|---|---|---|---|---|---|---|---|---|---|
| His | Ser | Asn | Gly | Ser | Ser | Ser | Ser | Ser | Ser | Ser | Ser | Ser | Ser | Ser | Ser | Ser | Ser |

| TCC | TCC | TCC | ACA | TCC | TCC | AAC | TGC | AGC | TCC | AGC | TCG | GCC | AGC | AGC | TGC | CAG | TAT |
|---|---|---|---|---|---|---|---|---|---|---|---|---|---|---|---|---|---|
| Ser | Ser | Ser | Thr | Ser | Ser | Asn | Cys | Ser | Ser | Ser | Ser | Ala | Ser | Ser | Cys | Gln | Tyr 1080 |

| TTC | CAG | TCG | CCG | CAC | TCC | ACC | AGC | AAC | GGC | ACC | AGT | GCA | CCG | GCG | AGC | TCC | AGT |
|---|---|---|---|---|---|---|---|---|---|---|---|---|---|---|---|---|---|
| Phe | Gln | Ser | Pro | His | Ser | Thr | Ser | Asn | Gly | Thr | Ser | Ala | Pro | Ala | Ser | Ser | Ser |

| TCG | GGA | TCG | AAC | AGC | GCC | ACG | CCC | CTG | CTG | GAA | CTG | CAG | GTG | GAC | ATT | GCT | GAC |
|---|---|---|---|---|---|---|---|---|---|---|---|---|---|---|---|---|---|
| Ser | Gly | Ser | Asn | Ser | Ala | Thr | Pro | Leu | Leu | Glu | Leu | Gln | Val | Asp | Ile | Ala | Asp |

TABLE 1-continued

| | | | | | | | | | | | | | | | | |
|---|---|---|---|---|---|---|---|---|---|---|---|---|---|---|---|---|
|TCG|GCG|CAG|CCT|CTC|AAT|TTG|TCC|AAG|AAA|TCG|CCC|ACG|CCG|CCG|CCC|AGC|AAG|
|Ser|Ala|Gln|Pro|Leu|Asn|Leu|Ser|Lys|Lys|Ser|Pro|Thr|Pro|Pro|Pro|Ser|Lys 1134|

3782
CTG CAC GCT CTG GTG GCC GCC GCC AAT GCC GTT CAA AGG TAT CCC ACA TTG TCC
Leu His Ala Leu Val Ala Ala Ala Asn Ala Val Gln Arg Tyr Pro Thr Leu Ser

GCC GAC GTC ACA GTG ACA GCC TCC AAT GGC GGG TCC TCC GTC GGC GGC GGC GAG
Ala Asp Val Thr Val Thr Ala Ser Asn Gly Gly Ser Ser Val Gly Gly Gly Glu

TCC GGC CGC CAG CAG CAG TCC GCC GGC GAG TGT CGG CTC CCC CAA TCC GGG CCT
Ser Gly Arg Gln Gln Gln Ser Ala Gly Glu Cys Gly Leu Pro Gln Ser Gly Pro
                                                                      1186

GAG CGC CGC CGT GCA CAA GGT AAT GCT GGA GGC GTA AGA GCG GGA GGA GGT AGG
Glu Arg Arg Arg Ala Gln Gly Asn Ala Gly Gly Val Arg Ala Gly Gly Gly Arg

TGG TTT TAC GCG GAG AAG TGG GAG AGA CAG AGA CTG GGA GTG GCA GTT CAG CGA
Trp Phe Tyr Ala Glu Lys Trp Glu Arg Gln Arg Leu Gly Val Ala Val Gln Arg

4052
AGC AGG AAG CAG GAT CAC TTG GAG CGG CGG GAG TTG AAT TAA.
Ser Arg Lys Gln Asp His Leu Glu Arg Arg Glu Leu Asn
                                             1237

ATTATTTTACCATTTAATTGAGACGTGTACAAAGTTTGAAAGCAAAACCAACATGCATGCAATTTAAAAC

TAATATTTAAAGCAACAACAAACAAAACAACTACAAGTTATTAATTTAAAAAACAAACAAACAAACAAAC

4234
AACAAAAAACCCAAGCTTGAATGGTATTACAAAAGAAAAAGAAAAACAGAAAAAATATAAATATATTTTA

GCAGTTAAACTTTAACGTAGCAAGAAACCAACAAACCCAAGGCAGCGCTCTGATTTCGCATTAACTTTTC

4374
TTCAGCTGCTACCGAAAACGCCCCTCACCTCCCCCCCACCCAACCCTTCCTCCACACACCAACCGTCTTT

CGACCCCTGATTGTTTTATAAGTTTTAAGCTCTTGTTGTACATATTAATTACGTTTATTGGTAACTATGT

4514
TTAGCGCTTTAGTTGTAGTTGGAGCAAAACTACTTTGCTTTTTTGGATGTTTTTTGAAAAAACTGCAAAT

TATTATT<u>ATT</u>AAATTTTTAAATACCTAAAAACAAAACAATGTGTGTGAAATTTTTTATTGTGCGATCTCC
                              └→ poly A site cDm4927 and cDm4928

4654
AAGCAGAATGAAGTGCAGTTTGCAACAAATTTTAACTACGATTAAGTTGATAACGATTCATTTTTTATGA

ATTTAACTAATTTTATGAATTTGTTATAGTTTTCCACCCTTCTATAGATCTTCTATCTGATCATCTAGCT

4794
ACCCGTATTCCTGATTTCTCCTTTGGCACAAAGCTCTTCTCTATGCTAAAGAATCAAGTGGAATAAATAT

TGTTTTCTAATTTTAAAACTACCACAAAAATACGATTAAAATATACACGAAGTAATGAAAATCAAACAAA

4934
ATGCTTAAAGTTTTAGCAGCAAGCAGTAAAACGACGATGAAGAAGAGAAACCCAACGTTAAATATATCTG

TTGTGTACATAGTTAAATGTTAAATTAAACACAAAAACATATTTAAAGTACATATAAATACACATAATTA

5074
TTAATGAAGAAACCTATGCTTAAAAGATTCAATGTTTGATTGGCATCTTAGAAAACCAAGCGAAAAATAC

AAAAAAAAATCAACAAACAAAAATTATGATATATTATTTAAAAGTAAAGTATACATTTACATTACAGAAA

5214
AACAAAAGAGAAAACTTGCGGTAGCAACAAAACTATTATATTAATTACATTTTAATTATGCTGTACTATT

ATGATTATTAATTATTATGATTAATTAATTACGATTTTTATGCTTAGACAAACCAACAAAAAACAAATAT

5354
GCAAAAACC<u>ATT</u>AAAAAAAAAAACAAAAAACAAGCAAAAAAT
        └→ putative polyadenylation signal for long transcripts

TABLE 1-continued

Panel 2

B

CGACGCGTTTGGAGTGAACGTCCTCAGTTGGCACACAAAAACAAAAACACAAAACGACAGCAACAACATC

−141
GGTGGGGGGAGTACGAGCGGGATGGGGGTAATGGGGGGCACCGGGGGAGTGGAGGCC<u>GAGAGAGCCAGAG</u>

<u>AGCGA</u>CCCGAAGCAACACAACACCAACACGAGGCCCAAAAAGACACTTCGGCTGGGTTCAGCTCGTGTTG

+1
CTCTGGGTCGT<u>TTTGT</u>ATTGCTGGTGGACGCTGCTTTCATTCGCAAATTGCTCGTCGTTGGCAGCGGTTG
↳ mRNA start site

TGCAGAGCAAGAAAAGCGCGCGAAAAACCAAGCAAAAAATTAATACAGCTGGATCAAGCGAAAGAGATAG

AGAGCAGAGTCAACAGCAACAA<u>AT</u>GTTCAATAGCAA<u>AT</u>GATATCGCATATTTTTGTTGGTGCCAGTGAAG

+211
TGAGATCAAAGTGAAGTGTGCA<u>AT</u>GTTCCTTATTAGCAAATCGTAGAGCAACCAACAATCGAGAGTTCAA

```
                                                                  284
      GTGTCATTTCGAAGCCAAAAAGCAAAATCTCTAATTCAAAT ATG GTT TGT GCA ATG CAA
                                                MET Val Cys Ala MET Gln
                                                 1
```

```
302
GAG GTT GCT GCT GTG CAG CAT CAG CAG CAG CAA CAG CAA CTC CAG TTG CCC CAG
Glu Val Lal Ala Val Gln His Gln Gln Gln Gln Gln Gln Leu Gln Leu Pro Gln
                                                                        24

CAG CAA CAG CAG CAG CAG CAG ACA ACA CAG CAG CAA CAT GCA ACA ACG ATA GTG
Gln Gln Hln Gln Gln Gln Gln Thr Thr Gln Gln Gln His Ala Thr Thr Ile Val

CTG CTG ACG GGC AAT GGC GGC GGT AAT CTG CAC ATT GTC GCC ACA CCG CAA CAG
Leu Leu Thr Gly Asn Gly Gly Gly Asn Leu His Ile Val Ala Thr Pro Gln Gln

CAT CAG CCG ATG CAT CAG CTC CAC CAT CAG CAT CAG CAT CAG CAT CAG CAC CAG
His Gln Pro MET His Gln Leu His His Gln His Gln His Gln His Gln His Gln
                                                                        78

CAG CAG GCC AAG AGC CAA CAG CTG AAG CAA CAA CAC TCG GCG CTG GTC AAG TTG
Gln Gln Ala Lys Ser Gln Gln Leu Lys Gln Gln His Ser Ala Leu Val Lys Leu

572
CTG GAG TCG GCG CCC ATC AAG CAG CAA CAG CAG ACG CCC AAG CAA ATT GTT TAC
Leu Glu Ser Ala Pro Ile Lys Gln Gln Gln Gln Thr Pro Lys Gln Ile Val Tyr

CTG CAG CAG CAG CAG CAG CAA CCG CAA CGC AAA AGA CTG AAA AAC GAA GCA GCA
Leu Gln Gln Gln Gln Gln Gln Pro Gln Arg Lys Arg Leu Lys Asn Glu Ala Ala
                                                                       132

ATC GTA CAA CAG CAA CAA CAA ACA CCT GCA ACA CTA GTA AAG ACA ACA ACC ACC
Ile Val Gln Gln Gln Gln Gln Thr Pro Ala Thr Leu Val Lys Thr Thr Thr Thr

AGC AAC AGC AAC AGC AAC AAC ACC CAG ACA ACA AAT AGT ATT AGT CAG CAG CAA
Ser Asn Ser Asn Ser Asn Asn Thr Gln Thr Thr Asn Ser Ile Ser Gln Gln Gln

CAG CAG CAT CAG ATT GTG TTG CAG CAC CAG CAG CCA GCC GCG GCA GCA ACA CCA
Gln Gln His Gln Ile Val Leu Gln His Gln Gln Pro Ala Ala Ala Ala Thr Pro
                                                                       186

842
AAG CCA TGT GCC GAT CTG AGC GCC AAA AAT GAC AGC GAG TCG GGC ATC GAC GAG
Lys Pro Cys Ala Asp Leu Ser Ala Lys Asn Asp Ser Glu Ser Gly Ile Asp Glu

GAC TGC CCC AAC AGC GAT GAG GAT TGC CCC AAT GCC AAC CCG GCG GGC ACA TCG
Asp Cys Pro Asn Ser Asp Glu Asp Cys Pro Asn Ala Asn Pro Ala Gly Thr Ser

CTC GAG GAC AGC AGC TAC GAG CAG TAT CAG TGC CCC TGG AAG AAG ATA CGC TAT
Leu Glu Asp Ser Ser Tyr Glu Gln Tyr Gln Cys Pro Trp Lys Lys Ile Arg Tyr
                                                                       240

GCG CGT GAG CTC CTC AAG CAG CGC GAG TTG GAG CAG CAG CAG ACC ACC GGA GGC
Ala Arg Glu Leu Leu Lys Gln Arg Glu Leu Glu Gln Gln Gln Thr Thr Gly Gly

AGC AAC GCG CAG CAG CAA GTC GAG GCG AAG CCA GCT GCA ATA CCC ACC AGC AAC
Ser Asn Ala Gln Gln Gln Val Glu Ala Lys Pro Ala Ala Ile Pro Thr Ser Asn
```

TABLE 1-continued

```
1112
ATC AAG CAG CTG CAC TGT GAT AGT CCC TTT TCG GCG CAG ACC CAC AAG GAA ATC
Ile Lys Gln Leu His Cys Asp Ser Pro Phe Ser Ala Gln Thr His Lys Glu Ile
                                                                      294

GCC AAT CTC CTG CGC CAA CAG TCC CAG CAA CAA CAG GTT GTG GCC ACG CAG CAG
Ala Asn Leu Leu Arg Gln Gln Ser Gln Gln Gln Gln Val Val Ala Thr Gln Gln

CAG CAG CAA CAG CAG CAG CAG CAC CAG CAC CAG CAA CAA CGA AGG GAT AGC TCC
Gln Gln Gln Gln Gln Gln Gln His Gln His Gln Gln Gln Arg Arg Asp Ser Ser

GAC AGC AAC TGC TCG CTG ATG AGC AAC TCG AGC AAC TCC AGT GCG GGC AAT TGT
Asp Ser Asn Cys Ser Leu MET Ser Asn Ser Ser Asn Ser Ser Ala Gly Asn Cys
                                                                      348

TGC ACC TGC AAC GCT GGC GAC GAC CAG CAG CTG GAG GAG ATG GAC GAG GCC CAC
Cys Thr Cys Asn Ala Gly Asp Asp Gln Gln Leu Glu Glu MET Asp Glu Ala His

1382
GAT TCG GGC TGC GAC GAT GAA CTT TGC GAG CAG CAT CAC CAG CGA CTG GAC TCC
Asp Ser Gly Cys Asp Asp Glu Leu Cys Glu Gln His His Gln Arg Leu Asp Ser

TCC CAA CTG AAT TAC CTG TGC CAG AAG TTC GAT GAG AAA CTG GAC ACG GCG CTG
Ser Gln Leu Asn Tyr Leu Cys Gln Lys Phe Asp Glu Lys Leu Asp Thr Ala Leu
                                                                      402

AGC AAC AGC AGC GCC AAC ACG GGG AGG AAC ACG CCA GCT GTA ACA GCT AAC GAA
Ser Asn Ser Ser Ala Asn Thr Gly Arg Asn Thr Pro Ala Val Thr Ala Asn Glu

1544
GAT GCC GAT gtaggtttag
Asp Ala Asp
```

Panel 3

A

```
         ACTTACTAGTGAAAAACATGATAATAAACAACTTGCCAAAAAAAATCCAATGAAATTGACA

CTTATGTTAAAAAAATAGGTGAGATTGTAACCGTTGATGTACACTTACGAAGTACGTAACAAGTTCATGA
                                     -141
ACTGATTTCGTGAGCAGGTCTCTCCATAATCGCCGTATCTGTGGGATCGCGCGCTCCTGCTCGCACTCGC

TGGGTGGATGGCAGCACATGTTCGAAGTGCGAGAGAGTGCAAAGCGGAGAGCGCCGACGTCGACGCCGAA
                                               +1
AAAACTGAACAAGATCCGCCGCGAATGTTGATTTTCCTTTCATTGACTAACTGCCACTCGCAGCGCGCAG
                     └──> mRNA start site

ATCGTCGGCTCCGCTTGTTCCGTTCCGTTCGTTTCGTTTCGTTTCGTTCGATCTACTTCGAGTCGCGAGT

TTTAAGCAGTGTAGTGAGTGCCCCGTGAAAAGGATAACCCAAAAAGTGATTTCTACTATTTTCCAATAGT
                                        +211
TTTTATCAGTGTGAAGAAAACATGTAAACTTGGCTCAAAAAGGGCTTTAAAAGATACAAAGCTTCAATGC

GAAGGATAAAATAATATCGCACCAGTGCTTCAAAAACCAAAACTATGCCTAAGGCTGGAAATTTAAATTA

AAATTTTTTTAATAAATATTCCAAAAATATTGCCCCTGAAAAGTGTTGATAAACCCCCAACCGAGCAAA

380
ATG TTA ATG TCC GCG GAC AGT TCA GAT AGC GCC AAG ACT TCT GTG ATC TGC AGC
MET Leu MET Ser Ala Asp Ser Ser Asp Ser Ala Lys Thr Ser Val Ile Cys Ser
1

ACG GTG AGT GCC AGC ATG CTA GCA CCA CCA GCT CCA GAA CAG CCC AGC ACC ACA
Thr Val Ser Ala Ser MET Leu Lal Pro Pro Ala Pro Glu Gln Pro Ser Thr Thr

GCA CCA CCC ATT TTG GGG GTA ACA GGT CGA TCT CAC CTG GAA AAT GCC CTG AAA
Ala Pro Pro Ile Leu Gly Val Thr Gly Arg Ser His Leu Glu Asn Ala Leu Lys
                                                                      54

542
CTA CCG CCA AAC ACA AGT GTT TCG GCT TAC TAC CAG CAC AAC AGC AAG CTG GGC
Leu Pro Pro Asn Thr Ser Val Ser Ala Tyr Tyr Gln His Asn Ser Lys Leu Gly

ATG GGC CAG AAT TAC AAT CCG GAA TTC AGG AGC CTG GTA GCA CCT GTC ACA GAT
MET Gly Gln Asn Tyr Asn Pro Glu Phe Arg Ser Leu Val Ala Pro Val Thr Asp
```

TABLE 1-continued

```
CTG GAT ACT GTG CCA CCC ACA GGT GTG ACC ATG GCG AGT TCT TCG AAT TCT CCC
Leu Asp Thr Val Pro Pro Thr Gly Val Thr Met Ala Ser Ser Ser Asn Ser Pro
                                                                      108

AAC TCC TCC GTC AAG CTG CCC CAC AGC CGC GTG ATC TTT GTC AGC AAA TCG AGT
Asn Ser Ser Val Lys Leu Pro His Ser Gly Val Ile Phe Val Ser Lys Ser Ser

GCC GTC AGC ACC ACC GAT GGT CCC ACT GCA GTG TTG CAA CAG CAG CAG CCG CAG
Ala Val Ser Thr Thr Asp Gly Pro Thr Ala Val Leu Gln Gln Gln Gln Pro Gln
812
CAG CAA ATG CCC CAG CAC TTC GAG TCC CTG CCC CAC CAC CAC CCC CAG CAG GAA
Gln Gln MET Pro Gln His Phe Glu Ser Leu Pro His His His Pro Gln Gln Glu
                                                                      162
```

Panel 4

```
812
CAG CAA ATG CCC CAG CAC TTC GAG TCC CTG CCC CAC CAC CAC CCC CAG CAG GAA
Gln Gln MET Pro Gln His Phe Glu Ser Leu Pro His His His Pro Gln Gln Glu
                                                                      162

CAC CAG CCA CAG CAG CAG CAG CAA CAA CAT CAC CTT CAG CAC CAC CCA CAT CCA
His Gln Pro Gln Gln Gln Gln Gln Gln His His Leu Gln His His Pro His Pro

CAT GTG ATG TAT CCG CAC GGA TAT CAG CAG GCC AAT CTG CAC CAC TCG GGT GGT
His Val MET Tyr Pro His Gly Tyr Gln Gln Ala Asn Leu His His Ser Gly Gly

ATT GCT GTG GTT CCG GCG GAT TCG CGT CCC CAG ACT CCC GAG TAC ATC AAG TCC
Ile Ala Val Val Pro Ala Asp Ser Arg Pro Gln Thr Pro Glu Tyr Ile Lys Ser
                                                                      216

TAC CCA GTT ATG GAT ACA ACT GTG GCT AGT TCG GTA AAG GGG GAA CCA GAA CTC
Tyr Pro Val MET Asp Thr Thr Val Ala Ser Ser Val Lys Gly Glu Pro Glu Leu
```

GTGAGTTGTG .. intron 1 .. TTCTTTGCAG

```
1082
AAC ATA GAA TTC GAT GGC ACC ACA GTG CTG TGC CGC GTT TGC CGG GAT AAG GCC
Asn Ile Glu Phe Asp Gly Thr Thr Val Leu Cys Arg Val Cys Gly Asp Lys Ala
```

GTAAGTTCGT .. intron 2 .. ATCGTTTCAG

```
TCC GGT TTC CAT TAC GGC GTG CAT TCC TGC GAG GGT TGC AAG GGA TTC TTC CGC
Ser Gly Phe His Tyr Gly Val His Ser Cys Glu Gly Cys Lys Gly Phe Phe Arg
                                                                      270

CGC TCC ATC CAG CAA AAG ATC CAG TAT CGC CCG TGC ACC AAG AAT CAG CAG TGC
Arg Ser Ile Gln Gln Lys Ile Gln Tyr Arg Pro Cys Thr Lys Asn Gln Gln Cys

AGC ATT CTG CGC ATC AAT CGC AAT CGT TGT CAA TAT TGC CGC CTG AAA AAG TGC
Ser Ile Leu Arg Ile Asn Arg Asn Arg Cys Gln Tyr Cys Arg Leu Lys Lys Cys
```

GTGAGTACCT .. intron 3 .. CCAATTGCAG

```
ATT GCC GTG GGC ATG AGT CGC GAT GCT GTG CGT TTT GGA CGC GTG CCG AAG CGC
Ile Ala Val Gly MET Ser Arg Asp Ala Val Arg Phe Gly Arg Val Pro Lys Arg
                                                                      324
1352
GAA AAG GCG CGT ATC CTG GCG GCC ATG CAA CAG AGC ACC CAG AAT CGC GGC CAG
Glu Lys Ala Arg Ile Leu Ala Ala MET Gln Gln Ser Thr Gln Asn Arg Gly Gln

CAG CGA GCC CTC GCC ACC GAG CTG GAT GAC CAG CCA CGC CTC CTC GCC GCC GTG
Gln Arg Ala Leu Ala Thr Glu Leu Asp Asp Gln Pro Arg Leu Leu Ala Ala Val

CTG CGC GCC CAC CTC GAG ACC TGT GAG TTC ACC AAG GAG AAG GTC TCG GCG ATG
Leu Arg Ala His Leu Glu Thr Cys Glu Phe Thr Lys Glu Lys Val Ser Ala MET
                                                                      378
```

GTAAGTCTCA .. intron 4 .. ATTTCTTCAG

```
CGG CAG CGG GCG CGG GAT TGC CCC TCC TAC TCC ATG CCC ACA CTT CTG GCC TGT
Arg Gln Arg Ala Arg Asp Cys Pro Ser Tyr Ser MET Pro Thr Leu Leu Ala Cys
```

TABLE 1-continued

Panel 5

| | | | | | | | | | | | | | | | | | |
|---|---|---|---|---|---|---|---|---|---|---|---|---|---|---|---|---|---|
| CCG | CTG | AAC | CCC | GCC | CCT | GAA | CTG | CAA | TCG | GAG | CAG | GAG | TTC | TCG | CAG | CGT | TTC |
| Pro | Leu | Asn | Pro | Ala | Pro | Glu | Leu | Gln | Ser | Glu | Gln | Glu | Phe | Ser | Gln | Arg | Phe |

1622

| | | | | | | | | | | | | | | | | | |
|---|---|---|---|---|---|---|---|---|---|---|---|---|---|---|---|---|---|
| GCC | CAC | GTA | ATT | CGC | GGC | GTG | ATC | GAC | TTT | GCC | GGC | ATG | ATT | CCC | GGC | TTC | CAG |
| Ala | His | Val | Ile | Arg | Gly | Val | Ile | Asp | Phe | Ala | Gly | MET | Ile | Pro | Gly | Phe | Gln 432 |

| | | | | | | | | | | | | | | | | | |
|---|---|---|---|---|---|---|---|---|---|---|---|---|---|---|---|---|---|
| CTG | CTC | ACC | CAG | GAC | GAT | AAG | TTC | ACG | CTC | CTG | AAG | GCG | GGA | CTC | TTC | GAC | GCC |
| Leu | Leu | Thr | Gln | Asp | Asp | Lys | Phe | Thr | Leu | Leu | Lys | Ala | Gly | Leu | Phe | Asp | Ala |

| | | | | | | | | | | | | | | | | | |
|---|---|---|---|---|---|---|---|---|---|---|---|---|---|---|---|---|---|
| CTG | TTT | GTG | CGC | CTG | ATC | TGC | ATG | TTT | GAC | TCG | TCG | ATA | AAC | TCA | ATC | ATC | TGT |
| Leu | Phe | Val | Arg | Leu | Ile | Cys | MET | Phe | Asp | Ser | Ser | Ile | Asn | Ser | Ile | Ile | Cys |

| | | | | | | | | | | | | | | | | | |
|---|---|---|---|---|---|---|---|---|---|---|---|---|---|---|---|---|---|
| CTA | AAT | GGC | CAG | GTG | ATG | CGA | CGG | GAT | GCC | ATC | CAG | AAC | GGA | GCC | AAT | GCC | CGC |
| Leu | Asn | Gly | Gln | Val | MET | Arg | Arg | Asp | Ala | Ile | Gln | Asn | Gly | Ala | Asn | Ala | Arg 486 |

| | | | | | | | | | | | | | | | | | |
|---|---|---|---|---|---|---|---|---|---|---|---|---|---|---|---|---|---|
| TTC | CTG | GTG | GAC | TCC | ACC | TTC | AAT | TTC | GCG | GAG | CGC | ATG | AAC | TCG | ATG | AAC | CTG |
| Phe | Leu | Val | Asp | Ser | Thr | Phe | Asn | Phe | Ala | Glu | Arg | MET | Asn | Ser | MET | Asn | Leu |

1892

| | | | | | | | | | | | | | | | | | |
|---|---|---|---|---|---|---|---|---|---|---|---|---|---|---|---|---|---|
| ACA | GAT | GCC | GAG | ATA | GGC | CTG | TTC | TGC | GCC | ATC | GTT | CTG | ATT | ACG | CCG | GAT | CGC |
| Thr | Asp | Ala | Glu | Ile | Gly | Leu | Phe | Cys | Ala | Ile | Val | Leu | Ile | Thr | Pro | Asp | Arg |

| | | | | | | | | | | | | | | | | | |
|---|---|---|---|---|---|---|---|---|---|---|---|---|---|---|---|---|---|
| CCC | GGT | TTG | CGC | AAC | CTG | GAG | CTG | ATC | GAG | AAG | ATG | TAC | TCG | CGA | CTC | AAG | GGC |
| Pro | Gly | Leu | Arg | Asn | Leu | Glu | Leu | Ile | Glu | Lys | MET | Tyr | Ser | Arg | Leu | Lys | Gly 540 |

| | | | | | | | | | | | | | | | | | |
|---|---|---|---|---|---|---|---|---|---|---|---|---|---|---|---|---|---|
| TGC | CTG | CAG | TAC | ATT | GTC | GCC | CAG | AAT | AGG | CCC | GAT | CAG | CCC | GAG | TTC | CTG | GCC |
| Cys | Leu | Gln | Tyr | Ile | Val | Ala | Gln | Asn | Arg | Pro | Asp | Gln | Pro | Glu | Phe | Leu | Ala |

| | | | | | | | | | | | | | | | | | |
|---|---|---|---|---|---|---|---|---|---|---|---|---|---|---|---|---|---|
| AAG | TTG | CTG | GAG | ACG | ATG | CCC | GAT | CTG | CGC | ACC | CTG | AGC | ACC | CTG | CAC | ACC | GAG |
| Lys | Leu | Leu | Glu | Thr | MET | Pro | Asp | Leu | Arg | Thr | Leu | Ser | Thr | Leu | His | Thr | Glu |

| | | | | | | | | | | | | | | | | | |
|---|---|---|---|---|---|---|---|---|---|---|---|---|---|---|---|---|---|
| AAA | CTG | GTA | GTT | TTC | CGC | ACC | GAG | CAC | AAG | GAG | CTG | CTG | CGC | CAG | CAG | ATG | TGG |
| Lys | Leu | Val | Val | Phe | Arg | Thr | Glu | His | Lys | Glu | Leu | Leu | Arg | Gln | Gln | MET | Trp 594 |

2162

| | | | | | | | | | | | | | | | | | |
|---|---|---|---|---|---|---|---|---|---|---|---|---|---|---|---|---|---|
| TCC | ATG | GAG | GAC | GGC | AAC | AAC | AGC | GAT | GGC | CAG | CAG | AAC | AAG | TCG | CCC | TCG | GGC |
| Ser | MET | Glu | Asp | Gly | Asn | Asn | Ser | Asp | Gly | Gln | Gln | Asn | Lys | Ser | Pro | Ser | Gly |

| | | | | | | | | | | | | | | | | | |
|---|---|---|---|---|---|---|---|---|---|---|---|---|---|---|---|---|---|
| AGC | TGG | GCG | GAT | GCC | ATG | GAC | GTG | GAG | GCG | GCC | AAG | AGT | CCG | CTT | GGC | TCG | GTA |
| Ser | Trp | Ala | Asp | Ala | MET | Asp | Val | Glu | Ala | Ala | Lys | Ser | Pro | Leu | Gly | Ser | Val |

| | | | | | | | | | | | | | | | | | |
|---|---|---|---|---|---|---|---|---|---|---|---|---|---|---|---|---|---|
| TCG | AGC | ACT | GAG | TCC | GCC | GAC | CTG | GAC | TAC | GGC | AGT | CCG | AGC | AGT | TCG | CAG | CCA |
| Ser | Ser | Thr | Glu | Ser | Ala | Asp | Leu | Asp | Tyr | Gly | Ser | Pro | Ser | Ser | Ser | Gln | Pro 648 |

| | | | | | | | | | | | | | | | | | |
|---|---|---|---|---|---|---|---|---|---|---|---|---|---|---|---|---|---|
| CAG | GGC | GTG | TCT | CTG | CCC | TCG | CCG | CCT | CAG | CAA | CAG | CCC | TCG | GCT | CTG | GCC | AGC |
| Gln | Gly | Val | Ser | Leu | Pro | Ser | Pro | Pro | Gln | Gln | Gln | Pro | Ser | Ala | Leu | Ala | Ser |

| | | | | | | | | | | | | | | | | | |
|---|---|---|---|---|---|---|---|---|---|---|---|---|---|---|---|---|---|
| TCG | GCT | CCT | CTG | CTG | GCG | GCC | ACC | CTC | TCC | GGA | GGA | TGT | CCC | CTG | CGC | AAC | CGG |
| Ser | Ala | Pro | Leu | Leu | Ala | Ala | Thr | Leu | Ser | Gly | Gly | Cys | Pro | Leu | Arg | Asn | Arg |

2432

| | | | | | | | | | | | | | | | | | |
|---|---|---|---|---|---|---|---|---|---|---|---|---|---|---|---|---|---|
| GCC | AAT | TCC | GGC | TCC | AGC | GGT | GAC | TCC | GGA | GCA | GCT | GAG | ATG | GAT | ATC | GTT | GGC |
| Ala | Asn | Ser | Gly | Ser | Ser | Gly | Asp | Ser | Gly | Ala | Ala | Glu | MET | Asp | Ile | Val | Gly 702 |

Panel 6

2432

| | | | | | | | | | | | | | | | | | |
|---|---|---|---|---|---|---|---|---|---|---|---|---|---|---|---|---|---|
| GCC | AAT | TCC | GGC | TCC | AGC | GGT | GAC | TCC | GGA | GCA | GCT | GAG | ATG | GAT | ATC | GTT | GGC |
| Ala | Asn | Ser | Gly | Ser | Ser | Gly | Asp | Ser | Gly | Ala | Ala | Glu | MET | Asp | Ile | Val | Gly 702 |

| | | | | | | | | | | | | | | | | | |
|---|---|---|---|---|---|---|---|---|---|---|---|---|---|---|---|---|---|
| TCG | CAC | GCA | CAT | CTC | ACC | CAG | AAC | GGG | CTG | ACA | ATC | ACG | CCG | ATT | GTG | CGA | CAC |
| Ser | His | Ala | His | Leu | Thr | Gln | Asn | Gly | Leu | Thr | Ile | Thr | Pro | Ile | Val | Arg | His |

GTAGTATCTT..intron 5..TTTCTTACAG

| | | | | | | | | | | | | | | | | |
|---|---|---|---|---|---|---|---|---|---|---|---|---|---|---|---|---|
| CAG | CAG | CAG | CAA | CAA | CAG | CAG | CAG | CAG | ATC | GGA | ATA | CTC | AAT | AAT | GCG | CAT | TCC |
| Gln | Gln | Gln | Gln | Gln | Gln | Gln | Gln | Gln | Ile | Gly | Ile | Leu | Asn | Asn | Ala | His | Ser |

TABLE 1-continued

| | | | | | | | | | | | | | | | | |
|---|---|---|---|---|---|---|---|---|---|---|---|---|---|---|---|---|
|CGC|AAC|TTG|AAT|GGG|GGA|CAC|GCG|ATG|TGC|CAG|CAA|CAG|CAG|CAG|CAC|CCA|CAA|
|Arg|Asn|Leu|Asn|Gly|Gly|His|Ala|MET|Cys|Gln|Gln|Gln|Gln|Gln|His|Pro|Gln|
| | | | | | | | | | | | | | | | | |756|

G (Dm4925)

|CTG|CAC|CAC|CAC|TTG|ACA|GCC|GGA|GCT|GCC|CGC|TAC|AGA|AAG|CTA|GAT|TCG|CCC|
|---|---|---|---|---|---|---|---|---|---|---|---|---|---|---|---|---|---|
|Leu|His|His|His|Leu|Thr|Ala|Gly|Ala|Ala|Arg|Tyr|Arg|Lys|Leu Arg|Asp|Ser|Pro|

2702

|ACG|GAT|TCG|GGC|ATT|GAG|TCG|GGC|AAC|GAG|AAG|AAC|GAG|TGC|AAG|GCG|GTG|AGT|
|---|---|---|---|---|---|---|---|---|---|---|---|---|---|---|---|---|---|
|Thr|Asp|Ser|Gly|Ile|Glu|Ser|Gly|Asn|Glu|Lys|Asn|Glu|Cys|Lys|Ala|Val|Ser|

|TCG|GGG|GGA|AGT|TCC|TCG|TGC|TCC|AGT|CCG|CGT|TCC|AGT|GTG|GAT|GAT|GCG|CTG|
|---|---|---|---|---|---|---|---|---|---|---|---|---|---|---|---|---|---|
|Ser|Gly|Gly|Ser|Ser|Ser|Cys|Ser|Ser|Pro|Arg|Ser|Ser|Val|Asp|Asp|Ala|Leu|
| | | | | | | | | | | | | | | | | |810|

|GAC|TGC|AGC|GAT|GCC|GCC|GCC|AAT|CAC|AAT|CAG|GTG|GTG|CAG|CAT|CCG|CAG|CTG|
|---|---|---|---|---|---|---|---|---|---|---|---|---|---|---|---|---|---|
|Asp|Cys|Ser|Asp|Ala|Ala|Ala|Asn|His|Asn|Gln|Val|Val|Gln|His|Pro|Gln|Leu|

|AGT|GTG|GTG|TCC|GTG|TCA|CCA|GTT|CGC|TCG|CCC|CAG|CCC|TCC|ACC|AGC|AGC|CAT|
|---|---|---|---|---|---|---|---|---|---|---|---|---|---|---|---|---|---|
|Ser|Val|Val|Ser|Val|Ser|Pro|Val|Arg|Ser|Pro|Gln|Pro|Ser|Thr|Ser|Ser|His|

|CTG|AAG|CGA|CAG|ATT|GTG|GAG|GAT|ATG|CCC|GTG|CTG|AAG|CGC|GTG|CTG|CAG|GCT|
|---|---|---|---|---|---|---|---|---|---|---|---|---|---|---|---|---|---|
|Leu|Lys|Arg|Gln|Ile|Val|Glu|Asp|MET|Pro|Val|Leu|Lys|Arg|Val|Leu|Gln|Ala|
| | | | | | | | | | | | | | | | | |864|

2972

|CCC|CCT|CTG|TAC|GAT|ACC|AAC|TCG|CTG|ATG|GAC|GAG|GCC|TAC|AAG|CCG|CAC|AAG|
|---|---|---|---|---|---|---|---|---|---|---|---|---|---|---|---|---|---|
|Pro|Pro|Leu|Tyr|Asp|Thr|Asn|Ser|Leu|MET|Asp|Glu|Ala|Tyr|Lys|Pro|His|Lys|

|AAA|TTC|CGG|GCC|CTG|CGG|CAT|CGC|GAG|TTC|GAG|ACC|GCC|GAG|GCG|GAT|GCC|AGC|
|---|---|---|---|---|---|---|---|---|---|---|---|---|---|---|---|---|---|
|Lys|Phe|Arg|Ala|Leu|Arg|His|Arg|Glu|Phe|Glu|Thr|Ala|Glu|Ala|Asp|Ala|Ser|

|AGT|TCC|ACT|TCC|GGC|TCG|AAC|AGC|CTG|AGT|GCC|GGC|AGT|CCG|CGG|CAG|AGC|CCA|
|---|---|---|---|---|---|---|---|---|---|---|---|---|---|---|---|---|---|
|Ser|Ser|Thr|Ser|Gly|Ser|Asn|Ser|Leu|Ser|Ala|Gly|Ser|Pro|Arg|Gln|Ser|Pro|
| | | | | | | | | | | | | | | | | |918|

|GTC|CCG|AAC|AGT|GTG|GCC|ACG|CCC|CCG|CCA|TCG|GCG|GCC|AGC|GCC|GCC|GCA|GGT|
|---|---|---|---|---|---|---|---|---|---|---|---|---|---|---|---|---|---|
|Val|Pro|Asn|Ser|Val|Ala|Thr|Pro|Pro|Pro|Ser|Ala|Ala|Ser|Ala|Ala|Ala|Gly|

|AAT|CCC|GCC|CAG|AGC|CAG|CTG|CAC|ATG|CAC|CTG|ACC|CGC|AGC|AGC|CCC|AAG|GCC|
|---|---|---|---|---|---|---|---|---|---|---|---|---|---|---|---|---|---|
|Asn|Pro|Ala|Gln|Ser|Gln|Leu|His|MET|His|Leu|Thr|Arg|Ser|Ser|Pro|Lys|Ala|

Panel 7

3242

|TCG|ATG|GCC|AGC|TCG|CAC|TCG|GTG|CTG|GCC|AAG|TCT|CTC|ATG|GCC|GAG|CCG|CGC|
|---|---|---|---|---|---|---|---|---|---|---|---|---|---|---|---|---|---|
|Ser|MET|Ala|Ser|Ser|His|Ser|Val|Leu|Ala|Lys|Ser|Leu|MET|Ala|Glu|Pro|Arg|
| | | | | | | | | | | | | | | | | |972|

|ATG|ACG|CCC|GAG|CAG|ATG|AAG|CGC|AGC|GAT|ATT|ATC|CAA|AAC|TAC|TTG|AAG|CGC|
|---|---|---|---|---|---|---|---|---|---|---|---|---|---|---|---|---|---|
|MET|Thr|Pro|Glu|Gln|MET|Lys|Arg|Ser|Asp|Ile|Ile|Gln|Asn|Tyr|Leu|Lys|Arg|

|GAG|AAC|AGC|ACA|GCA|GCC|AGC|AGC|ACC|ACC|AAT|GGC|GTG|GGC|AAC|CGC|AGT|CCC|
|---|---|---|---|---|---|---|---|---|---|---|---|---|---|---|---|---|---|
|Glu|Asn|Ser|Thr|Ala|Ala|Ser|Ser|Thr|Thr|Asn|Gly|Val|Gly|Asn|Arg|Ser|Pro|

|AGC|AGC|AGC|TCC|ACA|CCG|CCG|CCG|TCG|GCG|GTC|CAG|AAT|CAG|CAG|CGT|TGG|GGC|
|---|---|---|---|---|---|---|---|---|---|---|---|---|---|---|---|---|---|
|Ser|Ser|Ser|Ser|Thr|Pro|Pro|Pro|Ser|Ala|Val|Gln|Asn|Gln|Gln|Arg|Trp|Gly|
| | | | | | | | | | | | | | | | | |1026|

|AGC|AGC|TCG|GTG|ATC|ACC|ACC|ACC|TGC|CAG|CAG|AGC|CAG|CAG|TCC|GTG|TCG|CCG|
|---|---|---|---|---|---|---|---|---|---|---|---|---|---|---|---|---|---|
|Ser|Ser|Ser|Val|Ile|Thr|Thr|Thr|Cys|Gln|Gln|Arg|Gln|Gln|Ser|Val|Ser|Pro|

3512

|CAC|AGC|AAC|GGT|TCC|AGC|TCC|AGT|TCG|AGC|TCT|AGC|TCC|AGC|TCC|AGT|TCG|TCA|
|---|---|---|---|---|---|---|---|---|---|---|---|---|---|---|---|---|---|
|His|Ser|Asn|Gly|Ser|Ser|Ser|Ser|Ser|Ser|Ser|Ser|Ser|Ser|Ser|Ser|Ser|Ser|

|TCC|TCC|TCC|ACA|TCC|TCC|AAC|TGC|AGC|TCC|AGC|TCG|GCC|AGC|AGC|TGC|CAG|TAT|
|---|---|---|---|---|---|---|---|---|---|---|---|---|---|---|---|---|---|
|Ser|Ser|Ser|Thr|Ser|Ser|Asn|Cys|Ser|Ser|Ser|Ser|Ala|Ser|Ser|Cys|Gln|Tyr|
| | | | | | | | | | | | | | | | | |1080|

|TTC|CAG|TCG|CCG|CAC|TCC|ACC|AGC|AAC|GGC|ACC|AGT|GCA|CCG|GCG|AGC|TCC|AGT|
|---|---|---|---|---|---|---|---|---|---|---|---|---|---|---|---|---|---|
|Phe|Gln|Ser|Pro|His|Ser|Thr|Ser|Asn|Gly|Thr|Ser|Ala|Pro|Ala|Ser|Ser|Ser|

|TCG|GGA|TCG|AAC|AGC|GCC|ACG|CCC|CTG|CTG|GAA|CTG|CAG|GTG|GAC|ATT|GCT|GAC|
|---|---|---|---|---|---|---|---|---|---|---|---|---|---|---|---|---|---|
|Ser|Gly|Ser|Asn|Ser|Ala|Thr|Pro|Leu|Leu|Glu|Leu|Gln|Val|Asp|Ile|Ala|Asp|

|TCG|GCG|CAG|CCT|CTC|AAT|TTG|TCC|AAG|AAA|TCG|CCC|ACG|CCG|CCG|CCC|AGC|AAG|
|---|---|---|---|---|---|---|---|---|---|---|---|---|---|---|---|---|---|
|Ser|Ala|Gln|Pro|Leu|Asn|Leu|Ser|Lys|Lys|Ser|Pro|Thr|Pro|Pro|Pro|Ser|Lys|
| | | | | | | | | | | | | | | | | |1134|

TABLE 1-continued

```
3782
CTG CAC GCT CTG GTG GCC GCC GCC AAT GCC GTT CAA AGG TAT CCC ACA TTG TCC
Leu His Ala Leu Val Ala Ala Ala Asn Ala Val Gln Arg Tyr Pro Thr Leu Ser

GCC GAC GTC ACA GTG ACA GCC TCC AAT GGC GGG TCC TCC GTC GGC GGC GGC GAG
Ala Asp Val Thr Val Thr Ala Ser Asn Gly Gly Ser Ser Val Gly Gly Gly Glu

TCC GGC CGC CAG CAG CAG TCC GCC GGC GAG TGT CGG CTC CCC CAA TCC GGG CCT
Ser Gly Arg Gln Gln Gln Ser Ala Gly Glu Cys Gly Leu Pro Gln Ser Gly Pro
                                                                     1186

GAG CGC CGC CGT GCA CAA GGT AAT GCT GGA GGC GTA AGA GCG GGA GGA GGT AGG
Glu Arg Arg Arg Ala Gln Gly Asn Ala Gly Gly Val Arg Ala Gly Gly Gly Arg

TGG TTT TAC GCG GAG AAG TGG GAG AGA CAG AGA CTG GGA GTG GCA GTT CAG CGA
Trp Phe Tyr Ala Glu Lys Trp Glu Arg Gln Arg Leu Gly Val Ala Val Gln Arg

4052
AGC AGG AAG CAG GAT CAC TTG GAG CGG CGG GAG TTG AAT TAA.
Ser Arg Lys Gln Asp His Leu Glu Arg Arg Glu Leu Asn
                                              1237
```

Panel 8

```
4052
AGC AGG AAG CAG GAT CAC TTG GAG CGG CGG GAG TTG AAT TAA.
Ser Arg Lys Gln Asp His Leu Glu Arg Arg Glu Leu Asn
                                              1237
```

ATTATTTTACCATTTAATTGAGACGTGTACAAAGTTTGAAAGCAAAACCAACATGCATGCAATTTAAAAC

TAATATTTAAAGCAACAACAAACAAAACAACTACAAGTTATTAATTTAAAAAACAAACAAACAAACAAAC

4234
AACAAAAAACCCAAGCTTGAATGGTATTACAAAAGAAAAAGAAAAACAGAAAAAATATAAATATATTTTA

GCAGTTAAACTTTAACGTAGCAAGAAACCAACAAACCCAAGGCAGCGCTCTGATTTCGCATTAACTTTTC

4374
TTCAGCTGCTACCGAAAACGCCCCTCACCTCCCCCCCACCCAACCCTTCCTCCACACACCAACCGTCTTT

CGACCCCTGATTGTTTTATAAGTTTTAAGCTCTTGTTGTACATATTAATTACGTTTATTGGTAACTATGT

4514
TTAGCGCTTTAGTTGTAGTTGGAGCAAAACTACTTTGCTTTTTTGGATGTTTTTTGAAAAAACTGCAAAT

TATTATT<u>ATTAAAT</u>TTTTAAATACCTAAAAACAAAACAATGTGTGTGAAATTTTTTATTGTGCGATCTCC
         ↳ poly A site cDm4927 and cDm4928

4654
AAGCAGAATGAAGTGCAGTTTGCAACAAATTTTAACTACGATTAAGTTGATAACGATTCATTTTTTATGA

ATTTAACTAATTTTATGAATTTGTTATAGTTTTCCACCCTTCTATAGATCTTCTATCTGATCATCTAGCT

4794
ACCCGTATTCCTGATTTCTCCTTTGGCACAAAGCTCTTCTCTATGCTAAAGAATCAAGTGGAATAAATAT

TGTTTTCTAATTTTAAAACTACCACAAAAATACGATTAAAATATACACGAAGTAATGAAAATCAAACAAA

4934
ATGCTTAAAGTTTTAGCAGCAAGCAGTAAAACGACGATGAAGAAGAGAAACCCAACGTTAAATATATCTG

TTGTGTACATAGTTAAATGTTAAATTAAACACAAAAACATATTTAAAGTACATATAAATACACATAATTA

5074
TTAATGAAGAAACCTATGCTTAAAAGATTCAATGTTTGATTGGCATCTTAGAAAACCAAGCGAAAAATAC

AAAAAAAAATCAACAAACAAAAATTATGATATATTATTTAAAAGTAAAGTATACATTTACATTACAGAAA

5214
AACAAAAGAGAAAACTTGCGGTAGCAACAAAACTATTATATTAATTACATTTTAATTATGCTGTACTATT

ATGATTATTAATTATTATGATTAATTAATTACGATTTTTATGCTTAGACAAACCAACAAAAAACAAATAT

5354
GCAAAAACC<u>ATTAAAA</u>AAAAAAACAAAAAACAAGCAAAAAAT
         ↳ putative polyadenylation signal for long transcripts TABLE 1-continued Panel 9

B

CGACGCGTTTGGAGTGAACGTCCTCAGTTGGCACACAAAAACAAAAACACAAAACGACAGCAACAACATC

−141
GGTGGGGGGAGTACGAGCGGGATGGGGGTAATGGGGGGCACCGGGGGAGTGGAGGCC<u>GAGAGAGCCAGAG</u>

<u>AGCGA</u>CCCGAAGCAACACAACACCAACACGAGGCCCAAAAAGACACTTCGGCTGGGTTCAGCTCGTGTTG

+1
CTCTGGGTCGT<u>TTTGT</u>ATTGCTGGTGGACGCTGCTTTCATTCGCAAATTGCTCGTCGTTGGCAGCGGTTG
                                              ↳ mRNA start site

TGCAGAGCAAGAAAAGCGCGCGAAAAACCAAGCAAAAAATTAATACAGCTGGATCAAGCGAAAGAGATAG

AGAGCAGAGTCAACAGCAACAA<u>AT</u>GTTCAATAGCAAA<u>AT</u>GATATCGCATATTTTTGTTGGTGCCAGTGAAG

+211
TGAGATCAAAGTGAAGTGTGCA<u>AT</u>GTTCCTTATTAGCAAATCGTAGAGCAACCAACAATCGAGAGTTCAA

```
                                                            284
       GTGTCATTTCGAAGCCAAAAAGCAAAATCTCTAATTCAAAT ATG GTT TGT GCA ATG CAA
                                                 MET Val Cys Ala MET Gln
                                                  1

302
GAG GTT GCT GCT GTG CAG CAT CAG CAG CAG CAA CAG CAA CTC CAG TTG CCC CAG
Glu Val Lal Ala Val Gln His Gln Gln Gln Gln Gln Gln Leu Gln Leu Pro Gln
                                                                      24

CAG CAA CAG CAG CAG CAG CAG ACA ACA CAG CAG CAA CAT GCA ACA ACG ATA GTG
Gln Gln Hln Gln Gln Gln Gln Thr Thr Gln Gln Gln His Ala Thr Thr Ile Val

CTG CTG ACG GGC AAT GGC GGC GGT AAT CTG CAC ATT GTC GCC ACA CCG CAA CAG
Leu Leu Thr Gly Asn Gly Gly Gly Asn Leu His Ile Val Ala Thr Pro Gln Gln

CAT CAG CCG ATG CAT CAG CTC CAC CAT CAG CAT CAG CAT CAG CAT CAG CAC CAG
His Gln Pro MET His Gln Leu His His Gln His Gln His Gln His Gln His Gln
                                                                       78

CAG CAG GCC AAG AGC CAA CAG CTG AAG CAA CAA CAC TCG GCG CTG GTC AAG TTG
Gln Gln Ala Lys Ser Gln Gln Leu Lys Gln Gln His Ser Ala Leu Val Lys Leu

572
CTG GAG TCG GCG CCC ATC AAG CAG CAA CAG CAG ACG CCC AAG CAA ATT GTT TAC
Leu Glu Ser Ala Pro Ile Lys Gln Gln Gln Gln Thr Pro Lys Gln Ile Val Tyr

CTG CAG CAG CAG CAG CAG CAA CCG CAA CGC AAA AGA CTG AAA AAC GAA GCA GCA
Leu Gln Gln Gln Gln Gln Gln Pro Gln Arg Lys Arg Leu Lys Asn Glu Ala Ala
                                                                       132

ATC GTA CAA CAG CAA CAA CAA ACA CCT GCA ACA CTA GTA AAG ACA ACA ACC ACC
Ile Val Gln Gln Gln Gln Gln Thr Pro Ala Thr Leu Val Lys Thr Thr Thr Thr

AGC AAC AGC AAC AGC AAC AAC ACC CAG ACA ACA AAT AGT ATT AGT CAG CAG CAA
Ser Asn Ser Asn Ser Asn Asn Thr Gln Thr Thr Asn Ser Ile Ser Gln Gln Gln
```

Panel 10

```
AGC AAC AGC AAC AGC AAC AAC ACC CAG ACA ACA AAT AGT ATT AGT CAG CAG CAA
Ser Asn Ser Asn Ser Asn Asn Thr Gln Thr Thr Asn Ser Ile Ser Gln Gln Gln

CAG CAG CAT CAG ATT GTG TTG CAG CAC CAG CAG CCA GCC GCG GCA GCA ACA CCA
Gln Gln His Gln Ile Val Leu Gln His Gln Gln Pro Ala Ala Ala Ala Thr Pro
                                                                       186

842
AAG CCA TGT GCC GAT CTG AGC GCC AAA AAT GAC AGC GAG TCG GGC ATC GAC GAG
Lys Pro Cys Ala Asp Leu Ser Ala Lys Asn Asp Ser Glu Ser Gly Ile Asp Glu

GAC TGC CCC AAC AGC GAT GAG GAT TGC CCC AAT GCC AAC CCG GCG GGC ACA TCG
Asp Cys Pro Asn Ser Asp Glu Asp Cys Pro Asn Ala Asn Pro Ala Gly Thr Ser

CTC GAG GAC AGC AGC TAC GAG CAG TAT CAG TGC CCC TGG AAG AAG ATA CGC TAT
Leu Glu Asp Ser Ser Tyr Glu Gln Tyr Gln Cys Pro Trp Lys Lys Ile Arg Tyr
                                                                      240
```

TABLE 1-continued

| GCG | CGT | GAG | CTC | CTC | AAG | CAG | CGC | GAG | TTG | GAG | CAG | CAG | CAG | ACC | ACC | GGA | GGC |
|-----|-----|-----|-----|-----|-----|-----|-----|-----|-----|-----|-----|-----|-----|-----|-----|-----|-----|
| Ala | Arg | Glu | Leu | Leu | Lys | Gln | Arg | Glu | Leu | Glu | Gln | Gln | Gln | Thr | Thr | Gly | Gly |

| AGC | AAC | GCG | CAG | CAG | CAA | GTC | GAG | GCG | AAG | CCA | GCT | GCA | ATA | CCC | ACC | AGC | AAC |
|-----|-----|-----|-----|-----|-----|-----|-----|-----|-----|-----|-----|-----|-----|-----|-----|-----|-----|
| Ser | Asn | Ala | Gln | Gln | Gln | Val | Glu | Ala | Lys | Pro | Ala | Ala | Ile | Pro | Thr | Ser | Asn |

1112

| ATC | AAG | CAG | CTG | CAC | TGT | GAT | AGT | CCC | TTT | TCG | GCG | CAG | ACC | CAC | AAG | GAA | ATC |
|-----|-----|-----|-----|-----|-----|-----|-----|-----|-----|-----|-----|-----|-----|-----|-----|-----|-----|
| Ile | Lys | Gln | Leu | His | Cys | Asp | Ser | Pro | Phe | Ser | Ala | Gln | Thr | His | Lys | Glu | Ile 294 |

| GCC | AAT | CTC | CTG | CGC | CAA | CAG | TCC | CAG | CAA | CAA | CAG | GTT | GTG | GCC | ACG | CAG | CAG |
|-----|-----|-----|-----|-----|-----|-----|-----|-----|-----|-----|-----|-----|-----|-----|-----|-----|-----|
| Ala | Asn | Leu | Leu | Arg | Gln | Gln | Ser | Gln | Gln | Gln | Gln | Val | Val | Ala | Thr | Gln | Gln |

| CAG | CAG | CAA | CAG | CAG | CAG | CAG | CAC | CAG | CAC | CAG | CAA | CAA | CGA | AGG | GAT | AGC | TCC |
|-----|-----|-----|-----|-----|-----|-----|-----|-----|-----|-----|-----|-----|-----|-----|-----|-----|-----|
| Gln | Gln | Gln | Gln | Gln | Gln | Gln | His | Gln | His | Gln | Gln | Gln | Arg | Arg | Asp | Ser | Ser |

| GAC | AGC | AAC | TGC | TCG | CTG | ATG | AGC | AAC | TCG | AGC | AAC | TCC | AGT | GCG | GGC | AAT | TGT |
|-----|-----|-----|-----|-----|-----|-----|-----|-----|-----|-----|-----|-----|-----|-----|-----|-----|-----|
| Asp | Ser | Asn | Cys | Ser | Leu | MET | Ser | Asn | Ser | Ser | Asn | Ser | Ser | Ala | Gly | Asn | Cys 348 |

| TGC | ACC | TGC | AAC | GCT | GGC | GAC | GAC | CAG | CAG | CTG | GAG | GAG | ATG | GAC | GAG | GCC | CAC |
|-----|-----|-----|-----|-----|-----|-----|-----|-----|-----|-----|-----|-----|-----|-----|-----|-----|-----|
| Cys | Thr | Cys | Asn | Ala | Gly | Asp | Asp | Gln | Gln | Leu | Glu | Glu | MET | Asp | Glu | Ala | His |

1382

| GAT | TCG | GGC | TGC | GAC | GAT | GAA | CTT | TGC | GAG | CAG | CAT | CAC | CAG | CGA | CTG | GAC | TCC |
|-----|-----|-----|-----|-----|-----|-----|-----|-----|-----|-----|-----|-----|-----|-----|-----|-----|-----|
| Asp | Ser | Gly | Cys | Asp | Asp | Glu | Leu | Cys | Glu | Gln | His | His | Gln | Arg | Leu | Asp | Ser |

| TCC | CAA | CTG | AAT | TAC | CTG | TGC | CAG | AAG | TTC | GAT | GAG | AAA | CTG | GAC | ACG | GCG | CTG |
|-----|-----|-----|-----|-----|-----|-----|-----|-----|-----|-----|-----|-----|-----|-----|-----|-----|-----|
| Ser | Gln | Leu | Asn | Tyr | Leu | Cys | Gln | Lys | Phe | Asp | Glu | Lys | Leu | Asp | Thr | Ala | Leu 402 |

| AGC | AAC | AGC | AGC | GCC | AAC | ACG | GGG | AGG | AAC | ACG | CCA | GCT | GTA | ACA | GCT | AAC | GAA |
|-----|-----|-----|-----|-----|-----|-----|-----|-----|-----|-----|-----|-----|-----|-----|-----|-----|-----|
| Ser | Asn | Ser | Ser | Ala | Asn | Thr | Gly | Arg | Asn | Thr | Pro | Ala | Val | Thr | Ala | Asn | Glu |

1544

| GAT | GCC | GAT | gtaggtttag |
|-----|-----|-----|------------|
| Asp | Ala | Asp | |

Methods cDNA libraries

The λDm4925 and λDm4745 cDNAs were isolated from an O$^r$ early pupal cDNA library in λgt10 (Poole, S. J., L. M. Kauvar, B. Drees, and T. Kornberg, 1985. The engrailed locus of Drosophila: structural analysis of an embryonic transcript. Cell 40:37–40). The two cDNAs (λDm4927 and λDm4928) that were used for 3'-end mapping were isolated from an ecdysone-induced salivary gland cDNA library in λ607 prepared by C. W. Jones. (Our strain collection names for the cDNA clones used in these studies are λfDm4925, λfDm4745, λeDm4927, and λeDm4928.)

Northern blot analysis

Probes to be used for Northern blots were cloned into the vector pφX (from R. Mulligan), containing the φX174 origin of replication cloned in between the HindIII and BamHI sites of pBR322. This allowed the synthesis of single-stranded probe DNA (Arai, K., N. Arai, J. Schlomai, and A. Kornberg, 1980. Replication of duplex DNA of phage φX174 reconstituted with purified enzymes. Proc. Natl. Acad. Sci. 77:3322–3326), which was performed by the incubation of supercoiled plasmid DNA with gene A protein, rep and ssb proteins, and DNA polymerase III holoenzyme (all generously provided by the A. Kornberg laboratory) in a reaction containing 20 mM Tris Cl (pH 7.5), 80 μg/ml BSA, 4% glycerol, 20 mM DTT, 1 mM ATP, 16 mM concentrations of the three unlabeled deoxynucleotides and 1.6 mM concentrations of the labeled deoxynucleotide for 1 hour at 30° C. EDTA was then added to 20 mM, SDS to 0.1%, and proteinase K to 50 μg/ml. The reactions were digested for 30 minutes at 37° C., and unincorporated label was removed by gel filtration.

S1 nuclease protection and primer extension analysis

Single-stranded probes, prepared as described above by the φX in vitro replication system, were purified by electrophoresis on low melting point agarose gels for use as S1 probes. All other probes were prepared by extension of the −20, 17-mer sequencing primer (New England Biolabs) on single-stranded M13mp (Messing, J., 1983. New M13 vectors for cloning. Methods Enzymol. 101:20–78) or pEMBL (Dente, L., G. Cesareni, and R. Cortes, 1983. pEMBL: A new family of single-stranded plasmids. Nucleic Acids Res. 11:1645–1654) recombinant templates using $^{32}$P-labeled nucleotides, followed by cleavage with the appropriate restriction enzyme and purification of the probe on denaturing polyacrylamide gels. Labeled probe (100,000–300,000 cpm) was incubated with 1 μg of poly(A)+ RNA in a 5 μl reaction mixture containing 5 μg of yeast tRNA, 0.4M NaCl, 40 mM PIPES (pH 6.8), and 1 mM EDTA at 60° C. under oil. Reactions were cooled and diluted 1:10 into either 400 mM NaCl, and 4 mM ZnSO$_4$ at 20° C. for 1 hour with S1 digestion or primer extension buffer. S1 nuclease digestions were performed in 50 mM acetate buffer (Na), ~15–150 Vogt units of S1 nuclease (Boehringer) per 50 μm reaction. Primer extensions were performed at 42° C. in 50 mM Tris Cl (pH 8.3 at 42° C.), 80 mM KCl, 2 mM DTT, 1 mM of dATP, dCTP, dGTP, and dTTP, with 20 units of AMV reverse transcriptase (Seikagaku) per 50 μreaction. Reactions were terminated by the addition of EDTA, tRNA carrier was added to the S1 nuclease digestions, and samples were ethanol-precipitated and either electrophoresed directly on 5% or 6% denaturing polyacrylamide gels or glyoxalated (McMaster, G. K., and G. C. Carmichael, 1977. Analysis of single and double-stranded nucleic acids on polyacrylamide and agarose gels by using glyoxal and acridine orange. Proc.

*Natl. Acad. Sci.* 74:4835–4838) and electrophoresed on 1% agarose gels run in 10 mM sodium phosphate buffer (pH 6.8).

DNA sequence analysis

The cDNA clones λDm4927 and λDm4928 were sequenced by chemical degradation (Maxam, A. M., and W. Gilbert, 1980. Sequencing end-labeled DNA with base-specific chemical cleavage. *Methods Enzymol.* 65:499–560). All other sequencing was performed using the dideoxynucleotide chain termination method (Sanger, F., A. R. Coulson, B. F. Barrell, A. J. H. Smith, and B. A. Roe, 1980. Cloning in single-stranded bacteriophage as an aid to rapid DNA sequencing. *J. Mol. Biol.* 143:161–178). Fragments were cloned into M13mp (Messing, J., 1983. New M13 vectors for cloning. *Methods Enzymol.* 101:20–78) or pEMBL (Dente, L., G. Cesareni, and R. Cortes, 1983. pEMBL: A new family of single-stranded plasmids. *Nucleic Acids Res.* 11:1645–1654) vectors and sequenced directly or following the generation of a set of overlapping deletions using exonuclease III (Henikoff, S., 1984. Unidirectional digestion with exonuclease III creates targeted breakpoints for DNA sequencing. *Gene* 28:351–359). Sequencing was performed on both strands of the λDm4925 cDNA, the B-specific region of vDm4745 cDNA, the A- and B-specific 5' genomic regions not represented in the cDNAs, and the 3'-flanking region. The remaining exon boundaries of λDm4745 and genomic regions represented within the cDNA clones were sequenced on one strand.

D. The E75 Gene Encodes Two Members of the Steroid Receptor Superfamily

The coding and noncoding sequences of the E75 A and B mRNAs, their splice junctions, and the 5' and 3–0 flanking sequences are shown in Table 1. Certain sequences of potential interest within the 5' flanking DNA and in the 5' leader mRNA sequences are indicated in the legend to Table 1. We focus here on the large open reading frames of the E75 A and B mRNAs that begin at 380 bp and 284 bp downstream from their respective mRNA start sites, each continuing into the common final exon. The termination codon in exon 5 lies upstream of both alternative polyadenylation sites; thus, the sequence of the encoded protein is not affected by which site is selected. Since the open reading frames in the E75 A and B mRNAs begin in the A0 and B1 exons and merge at the beginning of exon 2, the proteins encoded by the two transcription units differ in the amino-terminal region and are the same in the carboxy-terminal region. The specific amino-terminal regions contain 266 and 423 amino acid residues in the E75 A and B proteins, respectively, while their common carboxy-terminal region consists of 971 residues. The predicted molecular weights of the A and B proteins are thus 132,000 and 151,000. The open reading frames display characteristic *D. melanogaster* codon usage, and their extents have been confirmed by in vitro translation of mRNAs transcribed in vitro from cDNA constructs and by expression of fusion proteins in *E. coli*. The predicted protein sequence for each protein is punctuated by homopolymeric tracts of amino acids which are noted in Table 1 and its legend.

Analysis of the sequences of E75 proteins and comparison to the sequences of known proteins have revealed similarity between the E75 proteins and members of the steroid receptor superfamily (Evans, R. M., 1988. The steroid and thyroid hormone receptor superfamily. *Science* 240:889–895; Green, S., and P. Chambon, 1988. Nuclear receptors enhance our understanding of transcription regulation. *Trends in Genetics* 4:309–314). We have used the nomenclature of Krust el al. (Krust, A., S. Green, P. Argos, V. Kumar, P. Walter, J. Bornert, and P. Chambon, 1986. The chicken oestrogen receptor sequence: Homology with v-erbA and the human oestrogen and glucocorticoid receptors. *EMBO J.* 5:891–897) in dividing the proteins into six regions, letters A–F, in the amino- to carboxy-terminal direction.

Similarity between E75A and other members of this superfamily is strongest in the C region, a cysteine-lysine-arginine-rich region that is necessary and sufficient for the binding of these receptors to DNA (for review, see, Evans, R. M., 1988. The steroid and thyroid hormone receptor superfamily. *Science* 240:889–895; Green, S., and P. Chambon, 1988. Nuclear receptors enhance our understanding of transcription regulation. *Trends in Genetics* 4:309–314). The C region consists of 66–68 amino acids, of which 20 residues are invariant within this family. Among these are nine invariant cysteine residues, eight of which are believed to coordinate zinc in the formation of two zinc finger-like structures (Miller, J., A. D. McLachlan, and A. Klug, 1985. Representative zinc-binding domains in the protein transcription factor IIIA from Xenopus oocytes. *EMBO J.* 4:1609–1614; Freedman, L. P., B. F. Luisi, Z. R. Korszun, R. Basavappa, P. B. Sigler, and K. R. Yamamoto, 1988. The function and structure of the metal coordination sites within the glucocorticoid receptor DNA binding domain. *Nature* 334:543–546; Severne, Y., S. Wieland, W. Schaffner, and S. Rusconi, 1988. Metal binding finger structure of the glucocorticoid receptor defined by site directed mutagenesis. *EMBO J.* 9:2503–2508). Within the C region, E75A contains all of the highly conserved residues and is approximately as closely related to other members of the steroid receptor superfamily as they are to one another. The closest relative of E75 appears to be the human ear-1 gene, which has nearly 80% amino acid identity to E75 A in the DNA-binding domain.

The other region conserved among members of the steroid receptor superfamily is the E region, which is required for steroid binding and for the linkage of steroid-binding and trans-activation functions (for review, see, Evans, R. M., 1988. The steroid and thyroid hormone receptor superfamily. *Science* 240:889–895; Green, S., and P. Chambon, 1988. Nuclear receptors enhance our understanding of transcription regulation. *Trends in Genetics* 4:309–314). Although overall E-region similarity is clearly significant for the comparison of E75 A to the thyroid hormone, vitamin D, and retinoic acid receptors, and ear-1, similarity to the glucocorticoid and estrogen receptors is considerably lower. However, the plots of local similarities show a clear similarity to each of these proteins within three subregions of the E region, with we call El, E2 and E3. The E1 subregion is the most highly conserved and corresponds to a region shown by in vitro mutagenesis to be essential for steroid binding and steroid-dependent trans-activation (Giguere, V., S. M. Hollenberg, M. G. Rosenfield, and R. M. Evans, 1986. Functional domains of the human glucocorticoid receptor. *Cell* 46:645–652; Danielson, M., J. P. Northrop, J. Jonklaas, and G. M. Ringold, 1987. Domains of the glucocorticoid receptor involved in specific and nonspecific deoxyribonucleic acid binding, hormone activation and transcriptional enhancement. *Mol. Endocrinol.* 1:816–822). Region E2 is less highly conserved in primary amino acid sequence but can, in part, be seen as a conserved hydrophobic region in the hydropathy plots of several of these proteins. A deletion of 14 amino acids within this region abolished steroid binding (Rusconi, S., and K. R. Yamamoto, 1987. Functional dissection of the hormone and DNA binding activities of the glucocorticoid receptor. *EMBO J.* 6:1309–1315). E3 falls close to the end of the region that is absolutely required for steroid binding.

While the characteristic structural features of the steroid receptor superfamily are well conserved in E75, two novel variations are seen. The first of these concerns the structure of the E75 B protein, which contains a major alteration within its putative DNA-binding domain. The steroid receptor superfamily DNA-binding domain consists of two DNA-binding zinc fingers separated by a less conserved linker region. In E75, as in nearly all other genes of this family, an intron is found in between the two fingers. In E75, this splice marks the beginning of the region held in common between the E75 A and B proteins. This results in the E75 A protein having two fingers, while the E75 B protein has unrelated B-specific sequences in place of the first finger. Other sequences within the B-specific aminoproximal region may contribute to the DNA-binding domain of the E74B protein.

Alternatively, the B protein might bind DNA with only one finger, as GAL4 transcription factor of yeast appears to do. It is possible that these structural differences imply a functional difference in the DNA-binding properties of the E75 A and B proteins that might allow them to differentially regulate the transcription of the late genes that characterize the secondary response to ecdysone in different target tissues.

In this respect, it should be emphasized that the putative hormone- or ligand-binding domain represented by the E region that is common to the E75A and E75B proteins. Thus, these proteins appear to be receptors for the same hormone that may act to regulate the transcription of different sets of genes. These proteins represent "orphan" receptors in that their hormone, or binding ligand, has not yet been identified. Because ecdysteroids are the only known steroid hormones in Drosophila, the most obvious candidate for an E75 ligand would be ecdysone itself. However, it is unlikely that this is the case since the putative hormone-binding domain of the E75 proteins does not exhibit the high sequence homology to that of the known Drosophila ecdysone receptor encoded by the EcR gene (see Experimental Example III and Table 2) that would be expected if the E75 proteins were also ecdysone receptors. It, therefore, seems likely that the E75 proteins would bind either a terpenoid juvenile hormone or a novel Drosophila hormone.

The second unusual feature of the E75 proteins is the presence of a large F region, encompassing nearly one half of the proteins. Many of the other receptors have very small F regions, and no function has yet been ascribed to this region.

Methods
Protein sequence analysis

Sequence data were compiled using the Bionet system. Protein sequence comparison was performed using FASTP (Lipman, D. J., and W. R. Pearson, 1985. Rapid and sensitive protein similarity searches. *Science* 227:1435–1441) and Bionet IFIND programs.

E. Expression Vectors for E75 Proteins

In order to express the E75 proteins, portions of cDNAs and genomic clones were fused in order to generate cassettes containing the entire E75 A and E75 B protein coding regions. First, BamHI sites were introduced into genomic clones upstream of the initial AUGs of the large open reading frames. Then, E75 A0 exon sequences were fused to sequences of a nearly full-length E75 A cDNA, and E75 B1 exon sequences were fused to sequences of a nearly full-length E75 B cDNA. These cassettes were cloned into pGEM3 (Promega), and transcripts of the open reading frames were prepared using T7 polymerase. These were then translated in the presence of $^{35}$S-methionine, and shown to give rise to proteins of appropriate size.

These cassettes have been placed into a variety of expression vectors, including pUCHsneo/Act for expression in Drosophila cells, pSV2 for expression in mammalian cells, and pOTS for expression in bacterial cells.

Methods

BamHI sites were introduced directly upstream of the initial ATGs of the E75A and 75B coding sequence—at the SspI site upstream of the E75A initial ATG, and at the SacII site upstream of the E75B initial ATG. cDNA and genomic sequences were joined at the EcoRV site in the A0 exon to construct an E75A cassette, and at the MluI in exon 3 to construct an E75B cassette.

EXAMPLE II

CLONING, STRUCTURE AND EXPRESSION OF THE EcR AND DHR3 GENES THAT ENCODE ADDITIONAL MEMBERS OF THE STEROID RECEPTOR SUPERFAMILY.

The following experiments were carried out after the primary structure of the E75 gene, and of the two members of the steroid receptor superfamily that it encodes, was determined (Experimental Example I). The purpose of these experiments was to clone and determine the primary structure of other steroid receptor superfamily genes from Drosophila, and of the proteins they encode, with the aim of identifying the gene that encodes a Drosophila ecdysone receptor, given that the characteristics of the E75 gene indicated that it did not encode an ecdysone receptor. The first stage of the experimental plan was to use the conserved sequences in the E75A transcription unit that encode the putative DNA-binding domain of the E75A receptor protein as a probe to screen a Drosophila genomic library of cloned DNA segments to identify segments containing sequences encoding the putative DNA-binding domains of other Drosophila members of the steroid receptor superfamily. The second stage was to isolate cDNA clones from the identified genes, as well as additional genomic DNA clones, to obtain the nucleotide sequence of the complete coding region (i.e., the open reading frame encoding the respective receptors) and the exon-intron organization of these genes.

The experiments described below resulted in the cloning and structural characterization of two genes that satisfy the criteria for bona fide members of the steroid receptor superfamily: encoding proteins that exhibit amino acid sequence homology to both the DNA-binding and the hormone-binding domains that are conserved among members of this superfamily. The two genes are called EcR and DHR3. The EcR gene was originally called DHR23, but was renamed EcR after it was shown to encode an ecdysone receptor (see Experimental Example III). The DHR3 designation stands for Drosophila Hormone Receptor 3.

A. Identification and Chromosomal Mapping of EcR and DHR3 Genomic clones

Initially, Southern blots of total Drosophila genomic DNA, digested with one or another of several restriction endonucleases, were probed with a 530 bp fragment of the E75A cDNA containing the sequences encoding the putative DNA-binding domain of the E75A receptor protein (see Experimental Example I) at low and high stringency hybridization conditions.

To isolate the sequences responsible for these low stringency bands, this E75A probe was used to screen a Drosophila genomic library under the same low stringency conditions, counter screening duplicate filters with E75 intron probes to eliminate phage-containing inserts from the E75 gene. Five genome equivalents were screened and 39 non-E75 containing phage were isolated. The 25 most strongly hybridizing clones were divided into six classes on the basis of restriction mapping and cross hybridization, each class containing a set of between one and six independent overlapping genomic inserts.

For each class, a restriction fragment containing the region of hybridization to the E75A probe was localized by Southern blotting. Hybridization of probes derived from these fragments to genomic Southern blots showed that each of the low stringency bands detectable by the E75A probe could be accounted for by one of the six isolated fragments.

The nucleotide sequences of the six restriction fragments were determine to test whether they represent candidate receptor genes. In all cases, DNA sequence similarities with the E75A probe were observed that are sufficient to account for the hybridization of these fragments with the probe. When the DNA sequences were conceptually translated in all six reading frames, four of the fragments yielded no significant sequence similarity with E75A at the protein level. The remaining two clones, however, showed predicted amino acid sequences with strong similarity to the DNA binding domains of the E75A protein and other steroid superfamily receptors.

These two clones represent the CR and DHR3 genes, as will become apparent. Probes from these clones were used to map the position of these genes in the polytene chromosomes by in situ hybridization. The EcR and DHR3 chromosomal loci were mapped to positions 42A and 46F, respectively, in the right arm of the second chromosome.

B. Structure of the EcR and DHR3 Genes and Their cDNAs

The DHR3 and EcR genomic clones described above were used to screen a cDNA library prepared from third instar tissues treated with ecdysone and cycloheximide. This allowed the isolation of a large number of cDNA clones since both genes have a peak period of transcription in late third instar after the rise in ecdysone titer. For each gene, 20 cloned cDNAs were purified and their lengths determined. Restriction maps for the 10 longest cDNAs from each gene were determined and found to be colinear.

For EcR, a 5534 bp cDNA sequence was obtained from two overlapping cDNA clones. It contains an 878 codon open reading frame (ORF) which yields a predicted amino acid sequence expected for a member of the steroid receptor superfamily (Table 2), as described in more detail below. The length of the largest DHR3 cDNA that was isolated (clone DHR3-9) is 4.2 kb. The nucleotide sequence of this cDNA was determined and found to contain a 487 codon AUG-initiated open reading frame (Table 3). As described below, the amino acid sequence of the DHR3 protein predicted from this sequence demonstrates that this protein is also a bona fide member of the steroid receptor superfamily.

TABLE 2

The cDNA sequence of the EcR gene.

Numerals at the left refer to the nucleotide sequences; those on the right to the amino acid sequence in the EcR protein. Nucleotides 1–5194 are the sequence of EcR-17 cDNA, while nucleotides 5195-5534 derive from the EcR-9 cDNA. The underlined sequences in the 5' and 3' untranslated regions refer, respectively, to the ATG codons and the AATAAA consensus polyadenylation signals. Positions of the introns and the donor and acceptor splice sequences are indicated above the cDNA sequence in small type. The amino acid sequences homologous to the conceived DNA-binding (C region) and hormone-binding (E region) domains of the steroid receptor superfamily are underlined.

```
EcR cDNA     5534 bp

1 GAATTCGGCAAAATACAGCACACACAATTGAAACGACAACCTAACAGTACGGTTTCCAAAGCACCTTACATTTCAAAACCGAAAACCCCCAAATGTTGTAACCAAATAATGTTTAAATCAC

125 ATATACACCTACATATATTTATGAAAAAATTGTTAGACAAATCCCAAATAATACCAGTCCCCCAACAACCAACAACACAAGTGCAATTCATCGGCAAAAATTAATATAAAGTGCAAATGCA

249 TTTGTGAAACTCAAACAATAGTAAAAATACATACATAAGTGGTGAAGAGCAAAAGGAAATAGTTCTTAAAATAACGCAAATCGAGAGCATATATTCATATTTGTACAGATATTATATGGC

373 GGCTGCATAGTGCAAACTGCGGGCTGAGGGAATACAGCGGTATCGAAATGTAAATAGGAAACAAACGAAGCCAGAACTCAAAACATCAGCAGTCGAAATCAAACATATCGACACAGACATAAGACGCCCGTCT

497 AGTCGTGGTCTGTGGAACGCTAGCTCCGCTTTGCCAGGAGCCGGAGACTTTTTCCGCATCCACAATATTACATATGTCGCGAGTAGTGCGGAGTCGAGTAGAGAGTGTGCCGTG

621 GATCCCGATCCCCTTACATATATAAAGGTAGTGAAAAGATTTTACTCAACATTCCAAATAGTGCTTTGTCAACTGGAATACCTTTTATTCAACTGGAATATCAAATACGCAGTGGGCCCATGGATACTTGTGGA

{gtgagt...v..ttacag}
 745 TTAGTAGCAGAACTGGGCACTATATCGACGCATATCGAACTGCTCTGATTGTTTCCCGCACTAAATGAGCAGGGATTCGGGCGAAAATGTATTTTGAACGCAACAAGTGCGCAAAAATACTAGCTCC 869 ACCACGAAACTGCACAAAACACCGCAGAAGCGAGCAGAACCTCGGGCGCGACGACGGAGCTTCGTAAAGCAACAGAGGATCTTACCAGGAGATAGCTCTTCTCCACATAGACCAACTGCCAGG 993 GACAAGCTCCTTGTCCCCAGCCAGCGCTAAGTGAACGGAAACGGCCACAAAACGGAAGCGCCGACTATCGGCTGCCAGAGG ATG AAG CGG CGC TGG TCG AAC AAC GGC GGC TTC ATG
                                                                                       Met Lys Arg Arg Trp Ser Asn Asn Gly Gly Phe Met   12

1105 CGC CTA CCG GAG GAG TCG TCC TCG GAG GTC TCC TCG AAC GGG CTC GTC CTG GTC CTG CCC TCG GGG GTG AAC ATG TCG CCC TCG CTG GAC
     Arg Leu Pro Glu Glu Ser Ser Ser Glu Val Ser Ser Asn Gly Leu Val Leu Val Leu Pro Ser Gly Val Asn Met Ser Pro Ser Leu Asp   43

1198 TCG CAC GAC TAT TGC GAT CAG GAC CTT TGG CTC TGC CTG TGC GAC GAG TCC GGT TCG TTT GGC GGC TCC AAC GGC CAT GGC CTA AGT CAG CAG CAG
     Ser His Asp Tyr Cys Asp Gln Asp Leu Trp Leu Cys Leu Cys Asp Glu Ser Gly Ser Phe Gly Gly Ser Asn Gly His Gly Leu Ser Gln Gln Gln   74

1291 CAG AGC GTC ATC ACG GTG GCC ATG CAC CTG CCC GCG CAG ACC ACC ATC ATT CCG ATC ATC CCG ATC ATT AAC GGC AAC GCA AAC GGA ATG
     Gln Ser Val Ile Thr Val Ala Met His Leu Pro Ala Gln Thr Thr Ile Ile Pro Ile Ile Pro Ile Ile Asn Gly Asn Ala Asn Gly Met   105

1384 GGA GGC TCC ACC AAT CAG GCG CAA TAT GTG CCG CCG GGT GCC ACT AAT CTG GGA GCG TTG GCC ATG GTC AAC CTC AAT GGG GGC TTC AAT GGA ATG CAG
     Gly Gly Ser Thr Asn Gln Ala Gln Tyr Val Pro Pro Gly Ala Thr Asn Leu Gly Ala Leu Ala Met Val Asn Leu Asn Gly Gly Phe Asn Gly Met Gln   136

1477 CAA CAG ATT CAG AAT GGC CAC GGC ATC ATC AAC TCC ACA ACG CCC TCA AAC CCG ACC ACC CCG CTC CAC CCG CTT CAG CAG AAC CTG CAG CAG GGC GCG
     Gln Gln Ile Gln Asn Gly His Gly Ile Ile Asn Ser Thr Thr Pro Ser Asn Pro Thr Thr Pro Leu His Pro Leu Gln Gln Asn Leu Gln Gln Gly Ala   167

1570 GGC GGC GGT GGC ATC GGG GGA ATG GGG ATG ATT CTT CAC CAC GCG AAT GGC ACC CCA AAT GGC CTT ATC GGA GTT GTG GGA GGC GGC GGC GGA GTA
     Gly Gly Gly Gly Ile Gly Gly Met Gly Met Ile Leu His His Ala Asn Gly Thr Pro Asn Gly Leu Ile Gly Val Val Gly Gly Gly Gly Gly Val   198
```

TABLE 2-continued

```
                                                                                                    {gtaaga..v..ggacag}
1663 GGT CTT GGA GTA GGC GGA GGC GGA GTG GGA GGC CTG GGA ATG CAG CAC ACA CCC CGA AGC GAT TCG GTG AAT TCT TCA GGT CGC GAT 229
     Gly Leu Gly Val Gly Gly Gly Gly Val Gly Gly Leu Gly Met Gln His Thr Pro Arg Ser Asp Ser Val Asn Ser Ser Gly Arg Asp 1756 GAT CTC TCG CCT TCG AGC AGC TTG AAC GGA TAC AGC GCG AAC GAA AGC TGC GAT AAG AAG AGC CTG AAG GGA CCT GCG CGG CCA CAA 260
     Asp Leu Ser Pro Ser Ser Ser Leu Asn Gly Tyr Ser Ala Asn Glu Ser Cys Asp Lys Lys Ser Leu Lys Gly Pro Ala Pro Arg Val Gln 1849 GAG GAG CTG TGC CTG GTT TGC CTC GGC GAC AGG CGC GCC TCC ACC CTC TAC CAC AAC GCC TAC CAC TGT GAG GGC TTC TTT CGA CGC AGC 291
     Glu Glu Leu Cys Leu Val Cys Leu Gly Asp Arg Arg Ala Ser Thr Leu Tyr His Asn Ala Tyr His Cys Glu Gly Phe Phe Arg Arg Ser 1942 GTT ACG AAG AGC GCC GTC TAC TGC TGC AAG TTC GGG CGC GCC TGC GAA ATG GAC ATG TAC ATG AGG CGA AAG TGT CAG GAG TGC CTG AAA 322
     Val Thr Lys Ser Ala Val Tyr Cys Cys Lys Phe Gly Arg Ala Cys Glu Met Asp Met Tyr Met Arg Arg Lys Cys Gln Glu Cys Leu Lys 2035 AAG CTG GCC GTG GGT ATG CGG CCG GAA TGC GTC GTC CCG GAG AAC CAA TGT GCG ATG AAG CGG CGC GAA AAG AAG GCC CAG AAG GAG AAG 353
     Lys Leu Ala Val Gly Met Arg Pro Glu Cys Val Val Pro Glu Asn Gln Cys Ala Met Lys Arg Arg Glu Lys Lys Ala Gln Lys Glu Lys 2128 GAC AAA ATG ACC ACT TCG CCG AGC TCT CAG CAT GGC AAT GGC CTT GCC TCT GGT GGC GGC GGT CAA GAC TTT GTT AAG AAG GAG ATT CTT 384
     Asp Lys Met Thr Thr Ser Pro Ser Ser Gln His Gly Asn Gly Leu Ala Ser Gly Gly Gly Gln Asp Phe Val Lys Lys Glu Ile Leu {gtaggg..v..gtacag}
2221 GAC CTT ATG ACA TGC GAG CCG CCC CAG CAT GCC ACT ATT CCG CTA CTA CCT GAT GAA ATA TTG GCC AAG TGT CAA GCG CGC AAT ATA CCT TCC 415
     Asp Leu Met Thr Cys Glu Pro Pro Gln His Ala Thr Ile Pro Leu Leu Pro Asp Glu Ile Leu Ala Lys Cys Gln Ala Arg Asn Ile Pro Ser {gtgggt..v..ttgcag}
2314 TTA ACG TAC AAT CAG TTG GCC GTT ATA TAC AAG TTA ATT TGG TAC CAG GAC CAG ATC ACG GAG ATA CTC AGG GAT CTC AGG CGT ATA ATG 446
     Leu Thr Tyr Asn Gln Leu Ala Val Ile Tyr Lys Leu Ile Trp Tyr Gln Asp Gln Ile Thr Glu Ile Leu Arg Asp Leu Arg Arg Ile Met 2407 AGT GCT GAT GAG AAC GAG AGC CAA GAG CAA ACG GAC GTC AGC TTT CGG CAT ATA ACC GAG ATA CTC ACG GTC CAG TTG ATT GTT GAG TTT 477
     Ser Ala Asp Glu Asn Glu Ser Gln Glu Gln Thr Asp Val Ser Phe Arg His Ile Thr Glu Ile Leu Thr Val Gln Leu Ile Val Glu Phe {gtgagt..v..cgttag}
2500 GCT AAA GGT CTA CCA GCG TTT ACA AAG ATA CCC CAG GAG CAG ATC ACG TTA CTA AAG GCC TGC TCG TCG GAG GTG ATG ATG CTG CGT ATG 508
     Ala Lys Gly Leu Pro Ala Phe Thr Lys Ile Pro Gln Glu Gln Ile Thr Leu Leu Lys Ala Cys Ser Ser Glu Val Met Met Leu Arg Met 2593 GCA CGA CGC TAT GAC CAC AGC TCG GAC TCA ATA TTC TTC GCG AAT AAT AGA TCA TAT ACG CGG GAT TCT TAC AAA ATG GCC GGA ATG GAT 539
     Ala Arg Arg Tyr Asp His Ser Ser Asp Ser Ile Phe Phe Ala Asn Asn Arg Ser Tyr Thr Arg Asp Ser Tyr Lys Met Ala Gly Met Asp 2686 AAC ATT GAA GAC CTG CTA CAT TTC TGC CAA ATG TTC TCG ATG GTG GAC AAC GTC GAA TAC GCG CTT CTC ACT GCC ATT GTG GCT TTC 570
     Asn Ile Glu Asp Leu Leu His Phe Cys Gln Met Phe Ser Met Val Asp Asn Val Glu Tyr Ala Leu Leu Thr Ala Ile Val Ala Phe 2779 TCG GAC CGG CCG GGC CTG GAG AAG GCC CAA GTC GAA GCG ATC CAG AGC TAC TAC ATC GAC ACG CTA CGC ATT TAT ATA CTC AAC CGC CAC 601
     Ser Asp Arg Pro Gly Leu Glu Lys Ala Gln Val Glu Ala Ile Gln Ser Tyr Tyr Ile Asp Thr Leu Arg Ile Tyr Ile Leu Asn Arg His
```

TABLE 2-continued

| | | | | | | | | | | | | | | | | | |
|---|---|---|---|---|---|---|---|---|---|---|---|---|---|---|---|---|---|
| 2872 | TGC | GGC | GAC | TCA | ATG | AGC | CTC | GTC | TTC | TAC | GCA | AAG | CTG | CTC | TCG | ATC | CTC | ACC | GAG | TTC | CGT | ACG | CTG | GGC | AAC | CAG | AAC | GCC | GAG | ATG | TGT |
| | Cys | Gly | Asp | Ser | Met | Ser | Leu | Val | Phe | Tyr | Ala | Lys | Leu | Leu | Ser | Ile | Leu | Thr | Glu | Phe | Arg | Thr | Leu | Gly | Asn | Gln | Asn | Ala | Glu | Met | Cys 632 |
| 2965 | TTC | TCA | AAG | CTA | AAG | AAC | CGC | AAA | AAC | GAG | GAG | AAC | GAG | TTC | CTC | GAG | GAG | ATC | TGG | GAC | GTT | CAT | GCC | ATC | CCG | CCA | TCG | GTC | CAG | TCG | CAC | CTT |
| | Phe | Ser | Lys | Leu | Lys | Asn | Arg | Lys | Asn | Glu | Glu | Asn | Glu | Phe | Leu | Glu | Glu | Ile | Trp | Asp | Val | His | Ala | Ile | Pro | Pro | Ser | Val | Gln | Ser | His | Leu 663 |
| 3058 | CAG | ATT | ACC | CAG | GAG | GAG | AAC | GAG | CGT | CTC | GAG | CGG | GCT | GAG | CGT | ATG | CGG | GCA | TCG | GTT | GGG | GGC | GCC | ATT | ACC | GCC | GGC | ATT | GAT | TGC | GAC |
| | Gln | Ile | Thr | Gln | Glu | Glu | Asn | Glu | Arg | Leu | Glu | Arg | Ala | Glu | Arg | Met | Arg | Ala | Ser | Val | Gly | Gly | Ala | Ile | Thr | Ala | Gly | Ile | Asp | Cys | Asp 694 |
| 3151 | TCT | GCC | TCC | ACT | TCG | GCG | GCG | GCA | GCC | GCG | CAG | CCT | CAG | CCT | CAA | CCC | TCC | TCC | CTG | ACC | CAG | CTC | CAA | CCA | CAG | CTT | CAG | ACG | GAT | TCC |
| | Ser | Ala | Ser | Thr | Ser | Ala | Ala | Ala | Ala | Ala | Gln | Pro | Gln | Pro | Gln | Pro | Ser | Ser | Leu | Thr | Gln | Leu | Gln | Pro | Gln | Leu | Gln | Thr | Asp | Ser 725 |
| 3244 | CAG | CAG | CAG | ACA | CAG | ATT | CAA | CAG | CCA | CAG | CCG | CAG | CTG | CAA | GGT | CAA | CTG | CAA | CCC | CAG | CTC | CAA | CCA | CAG | CTT | CAG | ACG | CAA |
| | Gln | Gln | Gln | Thr | Gln | Ile | Gln | Gln | Pro | Gln | Pro | Gln | Leu | Gln | Gly | Gln | Leu | Gln | Pro | Gln | Leu | Gln | Pro | Gln | Leu | Gln | Thr | Gln 756 |
| 3337 | CTC | CAG | CCA | CAG | ATT | CAA | CAG | CCA | CAG | CTC | TCC | GCT | CCC | GTC | CCC | GTA | ACC | GCA | CCT | GGT | TCC | TTG | TCC | GCG | GTC |
| | Leu | Gln | Pro | Gln | Ile | Gln | Gln | Pro | Gln | Leu | Ser | Ala | Pro | Val | Pro | Val | Thr | Ala | Pro | Gly | Ser | Leu | Ser | Ala | Val 787 |
| 3430 | AGT | ACG | AGC | AGC | GAA | TAC | ATG | GGC | GGA | AGT | GCG | GCC | ATA | GGA | CCC | ATC | ACG | ACC | AGT | ATC | GCC | GTT | ACC | GCT | AGC |
| | Ser | Thr | Ser | Ser | Glu | Tyr | Met | Gly | Gly | Ser | Ala | Ala | Ile | Gly | Pro | Ile | Thr | Thr | Ser | Ile | Ala | Val | Thr | Ala | Ser 818 |
| 3523 | TCC | ACC | ACA | GCG | ATC | ACC | GGT | GTT | GGA | ATG | GGC | AAC | GTC | AGC | ATG | TAT | GCG | AAC | GCC | CAG | ACG | GCG |
| | Ser | Thr | Thr | Ala | Ile | Thr | Gly | Val | Gly | Met | Gly | Asn | Val | Ser | Met | Tyr | Ala | Asn | Ala | Gln | Thr | Ala 849 |
| 3616 | ATG | GCC | TTG | ATG | GGT | GTA | GCC | CTG | CAT | TCG | CAC | CAA | GAG | CAG | CTT | AAG | TCG | GAG | CAC | TCG | ACG | GCT | GCA | TAG | — |
| | Met | Ala | Leu | Met | Gly | Val | Ala | Leu | His | Ser | His | Gln | Glu | Gln | Leu | Lys | Ser | Glu | His | Ser | Thr | Thr | Ala | — | 878 |

3709 GCGCAGAGTCAGCTCCACCAACATCACCACCACAACATCGACGTCCTGCTGAGTAGAAGGCAGCTGAACCCACAGACATAGGGGAAATGGGGAAGTTCTCTCCAGAGAGTTCGAGCCGA

3833 ACTAAATAGTAAAAATGTAAAAATGGAATAACTAATGGACAAGCGTAAAATGCAGTTATTTAGTCTTAAGCCTGCAAATTAATCATATTATTCATACAAATATTACCTATTATTAATACAGCCTATTAACAATACG

3957 CTAAAGCTTAATTGAAAAAGCTTCAACAACAATTGGACAAACGCGTTGAGGAACCGGAGAAAATTTAGAACATGTTGATCTCCAAACTGATGCATGGGCAAACAGAGTAACAGGATAGGGCGTGAACAGGGAAGAGAGA

4081 TGTATGTCGCATCAGATCTCACGATCAATTCTGAATTTGTTAACTAAATGACTAACTCTAAACGTAATGAAAGCAACTCATTTAAAGTAATTAAAACCACTTTTAAAACGCAAAACTTAATTCTTAATTTATGATTCTTATAAATA

4205 AGAGAATAAAGATTGTTTATATTTAAAAAATAATGATAATAACATTATCATCCACCATAATTAAAATAACAACATAATTACAAAAAACAAATAAAAATAATTAAAAAAACACTTTTAAAACACGAGAATTTAAATTCTTAAATTTAATAATT

4329 AATTCTGTTAAATGAAATCATAAAGAAAGGCAACCTGAAAAAACTTATTATTATTGGCATGTTTTTCAAAAAAACTTTGATATTGAAACTAAACAAAGGATAATGAAATGAAAGTGATTGGAGTCTTAC

4453 TTTTTTAATCATAAAGAAAGGCAACCTGAAAAAACTTATTATTATTGGCATGTTTTTCAAAAAAACTTTGATATTGAAACTAAACAAAGGATAATGAAATGAAAGTGATTGGAGTCTTAC

4577 CATCCAAAAATATTAGCCAGCAGCATCAAAAGGTATTATTAAATTAAAAATCTAATTTCGAGTTCAAGAAAACACTTTTTGGTGGAAAATAGTTTTCAATCACTTTGATAAAAACCACACAAATTAATAAA

4701 TCAAAAACCAAAAGGCATCAAAAGGTATTATTAAATTAAAAATCTAATTTCGAGTTCAAGAAAACACTTTTTGGTGGAAAATAGTTTTCAATCACTTTGATAAAAACCACACAAATTAATAAA

TABLE 2-continued

```
4825 TACATGCATACACCAAAAGACTTCAATATATATTTTAAAATTTACATTGATAATTCGAAATTGAATAAGAATCACATCCATCTAATTGGCTAAATCAAAATTTTATGAAAGCACACAA
4949 AAACGTGCAAATTTGTTTACTTTGGCAATTTGTATGTTATACAAAATTGATTTTCAAAATAATTTATTAGATTGTATTAGTTTCATTTGCTTTCATTTGGATGTACATTT AAATA
5073 AATTTACTTTAAATGTTGGCCTTATTTAACTTAAATCAAATTTATTCAAATTCAAATTTATTCTCAATTTAGTAAAAAAAAATGTGTTAAGAACACTGTAAAATATT AATAAAAATTAAAGTT
5197 TAAAGTGATTCTTTATATGTAAAAGAAGACAAAAATATCTTCTACGTAGCTTTCTACTGAATTGTGCAATTTTTTACTTTTACTTTTGTATAATGACGAACTAAAATTGTATAAATT ACACACGCAT
5321 ACACACGCATACACACGCTACACATACAGCCACATATTTTTAATTTTAAGTCAACCTATTTATAAATATGAATTTGTATATGACGAACTAAAATTGTATATGACGAACTAAAATTAGCATGACATCATGGACATACTTGGA
5445 AATAACTCTATCAAACGAGCTAAATGCATTGAAGAAGAAAAATTCTTGTTAAATATAGTCTGCACTTCGACAAACGAAAATCAGTGAATTC

EcR cDNA       5534 bp

1 GAATTCGGCAAAATACAGCACACACAATTGAAACGACACCTGTTTCCCAAAGCACCTTACATTTCAAAACGAAAACCCCCAAAATGTTGTAACCAAATAATGTTTAAATCAC
125 ATATACACCTACATATATTTATGAAAAATTGTTAGACAAATCCCAACAACCGCAACAACACAGTGCAATTCATCGGCAAAAATATAATATAAAGTGCAAATGCA
249 TTGTAGCTGAAACTCAAACAATAGTAAAAATACATAAGTGGTGAAGAAGCAAAAGGAAATAGTTCTTAAAATCGAGAGCATATATTTGTACAGATATATATGGC
373 GGCTGCATAGTGCAAACTGCGGCTGAGGGAATACAGCGGTATCGAAATGTAAATAGGAAAACAACCAGAACTGAAATCAACATATCAGCAACGTGACACACAGACATAAGACGCCGTCT
497 AGTCGTGGTCTGTGGAACGCTAGTCCGCTTTGCCAGGAGCCGAGACTTTTACTCAAGATTACTACATAATGTCTTGTCAACTGAATACCTTTTATTCAAATACGCAGTGAGTGGGCCATGGATACTTGTGGA
621 GATCCCGATCCCCTTACATATATAAAGGTAGTGAAAGATTTTGAAAGATTCGGGCAGGGATTCGGGCGAAAATGTATTTTGAACGCAAACAAGTGCGCAAAAAATACTAGCTCC
745 TTAGTAGCAGAACTGGCGCACTACTATCGACGCATATCGACGCATATCGACAGAGATCTTAACGAGCAGGAGCATTCGTAAAGCAACAGAGATCTTAACGAGCAGGAGCATAGCAACAGATAGCCTCTTCTCCACATAGACCAACTGCCAGG
        {gtgagt..v..ttacag}
869 ACCACGAAACTGCACAAAAACACCGCCAGAAGCGAGCAGAACCTCGGGCGCGAGCCGAGCTTCGTAAAGCAACAGAGATCTT
993 GACAAGCTCCTTGTCCCCAGCCGACGCTAAGTGAACGGAAAAACGGCAGCACAAAAACGGCAGCACAAAAACGGCGAAAAACGGCGA
1105 CGC CTA CCG GAG GAG TCG TCC TCG GAG GTC ACG TCC TCC AAC GGG CTC GTC CTG CCC TCG GGG GTG AAC ATG TCG CCC TCG TCG GAC
     Arg Leu Pro Glu Glu Ser Ser Ser Glu Val Thr Ser Ser Ser Asn Gly Leu Val Leu Pro Ser Gly Val Asn Met Ser Pro Ser Ser Asp   43
                                                                                                                    Met Lys Arg Arg Trp Ser Asn Asn Gly Gly Phe Met  12
1198 TCG CAC GAC TAT TGC GAT CAG GAC CTT TGG CTC TGC GGC AAC GAG TCC GGT TCG TTT GGC GGC TCC GGC CAT GGC CTA AGT CAG CAG CAG
     Ser His Asp Tyr Cys Asp Gln Asp Leu Trp Leu Cys Gly Asn Glu Ser Gly Ser Phe Gly Gly Ser Gly His Gly Leu Ser Gln Gln Gln    74
1291 CAG AGC GTC ATC ACG CAC GCC ATG CAC CTG GCC ATG GGG TGC TCC AGC AGC TCC ACT AAT CTG CCC GCG GCG TTG GCC AAC GGG ATG CTC AAT GGG GGC TTC AAT GGA ATG CAG
     Gln Ser Val Ile Thr His Ala Met His Leu Ala Met Gly Cys Ser Ser Ser Thr Asn Leu Pro Ala Gln Thr Thr Ile Pro Ile Asn Ala Asn Gly Asn Gly Gly Phe Asn Gly Met Gln  105
1384 GGA GGC TCC ACC AAT GGC CAA TAT GTG CCG GGT GCC ACT AAT CTG GGA GCG TTG GCC AAC GCG ATG CTC AAT GGG GGC TTC AAT GGA ATG CAG
     Gly Gly Ser Thr Asn Gly Gln Tyr Val Pro Gly Ala Thr Asn Leu Ala Asn Gly Met Leu Asn Gly Phe Asn Gly Met Gln  136
1477 CAA CAG ATT CAG AAT GGC CAC GGC CTC ATC AAC TCC ACA ACG CCC TCA ACG CCC ACC ACC CCG CTC CAC CTT CAG CAG AAC CTG GGG GGC GCG
     Gln Gln Ile Gln Asn Gly His Gly Leu Ile Asn Ser Thr Thr Pro Ser Thr Pro Thr Thr Pro Leu His Leu Gln Gln Asn Leu Gly Gly Ala
```

TABLE 2-continued

```
      Gln Gln Ile Gln Asn Gly His Gly Leu Ile Asn Ser Thr Thr Pro Ser Thr Thr Pro Leu His Leu Gln Gln Asn Leu Gly Gly Ala   167
1570  GGC GGC GGT ATC GGG GGA ATG GGT ATT CTT CAC CAC GCG AAT CCA AAT GGC ACC CCA ACT ACT CCG CTT CAT CTG CAG CAG AAT CTT GGA GGT GGA GGC GTA
      Gly Gly Gly Ile Gly Gly Met Gly Ile Leu His His Ala Asn Pro Asn Gly Thr Pro Thr Thr Pro Leu His Leu Gln Gln Asn Leu Gly Gly Gly Val   198
                                                                                                                                            {gtaaga...v...ggacag}
1663  GGT CTT GGA GTA GGC GGA GGC GGA GTG GGA GGC CTG GGA GGC TAC TCG GCG AAC GAA AGC AAG AAG AGC CTG AAT TCT ATA TCA GGT CGC GAT
      Gly Leu Gly Val Gly Gly Gly Gly Val Gly Gly Leu Gly Gly Tyr Ser Ala Asn Glu Ser Lys Lys Ser Leu Asn Ser Ile Ser Gly Arg Asp   229
1756  GAT CTC TCG CCT TCG AGC AGC TTG AAC GGA TAC CAC CAC TCC GGC GAC AGG TGC AAG GGG TGC AAG GGG TTC TTT CGA CGC AGC
      Asp Leu Ser Pro Ser Ser Ser Leu Asn Gly Tyr His His Ser Gly Asp Arg Ala Pro Ala Pro Arg Val Gln
1849  GAG GAG CTG TGC CTG GTT TGC GTG GCC AAG AGC GCC GTC TAC TGC TGC GGG CGC GCC ATG GAC CGA ATG ATG AGG AGG ATG ATG AGG CGA AAG TGT CAG GAG CTG AAA
      Glu Glu Leu Cys Leu Val Cys Val Ala Lys Ser Ala Val Tyr Cys Cys Gly Arg Ala Cys Met Asn Met Tyr Met Arg Arg Lys Cys Gln Glu Cys Arg Leu Lys   322
1942  GTT ACG AAG GCC GTC TTC TGC TGC GGG CGC GCC ATG GAC CGA ATG ATG AGG CGA AAG TGT CAG GAG CTG AAA
      Val Thr Lys Ser Ala Val Tyr Cys Cys Gly Arg Ala Cys Met Asn Met Tyr Met Arg Arg Lys Cys Gln Glu Cys Arg Leu Lys   322
2035  AAG TGC CTG GCC GTG GGT ATG CGG GAA TGC GTC CCG GAG GTC GTC GAG AAC GGC AGC CTG AAT CTG TGT GAT GAG AGC AAG CTG TGT AAG AAG CAG AAG CTT
      Lys Cys Leu Ala Val Gly Met Arg Glu Cys Val Pro Glu Val Val Glu Asn Gln Asn Cys Ala Met Lys Arg Arg Glu Lys Leu Ala Gln Lys Glu Lys   353
                                                                                                                                            {gtaggg...v...gtacag}
2128  GAC AAA ATG ACA ACT TCG CCC AGC TCT CAG CAT GGC GGT GGG CTT TCG GGT GGG GGA GGA CAA GAC TTT GTT AAG AAG GAG ATT CTT
      Asp Lys Met Thr Thr Ser Pro Ser Ser Gln His Gly Gly Gly Leu Ser Gly Gly Gly Gly Gln Asp Phe Val Lys Lys Glu Ile Leu   384
2221  GAC CTT ATG ACA TGC GAG CCG CCA CCC CAG CAT GCC ACT ATT CCG CTA CTA CCT GAT GAA ATA TTG GCC AAG TGT CAA GCG CGC AAT ATA CCT TCC
      Asp Leu Met Thr Cys Glu Pro Pro Pro Gln His Ala Thr Ile Pro Leu Leu Pro Asp Glu Ile Leu Ala Lys Cys Gln Ala Arg Asn Ile Pro Ser   415
                                                                                                                                            {gtgggt...v...ttgcag}
2314  TTA ACG TAC AAT CAG GTT ATA TAC AAG TTA ATT TGG TAC CAG GAT GGC TAT GAG GAC CTC GAA GAG GAT CTC CAG GGT CGT ATA ATG
      Leu Thr Tyr Asn Gln Val Ile Tyr Lys Leu Ile Trp Tyr Gln Asp Gly Tyr Glu Asp Leu Glu Glu Asp Leu Gln Gly Arg Ile Met   446
2407  GAC CAA CCC GAG GAG AAC GAG AGC CAA GAG GAC GTC AGC GAC CAT ATA ACC GAG ATA CTC ACG ATA CTC ACG ATC ACG GTC CAG TTG ATT GTT GAG TTT
      Asp Gln Pro Glu Glu Asn Glu Ser Gln Glu Asp Val Ser Asp His Ile Thr Glu Ile Leu Thr Ile Leu Thr Val Gln Leu Ile Val Glu Phe   477
                                                                                                                                            {gtgagt...v...cgttag}
2500  GCT AAA GGT CTA ACG GCT TTT ACA AAG ATA CCC CAG GAG GAC CAG ATC ACG TTA CTA AAG GCC TGC TCG TCG TGC TCG TAC AAA ATG CTG ATG CGT ATG
      Ala Lys Gly Leu Thr Ala Phe Thr Lys Ile Pro Gln Glu Asp Gln Ile Thr Leu Leu Lys Ala Cys Ser Ser Glu Val Met Met Leu Arg Met   508
2593  GCA CGA CGC TAT GAC CAC AGC TCG GAC TCA ATA TTC TTC GCG AAT TCA TAT ACG CGG GAT TCT TAC AAA ATG GCC GGA ATG GCT GAT
      Ala Arg Arg Tyr Asp His Ser Ser Asp Ser Ile Phe Phe Ala Asn Ser Tyr Thr Arg Asp Ser Tyr Lys Met Ala Gly Met Ala Asp   539
```

TABLE 2-continued

```
2686 AAC ATT GAA GAC CTG CTG CAT TTC TGC CGC CAA ATG TTC TCG AAG GTG GAC AAC GTC GAA TAC GCG CTT CTC ACT GCC ATT GTG ATC TTC  570
     Asn Ile Glu Asp Leu Leu His Phe Cys Arg Gln Met Phe Ser Lys Val Asp Asn Val Glu Tyr Ala Leu Leu Thr Ala Ile Val Ile Phe

2779 TCG GAC CGG CCG GGC CTG GAG AAG CTG CAA CTA GTC TTC GAA GCG ATC TAC ATC CAG AGC TAT TAT ATA CTC AAC CGC CAC  601
     Ser Asp Arg Pro Gly Leu Glu Lys Leu Gln Leu Val Phe Glu Ala Ile Tyr Ile Gln Ser Tyr Tyr Ile Leu Asn Arg His

2872 TGC GAC GGC TCA ATG AGC CTC GTC TTC TAC GCA AAG CTG CTC ATC CTC GAG CTG CGT ACC GAG CTG GGC AAC CAG AAC GCC GAG ATG TGT  632
     Cys Gly Asp Ser Met Ser Leu Val Phe Tyr Ala Lys Leu Leu Ile Leu Glu Leu Arg Thr Glu Leu Gly Asn Gln Asn Ala Glu Met Cys

2965 TTC TCA CTA AAG CTC AAA AAC CGC AAA CTG CCC AAG TTC CTC GAG GAG ATC TGG GAC GTT CAT GCC ATC CCG TCG CAG TCG CAC CTT  663
     Phe Ser Leu Lys Leu Lys Asn Arg Lys Leu Pro Lys Phe Leu Glu Glu Ile Trp Asp Val His Ala Ile Pro Ser Val Gln Ser His Leu

3058 CAG ATT ACC CAG GAG AAC GAG CGT CTC GAG GCT ATG CGG GCA TCG GTT GGG GGC GCA ATT ACC GGC ATT GAT TGC GAC  694
     Gln Ile Thr Gln Glu Asn Glu Arg Leu Glu Ala Met Arg Ala Ser Val Gly Gly Ala Ile Thr Gly Ile Asp Cys Asp

3151 TCT GCC TCC ACT TCG GCG GCG GCA GCC GCG CAG CCT CAG CCT CAG CTA CAA CCT CAG GTT CAA CCC CAG CTC CAA CCA CAG CAA GAT TCC  725
     Ser Ala Ser Thr Ser Ala Ala Ala Ala Ala Gln Pro Gln Pro Gln Leu Gln Pro Gln Val Gln Pro Gln Leu Gln Pro Gln Gln Asn Asp Ser

3244 CAG CAC CAG ACA CAG CCG CAG CTA CAA CAG CCA CAG CTC CTT CCC GCC ATA GGA CCC TCC GTA ACC GCA CCT GGT TCC TTG TCC GCG CAA  756
     Gln His Gln Thr Gln Pro Gln Leu Gln Gln Pro Gln Leu Leu Pro Ala Ile Gly Pro Ser Val Thr Ala Pro Gly Ser Leu Ser Ala Gln

3337 CTC CAG CCA CAG ATT CAA CCA CAG CTC CTT CCC GTG CCC TCC GTA ACC AGT ATC ACG GCT GCC GTT ACC GCT AGC  787
     Leu Gln Pro Gln Ile Gln Pro Gln Leu Leu Pro Val Pro Ser Val Thr Ser Ile Thr Ala Ala Val Thr Ala Ser

3430 AGT ACG AGC AGC GAA TAC ATG GGC GGA AGT GCG GCC ATA GGA CCC ATC ACG CCG GCA ACC ACC AGT ATC ACG GCT GCC GTT ACC GCT AGC  818
     Ser Thr Ser Ser Glu Tyr Met Gly Gly Ser Ala Ala Ile Gly Pro Ile Thr Pro Ala Thr Thr Ser Ile Thr Ala Ala Val Thr Ala Ser

3523 TCC ACC ACA TCA GCG GTA CCG ATG GGC AAC GGA GTT GGA GTC GGT GTT GGG GTG GGC GGC AAC GTC ATG TAT GCG AAC GCC CAG ACG GCG  849
     Ser Thr Thr Ser Ala Val Pro Met Gly Asn Gly Val Gly Val Gly Val Gly Val Gly Gly Asn Val Met Tyr Ala Asn Ala Gln Thr Ala

3616 ATG GCC TTG GCC GTA CCG CAT TCG CTG CTC CAC CAA CAG CAG CTT ATC GGG GGA GTG GCG GTT AAG TCG ACG ACT GCA TAG CAG  878
     Met Ala Leu Ala Val Pro His Ser Leu Leu His Gln Gln Gln Leu Ile Gly Gly Val Ala Val Lys Ser Thr Thr Ala —

3709 GCGCAGAGTCAGCTCCACCAACATCACCACCACAACATCGACGTCCTGCTGCTGAGTAGAAAGCGCAGCTGAACCGACAGACATAGGGGAAATGGGGAAGTTCTCTCCAGAGAGTTCGAGCCGA

3833 ACTAAATAGTAAAAAGTGAATAACTATTGGACAAGCGTAAAATGCAGTTATTAGTCTTAAGCCTGCAAATATTCATACAAATATTCATACAAATATATTCATAATACACACCTATTAACAATTACG

3957 CTAAAGCTTAATGAAAAAGCTTCAACAACAATTGGAGGAACCGGAGAAAATTGATCCTCCAAACTGCATGCGAAAACAGATCAGAAAAGAACAGAACAGTAGGGCGTGAACAGACGTAGGGCGT

4081 TGTATGTCGCATCAGATCACGATCAATTCTCTGAATTTGTTAACTAAATGATCCTCCAAACTGCATGCGAAAACAGATCAGAAAAGAACAGAACAGTAGGGCGTGAACAGACGTAGGGCGT

4205 AGAGAATAAAGATTGTTTATATTTAAAAAATATATAAAATAATTACTAACTACTAACTCTAAACGTAATGAAAGCAACTACTATCTAACTAATATCTAACTATAATCGTCGTACTCGTAGGGAAGTGAGAA
```

TABLE 2-continued

4329 AATCTGTT AAAT GAA CAAAAAT AAT GAT AAT AACATT AT CAT CCACCAT AAT T AAAAT CATT T AAAGT AAT T AAAAACAAAACACTT T T AAAACACGCAAAACTT GGACTGAT T T AT AAAT A

4453 TTTTTT AAT CAT AAAGAAAGGCAACCTGAAAAAAAT ATT ACAAAAAAT AAC AACAT ATT T ATT AT GACACCCT T AT AT GT T T T CAAAACGAGAATT T AAAT TCT T AGATT CTT AT AAT TT

4577 CAT CCAAAAAT ATT AGCCAGCAAAAACCTT T ATT AT GGCAT GTTTTT T AGACAT GT T T T CAAAAAAACTT T GAT ATT GAAACT AAACAAAGGAT AAT GAAAT GAAAGT GAT T GGAGT CTT AC

4701 TCAAAAACCAAAAGGCAT CAAAAGGT ATT AAAAAT AT AAT CT AAT T T CGAGT T CAAGAAACACT T T T TGGT GGAAAAT AGT T T T CAAT CACT TT GAT AAAAACCACACAAAT T AAT AAA

4825 TACATGCAT ACACCAAAAGACTT CAAT AT AT ATT T T AAAATT ACAT T GAT AATT CGAAAT T GAAT AAGAAT CACAT CCAT CT AAT T T GGCT AAT T T AGT T AGT T CAT T T GCT T GGGAT GT ACATT T T AT GAAAGCCACACAA

4949 AAACGTGCAAAT T T GT T T ACT T T GGCAATTT T T AT GT T AT ACAAAATT T AT GCAAAT T T GAT TT T CAAAAT T AT T CT AAT T T AT T CTAATT T AGT AAAAAAAAT GT GT T T AAAAT T GAAAAT AAGAACACTGT AAAAT ATT <u>AAT AAAAAAT T AAAGT T</u>

5073 AATTTT ACTT TAAAT TGT T GGCCT T ATT T T AACT T AAAT CAAAT T T ATT CT AAT T T T ACTTTTT ACT T T T ACT T T T ACT AAT CCT AAT T AAT T T ACACACGCAT

5197 T AAAGT GAT T CT T T AT AT GT AAAAAGAAGACAAAAAT ATCTTACGT AGCT T T CT ACT GAAT T GT GCAATT T T T T ACT T T ACT T T AT CT AAT T GT AAT GACGAACT AAAAT T AGCATGACATCAT GGACAT ACTT GGA

5321 ACACACGCAT ACACACGCCT ACACAT ACAGCCCAT ATT T T T AAT T T T AAGT CAACCT AATT T AT AAT AT GAATT T GT AT AAT GACGAACT AAAAT T GT AAT AT AGCATGACATCAT GGACAT ACTT GGA

5445 AAT AACTCT AT CAAACGAGCT AAAT GCATT GAAGAAGAAAAT T CT T GT T AAAT AT AGT CT GCACTT CGACAAACGAAAAT CAGT GAATT C

TABLE 3

The cDNA sequence of the DHR3 gene.

The numbering and underlining of the nucleotide and amino acid sequences have the same meaning as in TABLE 2, and the intron positions and donor and acceptor splice sequences are similarly indicated. The sequence of the 5' proximal 2338 nucleotides of the DHR3-9 cDNA is shown. The sequence of the remainder of this 4.2 kb cDNA was determined for only one strand and is not shown. Four silent, third-position differences between the cDNA and genomic DNA sequences are indicated above the cDNA sequence.

```
cDNA DHR3-9    4.2 kb

1 GAATTCATTCAACTGCAAAGAGCAGCCAAATTGCGCATACGCCGCCGTATGGCCGGTGAGTGCCCGTGTTCATCAGCGGTTGCATCAACTGATACCAAGTGTACATAACTACAGCTACAA                                              5
 125 TTGCAACTATTTCACCAATCAACGCAGCGGCAACAACATCAGCAACGCACCGCAAACGTTGAAACGTTCCCACTAATAATT  ATG TAT ACG CAA CGT                                                              36
                                                                                    MET Tyr Thr Gln Arg

242 ATG TTT GAC ATG TGG AGC AGC GTC ACT TCG AAA CTG GAA GCA CAC GCA AAC AAT CTC GGT CAA AGC AAC GTC CAA TCG CCG GCG GGA CAA AAC     67
     MET Phe Asp MET Trp Ser Ser Val Thr Ser Lys Leu Glu Ala His Ala Asn Asn Leu Gly Gln Ser Asn Val Gln Ser Pro Ala Gly Gln Asn
                                                   {gtaaag..v..tcacag}
 335 AAC TCC AGC GGT TCC ATT AAA GCT CAA ATT GAG ATA ATT CCA ATC TGC AAA GTC TCA TCC GGC GTG CAT TAC GGA GTG ATC ACC                 98
     Asn Ser Ser Gly Ser Ile Lys Ala Gln Ile Glu Ile Ile Pro Ile Cys Lys Val Ser Ser Gly Val His Tyr Gly Val Ile Thr 428 TGC GAG GGC TGC AAG GGA TTC TTT CGA AGA TCG CAA TCC GTC CAA TAC CAG TGT CCG CGC AAC AAG CAA TCC GTG GTG GAC CGT GTT             129
     Cys Glu Gly Cys Lys Gly Phe Phe Arg Arg Ser Gln Ser Val Gln Tyr Gln Cys Pro Arg Asn Lys Gln Ser Val Val Asp Arg Val
                                                                                                        {gtctgt..v..ttgcag}
 521 AAT CGC AAC CGA TGT CAA TAT TGT AGA CTG CAA AAG TGC CTA AAA CTG GGA ATG AGC CGT GAT GCT GTA AAG TTC GGC AGG ATG TCC AAG AAG    160
     Asn Arg Asn Arg Cys Gln Tyr Cys Arg Leu Gln Lys Cys Leu Lys Leu Gly MET Ser Arg Asp Ala Val Lys Phe Gly Arg MET Ser Lys Lys 614 CAG CGC GAG AAG GTC GAG GAC GTA CGC TTC CAT CGG GCC GCA CAA AGC GCA GCA GCA ALA GCA CCG GAT AGC TCC GTA TAC TCC GAT ACA         191
     Gln Arg Glu Lys Val Glu Asp Val Arg Phe His Arg Ala Ala Gln Ser Ala Ala Ala Ala Pro Asp Ser Ser Val Tyr Ser Asp Thr
                                               {gtgcag..v..actcag}
 707 CAG ACG CCC TCG AGC AGC GAC CAG CTG CAT CAC AAC AAT TAC AAC AGC TAC AGC GGC GGC TAC AAC AAC GAG GTG GGC TAC GGC AGT CCC         222
     Gln Thr Pro Ser Ser Ser Asp Gln Leu His His Asn Asn Tyr Asn Ser Tyr Ser Gly Gly Tyr Asn Asn Glu Val Gly Tyr Gly Ser Pro 800 TAC GGA TAC TCG GCC TCC GTG ACG CCA CAG CAG TAC GAC ATC TCG GCG GAC TAC ACC ACC TAC GAG CCG CGC AGT                             253
     Tyr Gly Tyr Ser Ala Ser Val Thr Pro Gln Gln Tyr Asp Ile Ser Ala Asp Tyr Thr Thr Tyr Glu Pro Arg Ser
                                          {gtaaag..v..ctccag}   (C)
 893 ACA ATA ATC GAT CCC GAA TTT ATT AGT CAC CCG GAT ATA AAC GAT GTG CTG ATC AAG ACG CTG GAG GCG CAT GCC AAC ACA AAT                 284
     Thr Ile Ile Asp Pro Glu Phe Ile Ser His Pro Asp Ile Asn Asp Val Leu Ile Lys Thr Leu Ala Glu Ala His Ala Asn Thr Asn
                                                                     (G)
 986 ACC AAA CTG GAA GCT GTG CAC GAC ATG TTC CGA TCA CGC GAT GTG CCG CAG AAG CCG GTC CGC ATT CTC TAC TAC TAC AAG AAT CTG GGC CAA GAG GAA CTC TGG  315
     Thr Lys Leu Glu Ala Val His Asp MET Phe Arg Ser Arg Asp Val Pro Gln Lys Pro Val Arg Ile Leu Tyr Tyr Tyr Lys Asn Leu Gly Gln Glu Glu Leu Trp
                                              {gtgag..v..cctcag}
1079 CTG GAC TGC GCT GAG AAG CTT ACA CAA ATG ATA ATC GAA AAC ATA CAG AAC ATA ATC GAA TTT GCT AAG CTC ATA CCG GGA TTC ATG CGC CTG AGT CAG GAC GAT
     Leu Asp Cys Ala Glu Lys Leu Thr Gln MET Ile Ile Glu Asn Ile Gln Asn Ile Ile Glu Phe Ala Lys Leu Ile Pro Gly Phe MET Arg Leu Ser Gln Asp Asp
     (G)
```

TABLE 3-continued

```
{gtgag...v..cctag}
1172 CAG ATA TTA CTG CTG AAG ACG GGC TCC TTT GAG CTG GCG ATT GTT CGC ATG TCC AGA CTG CTT GAT CTC TCA CAG AAC GCG GTT CTC TAC GGC    346
     Gln Ile Leu Leu Leu Lys Thr Gly Ser Phe Glu Leu Ala Ile Val Arg MET Ser Arg Leu Leu Asp Leu Ser Gln Asn Ala Val Leu Tyr Gly
                                                           (G)
1265 GAC GTG ATG CTG CCC CAG GAG GCG TTC TAC ACA TCC GAC TCG GAA GAG ATG CGT CTG GTG TCG CGC ATC TTC CAA ACG GCC AAG TCG ATA GCC    377
     Asp Val MET Leu Pro Gln Glu Ala Phe Tyr Thr Ser Asp Ser Glu Glu MET Arg Leu Val Ser Arg Ile Phe Gln Thr Ala Lys Ser Ile Ala 1358 GAA CTC AAA CTG ACT GAA ACC GAA CTG CGC CTG TAT CAG AGC TTA GTG CTG CTC TGG CCA GAA CGC AAT GGA GTG CGT GGT AAT ACG GAA ATA    408
     Glu Leu Lys Leu Thr Glu Thr Glu Leu Arg Leu Tyr Gln Ser Leu Val Leu Leu Trp Pro Glu Arg Asp Gly Val Arg Gly Asn Thr Glu Ile
                                                {gtgcg...v..cctag}
1451 CAG AGG CTT TTC AAT CTG AGC ATG GCG ATC CGG CAG GAG CTG GAA ACG AAT CAT GCG CCG CTC AAG GGC GAT GTC ACC GTG CTG GAC ACA        439
     Gln Arg Leu Phe Asn Leu Ser MET Asn Ala Ile Arg Gln Glu Leu Glu Thr Asn His Ala Pro Leu Lys Gly Asp Val Thr Val Leu Asp Thr
                        {gtacgt..v..ttccag}
1544 CTG CTG AAC AAT ATA CCC AAT TTC CGC GAT ATT TCC ATC TTG CAC ATG GAA TCG CTG AGC AAG TTC AAG CTG CAG CAC CCG AAT GTC GTT TTT    470
     Leu Leu Asn Asn Ile Pro Asn Phe Arg Asp Ile Ser Ile Leu His MET Glu Ser Leu Ser Lys Phe Lys Leu Gln His Pro Asn Val Val Phe 1637 CCG GCG CTG TAC AAG GAG CTG TTC TCG ATA GAT TCG CAG CAG GAC CTG ACA TAA CAAGAGCAGCAGCCGTTCCTGAGACGAGCCGCGGACGATGTTGCCGAGGAT    487
     Pro Ala Leu Tyr Lys Glu Leu Phe Ser Ile Asp Ser Gln Gln Asp Leu Thr —

1742 GCGGCTGCCGCCGGATGTGTCCTGCCGCCGGTGCCGCCCCTGCCGGGCAGCAGCCAGCCGCTGCTCGAGGACTGAGGGCCGCAGGATGTGGCAACAATAATTATTGAGTAAACACTGCACTGC

1866 GCATGCAGCAGATACAAGAACTTTATCATGATTTAAGCTAGCATACAACCAAGGATGTGATCCTCGCCAAGGACTCACTTAAAAAGAACTCTATCTATATATACATATATAAATTATATGACAG

1990 AGCGGATGACGCAAAGGAAGGGAAAATATTTCAAAATATTGTTAACTCAGTTAAGACTTTTGCTTCGTAGAGAACCGAAACCGATTGCATTTCGAGCAGGGCATCAAACTGATT

2114 TTCGAGGTTATACTATACATATATATACACACAAACACACACACATATTAACTTCCAAACTTTCATATCCTGGCCCGAGCAGATCAGATCGTCTAAGTACTTAAA

2238 ACCAAGCGAAATTCTCTACACCGCACAACCCAGGACCCGTAGACCCCCAATAATTCAGTTCGGTTAGTGTTAACCCCAGAAAGCCCAGATCCGATTCCGATCCCGCCT...
```

The genomic structure of the EcR and DHR3 genes was investigated by isolating additional genomic DNA clones that form overlapping sets that contain all of the sequences found in the respective cDNA clones. The exons contained in these cDNAs were mapped within the genomic DNA by comparison of cDNA and genomic clones via Southern blot analysis, mapping of restriction cleavage sites, and finally, by determination of the nucleotide sequence of the genomic DNA in regions that contain the exon/intron boundaries. Table 2 and 3 show these boundaries and the sequence of the splice junctions for the EcR and DHR3 genes, respectively. All of these splice junctions conform to the splice donor and acceptor consensus sequences.

For EcR, the cDNA sequence shown in Table 2 is split into six exons spread over 36 kb of genomic DNA, with the ORF beginning in the second exon and ending in the sixth. For DHR3, the cDNA sequence derives from nine exons spread over 18 kb, with the ORF beginning in the first exon and ending in the ninth. Because the 5' and 3' ends of the respective mRNAs were not mapped, it should be emphasized that these genes may have additional noncoding exons at their 5' or 3' ends.

The EcR and DHR3 gene structures differ significantly from those of all previously examined steroid receptor superfamily genes. Comparison with the genes for 11 other receptor homologues for which at least partial structural information is available reveals that the positions of certain exon boundaries have been conserved in evolution. This conservation is most striking in the portion of the genes encoding DNA-binding domains. In the nine other cases where the structure of this region has been examined, the two halves of the DNA-binding domain are always encoded by separate exons. If we exclude the Drosophila genes knirps, knirps-related, and egon (which are not bona fide receptor homologues since they lack the hormone-binding domain sequence similarity), these are always small exons, the second one invariably ending in the fourth codon past the conserved Met codon at the end of the C region. Thus, these exons each encode one of the two predicted Zn fingers of the DNA-binding domain. In contrast, both Zn fingers of the putative DNA-binding domain of the EcR and DHR3 receptors are encoded by a single exon. It is possible that our screen specifically selected for genes lacking the above intron. The screen selected genomic clones that hybridize to an E75A cDNA probe that, of course, lacks this intron. Genomic sequences containing a contiguous sequence encoding the DNA-binding domain would be expected to hybridize to this probe better than clones from genes containing the intron. This would explain the successful isolation of the EcR and DHR3 genes, and the failure to isolate the genes of other Drosophila members of the steroid receptor superfamily.

Methods

Isolation of cDNA and additional genomic clones

Subclones of the originally isolated DHR3 and EcR genomic clones were used to screen a cDNA library prepared from third instar tissues treated with ecdysone and cycloheximide. This library was chosen because both genes are relatively highly expressed at the end of third instar, and because of the high quality of the library. Of the 270,000 primary plaques screened, 20 positives for DHR3 and 220 for EcR were detected. Twenty cDNAs for each gene were purified, of which the ten largest for each were restriction mapped and found to be colinear. cDNA DHR3-9, which extends farther both 5' and 3' than our other DHR3 cDNAs, was chosen for sequencing. For EcR, the longest cDNA, EcR-17, extended the farthest 5' and was sequenced in its entirety. An additional cDNA clone, EcR-9, was found to extend 300 bp farther 3' than EcR-17, and this 3' extension was also sequenced. Additional genomic DNA clones covering the EcR and DHR3 genes were obtained by screening the Drosophila Canton S genomic library referred to in part A above either with probes from the respective cDNA clones, or for overlapping clones by the chromosomal walk method described in Experimental Example I.

DNA sequence analysis cDNAs were subcloned into BlueScript vectors (Stratagene), and clones for sequencing were generated by exonuclease III digestion (Henikoff, S., 1984. Unidirectional digestion with exonuclease III creates targeted breakpoints for DNA sequencing. *Gene* 28:351–359).

Double-stranded plasmids were denatured (Gatermann, K. B., G. H. Rosenberg, and N. F. Kaufer, 1988. Double-stranded sequencing, using mini-prep plasmids, in 11 hours. *BioTechniques* 6:951–952) and sequenced by the dideoxy chain terminating method (Sanger, F., S. Nicklen, and A. R. Coulson, 1977. DNA sequencing with chain-terminating inhibitors. *Proc. Natl. Acad. Sci. USA* 74:5463–5467), using the enzyme Sequenase (U.S. Biochemical). cDNA EcR-17 was completely sequenced on both strands, as was the EcR-9 3' extension. cDNA DHR3-9 was sequenced on both strands for the 5' most 2338 bp, which contains the entire ORF, and the remainder of the long 3' untranslated region was sequenced on one strand.

The exon/intron boundaries in genomic DNA clones were first mapped at low resolution by Southern blot analysis of their restriction fragments probed with labeled cDNAs. Genomic DNA surrounding each exon/intron boundary was subcloned and the nucleotide sequence of these subclones determined as above.

Genomic exons were either sequenced entirely, or for the longer exons, were digested and electrophoresed in parallel with cDNA clones to confirm the colinearity of the genomic and cDNA clones. Shorter exons were completely sequenced from genomic clones. Longer exons had their boundaries sequenced from genomic clones, and were confirmed to be colinear with the cDNA clones by parallel digestion and electrophoresis of the cDNA and genomic clones.

C. The Predicted Amino Acid Sequence of the EcR and DHR3 Proteins and their Implications Comparison of the predicted EcR and DHR3 protein sequences to the sequence database and to individual members of the steroid receptor superfamily shows that these proteins share the two conserved domains characteristic of this superfamily (Evans, R. M., 1988. The steroid and thyroid hormone receptor superfamily. *Science* 240:889–895; Green, S., and P. Chambon, 1988. Nuclear receptors enhance our understanding of transcription regulation. *Trends in Genetics* 4:309–314). We refer to the domains as the C and E regions, for the more amino-terminal and more carboxy-terminal homologies, respectively, according to the nomenclature of Krust et al. (Krust, A., S. Green, P. Argos, V. Kumar, P. Walter, J. M. Bornert, and P. Chambon, 1986. The chicken oestrogen receptor sequence; homology with v-erbA and the human oestrogen and glucocorticoid receptors. *EMBO J.* 5:891–897). These domains are underlined in Tables 2 and 3, and Table 4A–C presents a comparison of these domains from EcR and DHR3 with those from representative members of the superfamily.

TABLE 4

Sequence comparison of the conserved C and E regions in DHR3, EcR, and some representative nuclear receptor homologues. (A) C-region alignment. Numbers at the left indicate the amino acid positions within the individual receptors; dashes indicate gaps introduced to obtain maximal alignment. Dots indicate three positions important in determining the DNA binding specificity of this domain. (B) E-region alignment. Bars indicate the three most highly conserved stretches within this domain. (C) Computed percent identifies among the C-region sequences (lower left) and among the E-region sequences (upper right). The kni sequence shows no significant E-region homology and is, therefore, not included in this comparison. Sequences shown are from: E75A, Drosophila ecdysone-inducible gene at 75B; kni, Drosophila segmentation gene knirps; hRARα, human retinoic acid receptor alpha; hRβ, human thyroid receptor beta; hVDR, human vitamin D receptor; cOUP-TF, chicken ovalbumin upstream promoter transcription factor; hERR1 and hERR2, human estrogen-related receptors 1 and 2; hER, human estrogen receptor; hGR, human glucocorticoid receptor; hMR, human mineralocorticoid receptor; hPR, human progesterone receptor.

Panel 1

A

| | | |
|---|---|---|
| DHR3 | 51 | CKVCGDKSS GVHYGVI TCEGCKGFFRRSQSS VV---NYQCPRNKQCVV DR VN RNRCQYCRLQ KCL KLGM |
| EcR | 264 | CLVCGDRAS GYHYNAL TCEGCKGFFRRS VTKS A---VYC CKFGRACEMDMYMRRKCQECRLK KCLAVGM |
| E75A | 245 | CRVCGDKAS GFHYGVHS CEGCKGFFRRSI QQKI -QYRP CTKNQQCSI LR I NRNRCQYCRLK KCI AVGM |
| kni | 5 | CKVCGEP AAGF HFGAFTCEGCKSFFGRSYNNI S –TI SE CKNEGKCI I DK KN RTTCKACRLR KCYNVGM |
| hRARα | 58 | CFVCQDKSS GYHYGVS ACEGCKGFFRRSI QKNM--VYT CHRDKNCI I NK VT RNRCQYCRLQ KCF EVGM |
| hTRβ | 102 | CVVCGDKATGYHYRCI TCEGCKGFFRRTI QKNL HPS YSCKYEGKCVI DK VT RNQCQECRFK KCI YVGM |
| hVDR | 24 | CGVCGDRATGFHFNAMTCEGCKGFFRRSMKRKA--LFT CPFNGDCRI TK DN RRHCQACRLK RCVDI GM |
| cOUP-TF | | CVVCGDKSS GKHYGQF TCEGCKSFFKRS VRRNL --T YTCRANRNCPI DQ HH RNQCQYCRLK KCL KVGM |
| hERR1 | 175 | CLVCGDVAS GYHYGV ASCEACKAFFKRTI QGSI --EYS CPASNECEI TKRR RKACQACRFTK CLRVGM |
| hERR2 | 103 | CLVCGDI ASGYHYGVASCEACKAFFKRTI QGNI --EYS CPATNECEI TKRR RKSCQACRFMKCLKVGM |
| hER | 185 | CAVCNDYASGYHYGVWSCEGCKAFFKRSI QGHN--DYMCPATNQCTI DKNR RKSCQACRLRKCYEVGM |
| hGR | 421 | CLVCSDEAS GCHYGVLTCGSCKVFFKRAVEGQH---NYL CAGRNDCI I DKI R RKNCPACRYRKCLQAGM |
| hMR | 603 | CLVCGDEAS GCHYGVVTCGSCKVFFKRAVEGQH---NYL CAGRNDCI I DKI R RKNCPACRLQKCLQAGM |
| hPR | 567 | CLI CGDEAS GCHYGVLTCGSCKVFFKRAMEGQH---NYL CAGRNDCI VDKI R RKNCPACRLR KCCQAGM |

TABLE 4-continued

C

|  | DHR3 | EcR | E75A | kni | hRARα | hTRβ | hVDR | cOUP | hERR1 | hERR2 | hER | hGR | hMR | hPR |
|---|---|---|---|---|---|---|---|---|---|---|---|---|---|
| DHR3 |  | 55 | 64 | 47 | 18 | 18 | 17 | 14 | 13 | 14 | 15 | 13 | 16 | 15 |
| EcR | 55 |  | 55 |  | 24 | 29 | 25 | 20 | 16 | 15 | 17 | 14 | 14 | 13 |
| E75A | 64 | 55 |  |  | 23 | 20 | 22 | 16 | 15 | 15 | 13 | 14 | 12 | 15 |
| kni | 47 | 48 | 48 |  |  |  |  |  |  |  |  |  |  |  |
| hRARα | 65 | 55 | 62 | 45 |  | 33 | 22 | 18 | 18 | 18 | 17 | 14 | 15 | 16 |
| hTRβ | 56 | 59 | 58 | 52 | 62 |  | 22 | 16 | 18 | 17 | 19 | 14 | 18 | 15 |
| hVDR | 50 | 58 | 55 | 53 | 47 | 52 |  | 17 | 20 | 19 | 15 | 13 | 15 | 13 |
| cOUP | 62 | 58 | 58 | 50 | 61 | 59 | 50 |  | 29 | 30 | 24 | 21 | 19 | 20 |
| hERR1 | 48 | 53 | 54 | 43 | 53 | 56 | 45 | 51 |  | 63 | 32 | 25 | 23 | 25 |
| hERR2 | 49 | 51 | 54 | 43 | 54 | 57 | 45 | 54 | 91 |  | 33 | 25 | 21 | 25 |
| hER | 53 | 52 | 58 | 52 | 59 | 53 | 47 | 55 | 69 | 72 |  | 27 | 25 | 27 |
| hGR | 47 | 48 | 44 | 45 | 45 | 44 | 41 | 48 | 57 | 57 | 58 |  | 91 | 54 |
| hMR | 52 | 50 | 47 | 47 | 48 | 45 | 44 | 52 | 59 | 59 | 58 | 94 |  | 56 |
| hPR | 48 | 47 | 44 | 45 | 44 | 42 | 42 | 45 | 54 | 54 | 56 | 91 | 91 |  |

B

```
DHR3    255  KLEAVHDMFRKQPDVS RI LYYKNLGQEEL WLDCAEKLTQMI QNI I EF AKLLPGFMRLSQDDQI LLLKTGS F ELAI VRMSRL--LDL S
EcR     431  QDGYEQP S EEDLRRI MS QPDENESQTDVS F RHI TEI TI LT VQLI VEF AKGLPAFTI KI PQEDQI TLLKACS S EVMMLRMAR R---YDHS
E75A    380  QRARDCP S YSMPTLLACPLNPA PELQSE QEF--SQRFAHVI RGVI DF AGMI PGFQLLTQDDKF TLLKAGLF DAL F VRLI CM--FDS S
hRARα   170  P ALCQLGKYTT NNSSE QRVSLDI DL--WDKF--SELSTKCI I KT VEF AKQLPGFT TLTI ADQI TLLKAACLDI LI LRI CTR--YTP E
hTRβ    238  P KFL PEDI GQAPI VNAP EGG-KVDLEAF S HF--TKI I TPAI TRVVDF AKKLPMFCELPCEDQI I LLKGCCMEI MS LRAAVR--YDP E
hVDR    198  DSSS FSNL DLS EEDSDDPSVTL ELSQLS ML PHLADLVSYS I QKVI GF AKMI PGFRDLTS EDQI VLLKSSAI EVI MLRS NE S---FTMD
cOUP-TF      GYI S LLL RAEP YPTSR Y GSQCMQPNNI MGI ENI CELAARLL FSA VEWARNI PF F P DLQI TDQVSLLRLT WS ELF VLNA AQCSMPLH V
hERR1   294  L VSHLLV- VEP EKLYAMP DPAGPDGHL PA VATLCDLF DREI VVTI SWAKS I PGF S SLSLSDQMS VLQSVWMEVL VLGV AQRSLPLQD
hERR2   211  I VSYLLV- AEP DKLYAMPPDDV PEGDI KAL TTLCDLADRE L VFLI SWAKHI PGFS NLTLGDQMSLLQS AWMEI L I LGI VYRSLPYDD
hER     315  MVS ALLD- AEP PI LYS E YDPTR PFSEAS MMGLLTN LADRE L VHMI NWAKR VPGFVDLTLHDQVHLLECAWL EI L MI G L VWRSMEHP--
hGR     531  TLVS LLEVI EP EVLYAGYDS S VPDSTWR I MTTLNMLGGRQVI AA VKWAKAI PGF RNLHL DDQMTLLQYSWMFLMAFAL GWRSYRQS S
hMR     737  S PVMVLENI EPEI VYAGYDSS KPDTAENL L STLNR LAGKQMI QVVKWAKVLPGFKNLPLEDQI TLI QYSWMCLS S FAL SWRSYKHT N
hPR     686  P LI NLLMS I EP DVI YAGHDNTKPDTSSS LL TSLNQLGERQLL SVVKWSKS LPGFRNLHI DDQI TLI QYSWMSLMVFGL GWRSYKHVS
```

E1

```
DHR3    255  - LDL SQNAVLYGDVMLP QE AFYT S ---DS E EMRLVSRI F QT AKS I AEL
EcR     431  - YDHS SDS I FFANNRSYT RDS YKM--AGMADNI EDLLHF CR QMFS MKV
```

TABLE 4-continued

```
DHR3    380  KL------------TETELALYQSLVLLWPE-RNGVRGNTEI QRL FNLSMNAI RQ------------
EcR     557  ------------DNVEYALL T AI V--I FSD--RPGLEKAQLVEAI QSYYI DTLRI------------
E75A    503  NL------------TDAEI GLF CAI VLI T PD--RPGLRNLELI EKMYSRLKGCLQ------------
hRAR    292  ------------DD AETGLL S AI CLI C GD--RQDLEQPDRVDML QEALKV------------
hTRβ    361  ------------DDTEVALL QAVLLMS SD--RPGLACVERI EKY QDSFL LAFEH------------
hVDR    325  L H------------EEEHVLL MAI CI VS PD--RPGVQDAALI EAI QDRLS NTLQT------------
cOUP-TF      VE KLKALHVDS AEYSCL K AI VLFT SD--ACGLSDAAHI ESL QEKSQCALEE------------
hERR1   410  VR RLQALRLEREEYVLL KALALANSD------------SVHI E-DEPRLWSSCE--KLL HEALLEYE---
hERR2   328  VR RYKKLKVEKEEFVML KALALANSD------------SMYI ENLEAVQKLQ---DLLHEALQDYE---
hER     437  MMNLQ---GEEFVCL KSI I LLNSG------------VYTFLSS TLKSL E------EKDHI HRVLDKI TD
hGR     653  L HRLQ---VS YEEYLCMKTLLLLS SVPKDGL------------KSQELFDEI RMTYI KELGK---
hMR     859  F VRLQ------TFEEYTI MK VLLLLS TI PKDGL------------KSQAAFEEMRT NYI KELRK---
hPR     808  F VKLQ-----VSQEEFLCMK VLLLLNTI PLEGL------------RSQTQTFEEMRS SYI RELI K---
```

```
E75A    380  -FDS SI NSI I CLN-GQVMR RDAI Q-NGANARFLVDSTF NF AE RMNSM
hRARα   170  -YTP EQDT MTFSDGL TLNRTQMHN-AGF GPL TDLVFAF ANQLLP LEM
hTRβ    238  -YDP ESE TL TLNGEMAVI RGQLKN-GGL GVVSDAI FDL GMS LSS FNL
hVDR    198  -FTMDDMS WTCGNQDYKYR VSDVT KAGHS LELI EPLI KFQVGLKKLN
cOUP-TF      MPLHVAP L L AAAGLHAS P MS ADR V -VAF MDH------------I RI F QEN
hERR1   294  L PLQDE--LAFAEDL VL DE EGARA-AGL GEL------------GAALLQL
hERR2   211  L PYDDK--LAYAEDY I MDE EHSRL-VGL LEL------------YRAI LQL
hER     315  MEHP--VKLL-FAPNL LL DRNQGKC-VEGMVE----I FDMLLATSS RFR
hGR     531  YRQS SANLL CFAPDLI I NE-QRNT-LPCNYDQCKH------ML YVSSE
hMR     737  YKHT NSQFL YFAPDL VF NE-EKMH-QS AMYELCQG------MHQI SLQ
hPR     686  YKHVSGQML YFAPDL I L NE-QRMK-ESS F YS LCLT------MWQI PQE
```

```
                                     E3
DHR3    380  ------EL ETNHAPL KGDVTVLDTL LNNI PNFRDI SI LHMES LSKF KL QHPN----VVFPALYKELFS
EcR     557  -YI LNR----HCGDSMSLVF YAKL LS I L TELRTL GNQNAEMCFSL KL KNRK-----LPKF LEEI WD
```

TABLE 4-continued

| | | |
|---|---|---|
| E75A | 503 | -YI VAQ------NR P DQP EF LAKL LE TMPD LRTL STLHT EKL-----------VVFRTE HKEL L R |
| hRAR | 292 | -Y--VRK------RR P S RPHMF P KMLMKI TDLRSI S AKGAE R VI TL KMEI PGSM-----PPLI QEMLEN |
| hTRβ | 361 | -YI NYR------KHH VTHF WPKL LMKV TDLRMI GACHA S R FLHMKV ECP TELL----PPLF LEVF ED |
| hVDR | 325 | -YI RCR HPPP GSHLL YAKMI QKL A----DLRSL NDDHS KQ YRCL SF Q-PEC- S MKLTPLVL EVF GN |
| cOUP-TF | | ------YVRSQ--YP NQPSR FGKL LL RL PSLRTVSSSVI EQLFF VRL VGKTPI E-TLI RDMLL S GS S |
| hERR1 | 410 | ------AGRAGP GG GA ERRR AGRL LL TL PLLRQT AGKVL AHFYGV KL EGKVP MH - KLFLEML EAMMD |
| hERR2 | 328 | ------LSQRHE E EP RR AGKL LL TL PLLRQT AAKAV QHFYS VKL QGKVPMH - KLFLEML EAKV |
| hER | 437 | TLI HL MAKAGLTL QQ QHQR LAQL LL I L SHI RHMSNKGMEH LYSMKC KNVVPL Y - DLLLEML DAHR L |
| hGR | 653 | AI VKRE GNSS QNWQR FYQ--LTKL LDSMHEVENLLN-----YCF QT FLD-KTMS I EFPEML AEI I T |
| hMR | 859 | MVTKCP NNS GQS WQR FYQ--LTKL LDSMHDL VSDLLE------FCF YT FRESHAL K VEFPAML VEI I S |
| hPR | 808 | AI GLRQ KGVVSS S QR FYQ--LTKL LDNL HDL VKQ------LHLYCL NT FI QSRAL S VEF PEMMSEVI A |

Panel 2

A

| | | |
|---|---|---|
| DHR3 | 51 | CKVCGDKS S GVHYGVI TCEGCKGFFRRSQS S VV--NYQCPRNKQCVV DR VN RNRCQYCRLQ KCL KLGM |
| EcR | 264 | CL VCGDRAS GYHYNAL TCEGCKGFFRRS VTKS A--VYC CKF GRACEMDYMYRRKCQECRL K KCLAVGM |
| E75A | 245 | CRVCGDKAS GFHYGVHS CEGCKGFFRRSI QQKI -QYRP CTKNQQCSI LRI NRNRCQYCRLK KCI AVGM |
| kni | 5 | CKVCGEP AAGF HFGAFTCEGCKS FFGRS YNNI S -TI SECKNEGKCI I DKKNRTTCKACRLR KCYNVGM |
| hRARα | 58 | CFVCQDKS S GYHYGVS ACEGCKGFFRRSI QKNM--VYT CHRDKNCI I NKVT RNRCQYCRLQ KCF EVGM |
| hTRβ | 102 | CVVCGDKATGYHYRCI TCEGCKGFFRRTI QKNL HPS YSCKYEGKCVI DKVT RNQCQECRFKKCI YVGM |
| hVDR | 24 | CGVCGDRATGFHFNAMTCEGCKGFFRRS MKRKA--LFT CPFNGDCRI TKDN RRHCQACRLR RCVDI GM |
| cOUP-TF | | CVVCGDKS S GKHYGQF TCEGCKS F F KRS V RRNL--T YTCRANRNCPI DQ HH RNQCQYCRLK KCL KVGM |
| hERR1 | 175 | CL VCGDVAS GYHYGV AS CEACKAFFKRTI QGSI --EYS CP AS NECEI TKRR RKACQACRFTKCLRVGM |
| hERR2 | 103 | CL VCGDI AS GYHYGVAS CEACKAFFKRTI QGNI --EYS CP ATNECEI TKRR RKS CQACRFMKCLKVGM |
| hER | 185 | CAVCNDYAS GYHYGVWS CEGCKAFF KRSI QGHN--DYMCP ATNQCTI DKNR RKS CQACRLRKCYEVGM |
| hGR | 421 | CLVCS DEAS GCHYGVL TCGS CKVFF KRAV EGQH--NYL CAGRNDCI I DKI R RKNCP ACRYRKCL QAGM |
| hMR | 603 | CL VCGDEAS GCHYGVV TCGS CKVFF KRAV EGQH--NYL CAGRNDCI I DKI R RKNCP ACRL QKCL QAGM |
| hPR | 567 | CLI CGDEAS GCHYGVL TCGS CKVFF KRAMEGQH--NYL CAGRNDCI VDKI R RKNCP ACRLR KCCQAGM |

Panel 3

TABLE 4-continued

B

| | | |
|---|---|---|
| DHR3 | 255 | KLEAVHDMFRKQPDVSRILYYKNLGQEELWLDCAEKLTQMIQNIEFAKLLPGFMRLSQDDQILLLKTGSFELAIVRMSRL--LDLS |
| EcR | 431 | QDGYEQPSEEDLRRIMSQPDENESQTDVSFRHITEITILTVQLIVEFAKGLPAFTKIPQEDQITLLKACSSEVMMLRMARR---YDHS |
| E75A | 380 | QRARDCPSYSMPTLLACPLNPAPELQSEQEF--SQRFAHVIRGVIDFAGMIPGFQLLTQDDKFTLLKAGLFDALFVRLICM--FDSS |
| hRARα | 170 | PALCQLGKYTTNNSSEQRVSLDIDL--WDKF--SELSTKCIIKTVEFAKQLPGFTTLTIADQITLLKAACLDILLRICTR--YTPE |
| hTRβ | 238 | PKFLPEDIGQAPIVNAPEGG--KVDLEAFSHF--TKIITPAITRVVDFAKKLPMFCELPCEDQILLKGCCMEIMSLRAAVR---YDPE |
| hVDR | 198 | DSSSFSNLDLSEEDSDDPSVTLELSQLSMLPHLADLVSYSIQKVIGFAKMIPGFRDLTSEDQIVLLKSSAIEVIMLRSNES---FTMD |
| cOUP-TF | | GYISLLLRAEPYPTSRYGSQCMQPNNIMGIENICELAARLLFSAVEWARNIPFFPDLQITDQVSLLRLTWSELFVLNAAQCSMPLHV |
| hERR1 | 294 | LVSHLLV-VEPEKLYAMPDPAGPDGHLPAVATLCDLFDREIVVTISWAKSIPGFSSLSLSDQMSVLQSVWMEVLVLGVAQRSLPLQD |
| hERR2 | 211 | IVSYLLV-AEPDKLYAMPPDDVPEGDIKALTTLCDLADRELVFLISWAKHIPGFSNLTLGDQMSLLQSAWMEILILGIVYRSLPYDD |
| hER | 315 | MVSALLD-AEPPILYSEYDPTRPFSEASMMGLLTNLADRELVHMINWAKRVPGFVDLTLHDQVHLLECAWLEILMIGLVWRSMEHP- |
| hGR | 531 | TLVSLLEVIEPEVLYAGYDSSVPDSTWRIMTTLNMLGGTQVIAAVKWAKAIPGFRNLHLDDQMTLLQYSWMFLMAFALGWRSYRQSS |
| hMR | 737 | SPVMVLENIEPEIVYAGYDSSKPDTAENLLSTLNRLAGKQMIQVVKWAKVLPGFKNLPLEDQITLIQYSWMCLSSFALSWRSYKHTN |
| hPR | 686 | PLINLLMSIEPDVIYAGHDNTKPDTSSSLLTSLNQLGERQLLSVVKWSKSLPGFRNLHIDDQITLIQYSWMSLMVFGLGWRSYKHVS |

E1

| | | |
|---|---|---|
| DHR3 | 255 | -LDLSQNAVLYGDVMLPQEAFYTS---DSEEMRLVSRIFQTAKSIAEL |
| EcR | 431 | -YDHSSDSIFFANNRSYTRDSYKM--AGMADNIEDLLHFCRQMFSMKV |
| E75A | 380 | -FDSSINSIICLN-GQVMRRDAIQ--NGANARFLVDSTFNFAERMNSM |
| hRARα | 170 | -YTPEQDTMTFSDGLTLNRTQMHN--AGFGPLTDLVFAFANQLLPLEM |
| hTRβ | 238 | -YDP-ESETLTLNGEMAVIRGQLKN--GGLGVVSDAIFDLGMSLSSFNL |
| hVDR | 198 | -FTMDDMSWTCGNQDYKYRVSDVTKAGHSLELIEPLIKFQVGLKKLN |
| cOUP-TF | | MPLHVAPLLAAAGLHASPMSADRV-VAFMDH-------IRIFQEN |
| hERR1 | 294 | LPLQDE--LAFAEDLVLDEEGARA-AGLGEL---------GAALLQL |

Panel 4

| | | |
|---|---|---|
| DHR3 | 380 | KL------TETELALYQSLVLLWPE-RNGVRGNTEIQRLFEIQRLFNLSMNAIRQ---- |
| EcR | 557 | -------DNVEYALLTAIV-IFSD-RPGLEKAQLVEAIQLVEAIQSYYIDTLRI---- |
| E75A | 503 | NL------TDAEIGLFCAIVLITPD-RPGLRNLELIEKMYLIEKMYSRLKGCLQ---- |

E2

TABLE 4-continued

Panel 5

| | | |
|---|---|---|
| hRAR | 292 | ---------------DD AETGLL S AI CLI CGD-RQDLEQP D RVDML QRVDMLQEPLL EALKV------------ |
| hTRβ | 361 | ---------------DDTEVALL QAVLLMS SD-RPGLACVE RI EKYQRI EKYQDSFL LAFEH------------- |
| hVDR | 325 | L H--------EEEHVLL MAI CI VS PD-RPGVQDAALI EAI QLI EAI QDRLS NTLQT-------------- |
| cOUP-TF | | VE KL KALHVDS AEYS CL KAI VLFT S D-ACGLS DAAHI ESL QHI ES LQEKS Q CALEE--------- |
| hERR1 | 410 | VR RLQALRLEREEYVLL KALALANS D---------SVHI E-DEHI E- DEPRLWS SCE- KLL HE ALLEYE--- |
| hERR2 | 328 | VR RYKKL KVEKEEF VML KALALANS D----------SMYI ENL EYI ENLEAVQKLQ---DLL HE ALQDYE--- |
| hER | 437 | MMNL Q-----GEEF VCL KS I I LLNS G---------VY TFLS S TTFLS STLKSL E-----E KDHI HRVLDKI TD |
| hGR | 653 | L HRLQ---VS YEEYLCMKTLLLLS SVPKDGL---------------KS QELFDEI RMTYI KELGK--- |
| hMR | 859 | F VRLQ----TFEEYTI MK VLLLS TI PKDGL---------------KS QAAFEEMRT NYI KELRK--- |
| hPR | 808 | F VKLQ----VS QEEFLCMK VLLLNTI PLEGL---------------RS QTQTFEEMRS SYI RELI K---- |

Panel 6

| | | E3 |
|---|---|---|
| DHR3 | 380 | ----EL ETNHAPL KG DVTVLDTL LNNI PNFRDI SI LHMES LSKF KL QHPN------ VVFPAL Y KEL F S |
| EcR | 557 | - YI LNR----HCGDS MSLVF YAKL LS I L TELRTL GNQNAEMCFSL KL KNRK------LPKF LEEI WD |
| E75A | 503 | - YI VAQ--------NR PDQPEF LAKL LE TMPDLRTL STLHT EKL---------- VVFRTE HKELL R |
| hRAR | 292 | - Y--VRK-------RR PS RPHMFP KMLMKI TDLRSI SAKGAER VI TL KMEI PGSM------PPLI QEMLEN |
| hTRβ | 361 | - YI NYR---------KHH VTHFWP KL LMKV TDLRMI GACHAS R FLHMKV ECPTELL----PPLF LEVF ED |
| hVDR | 325 | - YI RCR HPPPGSH LL YAKMI QKL A------DLRSL NDDHS KQYRCL SF Q-PEC- S MKLTPL V LEVF GN |
| cOUP-TF | | ---------YVRS Q- YPN QPSR FGKL LL RL PSLRTVSSS VI EQLFFVRL VGKTPI E- TLI RDML LS GS S |
| hERR1 | 410 | ---------A GRAGP GG GA ERRR AGRL LL TL PLLRQT AGKVL AHFYGV KL EGKVPMH- KLFLEML EAMMD |
| hERR2 | 328 | -----------LS QRHEE EPRR AGKL LL TL PLLRQT AAKAV QHFYS V KL QGKVPMH- KLFLEML EAK V |
| hER | 437 | TLI HLMAKAGLTL QQ QHQR LAQL LL I L SHI RHMSNKGMEHL YS MKC KNVVPL Y- DLLLEML DAHRL |
| hGR | 653 | AI VKRE GNS S QNWQR FYQ- LTKL LDS MHEVVENLLN------ YCF QT FLD- KT MS I EFPEML AEI I T |
| hMR | 859 | MVTKCP NNS GQS WQR FYQ- LTKL LDS MHDL VS DLLE-------FCF YT FRES HAL KVEFPAML VEI I S |
| hPR | 808 | AI GLRQ KGVVS SS QR FYQ- LTKL LDNL HDLVKQ------ LHLYCL NTI FI QSRAL S VEFPEMMS EVI A |

C

TABLE 4-continued

| | DHR3 | EcR | E75A | kni | hRARα | hTRβ | hVDR | cOUP | hERR1 | hERR2 | hER | hGR | hMR | hPR |
|---|---|---|---|---|---|---|---|---|---|---|---|---|---|---|
| DHR3 | | 19 | 24 | | 18 | 18 | 17 | 14 | 13 | 14 | 15 | 13 | 16 | 15 |
| EcR | 55 | | 23 | | 24 | 29 | 25 | 20 | 16 | 15 | 17 | 14 | 14 | 13 |
| E75A | 64 | 55 | | | 23 | 20 | 22 | 16 | 15 | 15 | 13 | 14 | 12 | 15 |
| kni | 47 | 48 | 48 | | | | | | | | | | | |
| hRARα | 65 | 55 | 62 | 45 | | 33 | 22 | 18 | 18 | 18 | 17 | 14 | 15 | 16 |
| hTRβ | 56 | 59 | 58 | 52 | 62 | | 22 | 16 | 18 | 17 | 19 | 14 | 18 | 15 |
| hVDR | 50 | 58 | 55 | 53 | 47 | 52 | | 17 | 20 | 19 | 15 | 13 | 15 | 13 |
| cOUP | 62 | 58 | 58 | 50 | 61 | 59 | 50 | | 29 | 30 | 24 | 21 | 19 | 20 |
| hERR1 | 48 | 53 | 54 | 43 | 53 | 56 | 45 | 51 | | 63 | 32 | 25 | 23 | 25 |
| hERR2 | 49 | 51 | 54 | 43 | 54 | 57 | 45 | 54 | 91 | | 33 | 25 | 21 | 25 |
| hER | 53 | 52 | 58 | 52 | 59 | 53 | 47 | 55 | 69 | 72 | | 27 | 25 | 27 |
| hGR | 47 | 48 | 44 | 45 | 45 | 44 | 41 | 48 | 57 | 57 | 58 | | 57 | 54 |
| hMR | 52 | 50 | 47 | 47 | 48 | 45 | 44 | 52 | 59 | 59 | 58 | 94 | | 56 |
| hPR | 48 | 47 | 44 | 45 | 44 | 42 | 42 | 45 | 54 | 54 | 56 | 91 | 91 | |

The C region is a 66–68 amino acid domain that has been shown to function as a Zn finger DNA binding domain in vertebrate receptors. This domain has also been implicated in receptor dimerization (Kumar, V., and P. Chambon, 1988. The estrogen receptor binds tightly to its responsive element as a ligand-induced homodimer. *Cell* 55:145–156). As shown in Table 4A, all 19 C-region residues that are absolutely conserved in the other receptor homologues are also conserved in DHR3 and EcR, including the nine invariant Cys residues, eight of which coordinate two zinc ions (Freedman, L. P., B. F. Luisi, Z. R. Korszun, R. Basavappa, P. B. Sigler, and K. R. Yamamoto, 1988. The function and structure of the metal coordination sites within the glucocorticoid receptor DNA binding domain. *Nature* 334:543–546). As seen in Table 4C, the Drosophila C-region sequences (including those of E75A) are not more closely related to each other than they are to those from the vertebrate receptor homologues. The C region of DHR3 is most similar to that of the human retinoic acid receptor α (hRARα), and the C region of EcR is most similar to that of the human thyroid receptor β (hTRβ). Studies on the human glucocorticoid receptor (hGR) and human estrogen receptor (hER) have identified three C-region residues (indicated by dots in Table 4A) that are critical for determining the differential DNA binding specificity of these receptors (Mader, S., V. Kumar, H. de Verneuil, and P. Chambon, 1989. Three amino acids of the oestrogen receptor are essential to its ability to distinguish an oestrogen from a glucocorticoid-responsive element. *Nature* 338:271–274; Umesono, K., and R. M. Evans, 1989. Determinants of target gene specificity for steroid/thyroid hormone receptors. *Cell* 57:1139–46). The three Drosophila proteins DHR3, EcR, and E75A, as well as the vertebrate receptors hRARα, hTRβ, and the human vitamin D receptor (hVDR), all have identical amino acids at these three positions; thus, these proteins may all have similar DNA binding specificities, as has already been shown for hRARα and hTRβ (Umesono, K., V. Giguere, C. K. Glass, M. G. Rosenfeld, and R. M. Evans, 1988. Retinoic acid and thyroid hormone induce gene expression through a common responsive element. *Nature* 336:262–265).

The E-region is an ~225 amino acid domain that functions as a hormone-binding domain in vertebrate receptors. This domain has also been implicated in hormone dependent receptor dimerization (Kumar, V. and P. Chambon, 1988. The estrogen receptor binds tightly to its responsive element as a ligand-induced homodimer. *Cell* 55:145–156; Guiochon, M. A., H. Loosfelt, P. Lescop, S. Sar, M. Atger, A. M. Perrot, and E. Milgrom, 1989. Mechanisms of nuclear localization of the progesterone receptor: evidence for interaction between monomers. *Cell* 57:1147–1154), hormone dependent nuclear localization of the glucocorticoid receptor (Picard, D., and K. R. Yamamoto, 1987. Two signals mediate hormone-dependent nuclear localization of the glucocorticoid receptor. *EMBO J.* 6:3333–3340), and binding of the glucocorticoid receptor to the 90 kDa heat shock protein (Pratt, W. B., D. J. Jolly, D. V. Pratt, W. M. Hollenberg, V. Giguere, F. M. Cadepond, G. G. Schweizer, M. G. Catelli, R. M. Evans, and E. E. Baulieu, 1988. A region in the steroid binding domain determines formation of the non-DNA-binding, 9 S glucocorticoid receptor complex. *J. Biol. Chem.* 263:267–273). Table 4B shows an alignment of the E regions of the DHR3 and EcR proteins with those of other receptor homologues. The three relatively highly conserved stretches within this region noted in Experimental Example I are overlined; each contains a cluster of residues conserved in all or most of the receptor sequences. DHR3 and EcR show strong similarity to each other and to the other proteins in these stretches, and a lower similarity outside of them. The presence of this E-region homology establishes these proteins as bona fide members of the nuclear receptor family, in contrast to the Drosophila knirps (Nauber, U., M. J. Pankratz, A. Kienlin, E. Seifert, U. Klemm, and H. Jackle, 1988. Abdominal segmentation of the Drosophila embryo requires a hormone receptor-like protein encoded by the gap gene knirps. *Nature* 336:489–492), knirps-related (oro, A. E., E. S. Ong, J. S. Margolis, J. W. Posakony, M. McKeown, and R. M. Evans, 1988. The Drosophila gene knirps-related is a member of the steroid-receptor gene superfamily. *Nature* 336:493–496), and egon (Rothe, M., U. Nauber, and H. Jackle, 1989. Three hormone receptor-like Drosophila genes encode an identical DNA-binding finger. *EMBO J.* 8:3087–3094) proteins, which show C-region homology but no E-region homology. The E region in DHR3 is most similar to that of E75A, and the E region of EcR is most similar to that of hTRα, although the level of these similarities is lower than those found among E regions of many other receptors (Table 4C). Thus, DHR3 and EcR are not especially close homologues of any previously cloned receptors. Comparison of E-region sequences allows division of the nuclear receptors into subfamilies (Petkovich, M., N. J. Brand, A. Krust, and P. Chambon, 1987. A human retinoic acid receptor which belongs to the family of nuclear receptors. *Nature* 330:444–450), the members of any one subfamily being more related to each other than to those in other subfamilies. The DHR3 and EcR receptors fall into a subfamily with the E75A, E75B, hRARα, hTRβ, and hVDR receptors.

D. In Situ Labeling of the EcR and DHR3 Proteins with Antibodies Induced by Proteins Produced in *E. coli*

To determine the intracellular and tissue distribution of the EcR and DHR3 proteins in Drosophila, affinity-purified polyclonal antibodies directed against those proteins were produced in the following manner. The region of about 120 amino acid residues that is located between the conserved DNA-binding and hormone-binding domains of these proteins was used as the immunogen to produce antibodies against each protein. Thus, the coding sequences for amino acids 335–447 of the EcR protein and for amino acids 164–289 of the DHR3 protein (see Tables 2 and 3, respectively) were cloned into the appropriate pATH (Dieckmann, C., and A. Tzagaloff, 1985. *J. Biol. Chem.* 260:1513–1520) or pUR expression vectors, so as to fuse these coding sequences to those encoding *E. coli* β-galactosidase (βgal) or to *E. coli* tryptophan E protein (trpE), respectively.

The βgal fusion proteins were produced in *E. coli* by the addition of the IPTG inducer to exponential cultures, while the production of trpE fusion proteins were induced by dilution into tryptophan-free media and subsequent addition of indoleacetic acid. For EcR, the trpE fusion protein was used as an immunogen and the βgal fusion protein was used on immunoblots to test sera for immunoreactivity to the EcR portion of the fusions. For DHR3, the βgal fusion protein was injected, and sera were checked against the trpE fusion protein.

For immunization the appropriate fusion protein was prepared by electrophoresis in SDS-PAGE gels and visualized by staining in ice-cold 0.25 M KCl, after which the fusion protein band was cut out. Approximately 100 μg of fusion protein in 0.25 ml of gel slice was crushed by passing through successively smaller hypodermic needles, and mixed with 0.25 ml of a sterile saline solution and 0.5 ml of Freund's complete adjuvant. For each immunogen, two New Zealand White rabbits were injected at multiple intramuscular sites, and after one month, boosted at two-week intervals, omitting the Freund's adjuvant. While the βgal fusion proteins were subject to the above gel electrophoresis without prior purification, the trpE fusion proteins were first purified by the following method which takes advantage of their insolubility in vivo.

E. coli from a 2-liter culture of induced cells were washed, and the cell pellet was subjected to several freeze/thaw cycles. The cells were resuspended in 18 ml of 50 mM Tris HCl, pH 7.5, 0.5 mM EDTA, and 1.8 ml of 10 mg/ml lysozyme was added. After 15 minutes on ice, the cells were lysed by passing three times through a french pressure cell at 10,000 psi. The insoluble fraction was collected by centrifugation at 27,000×g for 15 minutes, and washed by resuspension, using a Dounce homogenizer, in ice-cold 50 mM Tris HCl, 0.5 mM EDTA, 0.3 M NaCl, followed by centrifugation as above. The washing step was repeated, and the final pellet dissolved in 10 ml of 4M urea, 2% (w/v) SDS, 50 mM Tris HCl, pH 7.5, 1 mM EDTA, 5% (v/v) 2-mercaptoethanol. Material remaining insoluble was centrifuged out and discarded.

The antisera were affinity purified in a two-step procedure by successively passing the antibodies through "nonspecific" and "specific" affinity columns. In the case of antibodies raised against the trpE fusion proteins, the nonspecific column consisted of resin coupled to the insoluble protein derived from E. coli expressing unmodified trpE protein, and was used to remove antibodies directed against trpE epitopes, as well as against insoluble E. coli protein impurities. The specific column consisted of resin coupled to the EcR-trpE fusion protein (purified as described above) and was used to absorb the desired antibodies directed against the EcR epitopes, antibodies that were subsequently released from the column. In the case of antibodies raised against the βgal fusion proteins, the same general procedure was used, except that the resin in the nonspecific column was coupled to β-galactosidase, while that in the specific column was coupled to the DHR3-βgal fusion protein. Western blot analysis of the appropriate E. coli extracts demonstrated that these affinity-purified antibodies exhibited the desired specificity.

The intracellular distribution of the EcR protein in late third instar salivary glands was examined by in situ labeling of this protein with the anti-EcR antibody. The EcR protein was thereby shown to be highly localized in the nuclei of these glands. Indeed, when the polytene chromosomes in these nuclei were examined by the antibody-labeling method of Zink and Paro (Zinc, B., and R. Paro, 1989. *Nature* 337:468–471), specific loci within these chromosomes exhibited strong binding of the EcR protein. In particular, the EcR protein was bound to the early puff loci, including those occupied by the E75 and E74 genes. This is the result expected if the ecdysone receptor encoded by the EcR gene is that which induces the transcription of the early genes, as anticipated by the Ashburner model. Another prediction of the Ashburner model is that the ecdysone-receptor complex initially represses the genes responsible for the later puff, so that the transcription of the late genes induced by the early gene proteins is delayed until these proteins accumulate sufficiently to overcome this initial repression. If the EcR receptor is involved in this postulated initial repression, then one would expect the EcR protein to bind to the late puff loci in the salivary glands. This expectation was met by the observation that EcR protein also binds to the late puff loci in the polytene chromosomes.

Additional in situ antibody labeling experiments demonstrated that the EcR protein is present in the nuclei of all ecdysone target tissues examined in late third instar larvae. It is also present in most, if not all, cells during embryogenesis and other stages of Drosophila development that have been examined. In this respect, the EcR protein was not detected by anti-EcR antibody labeling of embryos in which the EcR gene was eliminated by a chromosomal deletion, further demonstrating the specificity of this antibody.

In contrast to the widespread distribution of the EcR protein, anti-DHR3 antibody labeling of embryos demonstrated that the distribution of the DHR3 protein is highly restricted during this stage of development. During the brief embryonic period of expression, the protein is restricted to the peripheral nervous system, and to cells surrounding the spiracles at the posterior end of the embryo.

Finally, it should be noted that affinity-purified antibodies against the E75A protein have also been prepared by the same technique described above for anti-EcR and anti-DHR3 antibodies. In situ antibody labeling of the E75A protein in larval salivary glands has also demonstrated that this protein is localized in the nucleus and is bound to specific loci in the polytene chromosomes.

EXAMPLE III

The Ecdysteroid-Binding, DNA-Binding and Genetic Regulatory Properties of the EcR Protein Demonstrate that it is an Edysone Receptor.

The following experiments demonstrate that the protein encoded by the EcR gene is an ecdysone receptor by the following three criteria. (1) The EcR protein binds ecdysteroids and accounts for a large proportion, if not all, of the ecdysteroid-binding activity present in Drosophila embryos and in a variety of cultured Drosophila cells. (2) The EcR protein binds with high specificity to a DNA sequence that functions as an ecdysone response element (EcRE), i.e., an enhancer that confers ecdysone inducibility to a promoter. (3) Cells that do not respond to ecdysone because they lack functional ecdysone receptors are transformed to the ecdysone-responsive state by transfection, with an EcR expression plasmid.

A. The EcR Protein Binds Ecdysteroids

The EcR expression plasmid, pMTEcR, shown in FIG. 1 contains the open reading frame encoding the EcR protein (EcR ORF; see Experimental Example II) fused to the Drosophila metallothionine promoter ($P_{MT}$) at its 5' end, and the polyadenylation-cleavage sequences of the Drosophila Actin 5C gene at its 3' end. Because transcription of the EcR ORF is under control of this metallothionine, that transcription is induced by $Cu^{2+}$ ion to yield an mRNA that, in turn, yields the EcR protein. A cell line, MtEcRHy, that overproduces this protein upon $CU^{2+}$induction, as determined by Western blot analysis using the affinity-purified anti-EcR antibody (see Experimental Example II), was constructed by the stable integration of the pMTEcR plasmid DNA into the genome of Drosophila Sch-2 cell line. A control cell line, MtHy, was similarly constructed by the integration of the expression vector DNA lacking the EcR ORF.

Whole cell extracts were prepared from both the MtEcRHy and MtHy cell lines after $Cu^{2+}$induction, and were assayed for ecdysteroid-binding activity using the high affinity ecdysone analogue [$^{125}$I] iodoponasterone A. The MtEcRHy extract contained sevenfold more saturable ecdysteroid-binding activity than the MtHy control extract.

To see if the induced ecdysteroid-binding activity was due to the EcR polypeptide itself, the EcR protein was depleted from the MtEcRHy extract by immunoprecipitation using an affinity-purified anti-EcR polyclonal antibody, or, as a control, the extract was mock-depleted with preimmune serum. The treated extracts were then assayed for ecdysteroid-binding activity. Comparison of the immuno-depleted extract with the mock-depleted extract showed that most of the binding activity was removed by the anti-EcR antibody treatment, indicating that the induced ecdysteroid-binding activity results from the EcR protein.

The endogenous ecdysteroid-binding activity in the control cell line, MtHy, was unchanged by $Cu^{2+}$ exposure, and was approximately the same as that in the Sch-2 cell from which it derives. The question arises as to whether the endogenous activity in these and other Drosophila cell lines, as well as in embryonic extracts, results from the expression of the EcR gene in their respective genomes. To answer this question, extracts from embryos and several cell lines were immuno-depleted and mock-depleted, as described above, and assayed for ecdysteroid-binding activity. Again, comparison of these treated extracts showed that the large majority of the endogenous binding activity was removed in each case by treatment with the anti-EcR antibody. Thus, it appears that most, if not all, of the endogenous binding activity in embryos and cell lines results form the resident EcR gene.

Methods
Extracts

Tissue culture cell extracts for hormone and DNA-binding experiments were prepared as follows. Cells were grown in spinner flasks to a density of $5-7\times10^6$ cells/ml, and were washed once in EcR buffer (25 mM Hepes, pH 7.0, 40 mM KCl, 10% (v/v) glycerol, 1 mM EDTA, 1 mM dithiothreitol, and the following cocktail of protease inhibitors: 10 mM $Na_2S_2O_5$, 500 µM PMSF, 1 µM leupeptin, 1 µM pepstatin). All further manipulations were at 4° C. Cells were resuspended in EcR buffer at 2% of the original culture volume, divided into 3 ml aliquots, and sonicated using 30 ½ second pulses with a probe sonicator (Bronson Sonifier 450), resulting in disruptions of ~95% of the cells. After centrifugation at 100,000×g for 1 hour, 100 µl aliquots of supernatant were frozen in liquid nitrogen, and stored at -80° C. Protein concentration was determined using bone serum albumin as the standard, and was typically 6-11 mg/ml. Embryo extracts were prepared by a similar protocol: 3-6 hour Canton S embryos were dechorionated in 55% commercial bleach for 2 minutes, washed extensively in 0.7% NaCl, and resuspended using 2 grams of embryos per ml of EcR buffer. Embryos were broken with 20 strokes in a Dounce homogenizer using a B pestle, and lysis was completed with the probe sonicator using the same settings as used for the tissue culture cells. The extract was adjusted to 400 mM KCl, centrifuged 1 hour at 100,000×g, and aliquots of supernatant were frozen. This extract contained 13.4 mg/ml protein. Before use in hormone binding, it was diluted tenfold in EcR buffer lacking KCl to bring the final KCl concentration to 40 mM.

Hormone-binding assays

For hormone-binding experiments, extracts were first diluted to the following concentrations in EcR buffer: 0.9 mg/ml for MtHy and MtEcRHy extracts, 3 mg/ml for S2 and SRS 1.5 extracts, 4 mg/ml for the Kc cell extracts, and 1.3 mg/ml for the embryo extract. All manipulations were done on duplicate samples in order to quantify variability in the results. For immunoprecipitation experiments, extracts were immuno-depleted, mock-depleted, or left untreated. For depletions, 300 µl of diluted extract was incubated for 30 minutes at 25° C. with 3.5 µl affinity-purified anti-EcR antibody, or with 3.5 µl preimmune serum for the mock-depletion control. Then 38 µl 10% Staphylococcus aureus (Pansorbin, Calbiochem) in EcR buffer was added, and incubation was continued for 15 minutes at 25° C. After centrifugation for 3 minutes in a microcentrifuge, the supernatant (depleted extract) was recovered. The immunoprecipitation was repeated, except in the case of the embryo extract which was subjected to only one round of precipitation. The "untreated" extract aliquots were left at 4° C. for the duration of the depletion procedure, and were diluted with EcR buffer to match the final concentration of the depleted aliquots.

The [$^{125}$I] iodoponasterone was supplied by P. Cherbas, and a modification of his hormone-binding assay was used (Cherbas, P. 1988. *Proc. Nat'l Acad. Sci., U.S.A.* 85:2096-2100). Assay tubes contained 140 µl extract, 14 µl [$^{125}$I] iodoponasterone, and either 14 µl EcR buffer or 14 µl unlabelled 20-OH ecdysone in EcR buffer as a competitor. [$^{125}$I] iodoponasterone was 2177 Ci/mM and was used at a final concentration of $5\times10^{-10}$ M in the assay; 20-OH ecdysone was $2\times10^{-5}$ M final concentration in the assay. After incubation for 1 hour at 25° C., each reaction was spotted on a dry Whatman GF/C filter (2.4 cm), and after 30 seconds the filter was washed by using a vacuum to draw 10 ml EcR buffer through the filter over a period of 1 minute. Filters were placed in 800 µl 4% SDS, and radioactivity was measured in a γ counter. The hormone-binding activities shown are saturable binding activities, calculated as the total binding activity, as measured in assays with no added competitor, minus the unsaturable binding activity, measured in the assays with excess unlabelled ecdysone added. In the most active extracts, the unsaturable activity (representing the large number of low affinity binding sites in the extract) was less than 10% of the total activity.

B. Genetic Regulatory Activity of the EcR Protein in vivo

An ecdysone-inducible reporter plasmid, pEcRE/Adh/βgal (FIG. 2), was constructed to test the regulatory functions of the EcR protein in vivo. The reporter gene in this plasmid consists of the sequence that encodes the *E. coli* β-galactosidase (βgal ORF) linked through the 5' leader sequence of the Drosophila Ultrabithorax gene (UBX leader and AUG) to an ecdysone-inducible promoter. This promoter was created by fusing a truncated version of the proximal promoter for the Drosophila Adh gene ($P_{DAdh-34+53}$, the numbers indicating that it consists of the sequence from base pair positions −34 to +53, which just includes the TATA box) to seven repeats of a 34 bp synthetic oligonucleotide (7 EcRE OLIGOS) which contains the ecdysone response element (EcRE) from the ecdysone-inducible heat shock gene hsp 27 (Riddihough and Pelham, 1987. *EMBO J.* 6:3729-3734). The seven EcREs should confer ecdysone-inducibility to the truncated promoter, provided that the cells transfected with this reporter plasmid contain the appropriate ecdysone receptor.

This ecdysone-inducible reporter plasmid was constructed by insertion of the 7 EcRE OLIGOS into plasmid pAdh/βgal, which is identical to pEcRE/Adh/βgal except that it lacks the array of ecdysone response elements. The pAdh/βgal plasmid should therefore not be ecdysone inducible and can serve as a control. To test these expectations, Sch-2 cultured cells (which were shown above to contain endogenous ecdysone-binding activity) were transfected with each plasmid and examined for β-galactosidase activity in the presence and absence of ecdysone. The ecdysone-induced β-galactosidase activity in the pEcRE/Adh/βgal transfected cells was 2000-fold greater than when such cells were not exposed to ecdysone, whereas ecdysone had little effect on the pAdh/βgal transfected cells. These results indicate that the EcREs confer ecdysone-inducibility on the $P_{DAdh-34+53}$ promoter, as expected, and that the Sch-2 cells contain functional ecdysone receptors.

To test the function of the EcR receptor in such a system, host cells lacking functional ecdysone receptors are required. "Ecdysone-resistant" cells lacking ecdysone-binding activity, and hence, presumably, functional receptors can be produced by continuously exposing ecdysone-responsive cells to ecdysone during a period of several weeks. This ecdysone-resistant state is then maintained in ecdysone-free media for several months. An ecdysone-resistant cell line, SRS 1.5, was therefore generated by growing Sch-2 cells in $5 \times 10^{-6}$ M ecdysone. The SRS 1.5 cells lack significant ecdysone-binding activity.

When these cells were transfected with the pEcRE/Adh/βgal plasmid and subsequently exposed to ecdysone, very little ecdysone-induced β-galactosidase activity was observed, indicating that the cells have only trace amounts, if any, of functional receptors. To test whether the expression of the EcR gene can "rescue" this deficiency, the SRS 1.5 cells were cotransfected with two plasmids: the ecdysone-inducible reporter plasmid, PEcRE/Adh/βgal, and a constitutive expression plasmid for the EcR gene, pActEcR, in which transcription of the EcR ORF is controlled by the Drosophil Actin 5c promoter, $P_{Act5C}$ (FIG. 3). Cotransfection with these two plasmids, followed by exposure to ecdysone, resulted in a dramatic induction of β-galactosidase activity. Thus, introduction of this EcR expression plasmid into the SRS 1.5 cells regenerated the ecdysone-inducibility they had lost.

Methods

Construction of the pAdh/βgal, pEcRE/Adh/βgal and pActEcR plasmids

Plasmid pAdh/βgal was constructed in two steps. The BglII-ScaI fragment of pDΔ5'-34, containing nucleotides −34 to +53 of the Drosophila Adh distal promoter, was cloned into pUC18 cut with ScaI and BamHI. The resulting plasmid was cut with EcoR1, and the EcoR1 fragment of cPβbxd6.2 (containing the Ubx untranslated leader and AUG, the βgal open reading frame, and the SV40 splice and poly A signals) inserted.

To construct pEcRE/Adh/βgal from pAdh/βgal, two 34-residue oligonucleotides were synthesized:

5'TCGAGAGACAAGGGTTCAATGCACTTGTCCAATG3'
3'CTCTGTTCCCAAGTTACGTGAACAGGTTACAGCT5'.

These will anneal to form 30 bp duplexes with Sal1 compatible four nucleotide overhangs at their 5' ends, as shown. Further annealing via the 5' overhangs allows formation of tandem arrays that can be inserted into pAdh/βgal at its SalI site just upstream from the TATA box of the truncated Adh promoter. When these ol igonucleotides were kinased, annealed, ligated into SalI-cut pAdh/βgal and cloned, pEcRE/Adh/βgal was obtained. Restriction mapping showed that it contained a tandem array of seven 34 bp repeats, each of which contains the 23 bp ecdysone response element (EcRE) present in the hsp 27 gene, the remaining 11 bp representing flanking hsp 2.7 sequences and the 5' overhangs.

The constitutive EcR expression plasmid, pActEcR, was formed by inserting the Fsp1-HpaI fragment of an EcR cDNA containing bp 851–4123 that contains the ORF encoding the EcR protein (Table 2), into the EcoRV site of the ActSV40BS plasmid. This expression vector was constructed in two steps by inserting the XbaI-EcoR1 fragment of cosPneoβ-gal, containing the SV40 splice and poly A signals, into BlueScript+KS (Stratagene) cut with SacII and Xba1, blunting the EcoR1 and SacII ends. The resulting plasmid was digested with BamH1 and ApaI, and the BamH1-EcoR1 fragment of pPAc was inserted, with the ApaI and EcoR1 ends being blunted.

Transfection and generation of the cell line SRS 1.5

The cell line SRS 1.5 was obtained by growing Schneider line 2 (Sch-2) cells in the presence of $2 \times 10^{-6}$ M 20-OH ecdysone (Sigma). This treatment initially halts growth of Sch-2 cells, but after several weeks the adapted cells grow well. SRS 1.5 cells were washed in hormone-free medium and passed several times in hormone-free medium prior to their use in transfection experiments. Cells were transfected by the calcium phosphate technique. Cells were transfected with 10 µg of each plasmid used; when only a single plasmid was being transfected, 10 µg of pUC18 DNA was added as a carrier. In general, all transfections were carried out in duplicate. Twenty-four hours after transfection, cells that were to undergo hormone treatment were split into two dishes, one of which was treated with $2 \times 10^{-6}$ M 20-OH ecdysone.

β-galactosidase assays

Forty-eight hours after transfection, 2 ml of cells were washed once in PBS (137 mM NaCl, 27 mM KCl, 65 mM $Na_2HPO_4$, 15 mM $KH_2PO_4$, pH 6.8), and were resuspended in 50 µl of 0.25 M sucrose, 10 mM Tris, pH 7.4, 10 mM EDTA, and repeatedly frozen in liquid nitrogen and thawed in a 37° C. water bath for a total of 3 freeze/thaw cycles. Cell debris was removed by a 10-minute centrifugation in a microcentrifuge at 4° C. The concentration of protein in the supernatant (cell extract) was determined by the Bradford method, with bovine serum albumin as a standard, and was typically 1.5–2.5 mg/ml. Extracts were assayed immediately or frozen and assayed up to two weeks later with no loss in activity. To 10 µl of extract, or an appropriate dilution, 500 µl of assay buffer was added (0.6 mM 4-methylumbelliferyl-β-D-galactoside, 60 mM $Na_2HPO_4$, 40 mM $NaH_2PO_4$, 10 mM KCl, 1.0 mM $MgSO_4$, pH 7.0). After a 30-minute incubation at 37° C., reactions were stopped with 500 µl of 300 mM glycine, 15 mM EDTA, pH 11.2. The fluorescent reaction product was quantified on a Perkin-Elmer LS-5B luminescence spectrometer, with $\lambda_{ex}=365$ nm and $\lambda_{em}=450$ nm. βgal activities are given as fluorescence units per µg protein assayed.

C. Specific Binding of the EcR Protein to Ecdysone Response Elements

The simplest explanation of the results described in the preceding section is that the EcR protein generated by the EcR expression plasmid binds to the EcRE of the reporter plasmid and, in combination with ecdysone, activates the minimal Adh promoter in that plasmid. The following experiment was designed to test whether the EcR protein exhibits specific binding to this EcRE in vitro.

Two plasmids were used: pUC18, which serves as the control, and pUC18-EcRE, which was-generated by substituting the HindII-XbaI fragment from pEcRE/Adh/βgal that contains the seven repeats of the 34 bp EcRE oligonucleotide, for the HindII-XbaI fragment of pUC18. Because the only difference between these two fragments is the seven oligonucleotide repeats, this is also the only difference between the two plasmids.

The two plasmids were digested with ApaLI and Hind III, $^{32}$p end labeled and mixed with an extract from MtEcRHy cells in which the EcR protein was overexpressed by $Cu^{2+}$ induction (see section A, above). After a 15-minute incubation at 25° C. to allow EcR-DNA binding to occur, affinity-purified anti-EcR antibody was added. The 25° C. incubation was continued for an additional 40 minutes, at which time anti-rabbit Ig-coated magnetic beads (Dupont Magnasort-R) were added, and the incubation continued 15 minutes more. The beads were separated from the solution magnetically, similarly washed, and the DNA eluted from the beads in 1% SDS at 65° C. The eluted DNA was ethanol precipitated and fractionated by electrophoresis in an agarose gel, which was dried and autoradiographed.

Only the fragment containing the EcRE oligonucleotide was specifically and efficiently registered on the autoradiographs, and that registration was dependent upon the anti-EcR antibody. Quantitative analysis of the autoradiographs demonstrated a $10^3$-fold preference for binding to the EcRE oligonucleotide over the average vector sequences, under the conditions of this assay (see Methods, below).

According to the criteria stated at the beginning of this Experimental Example, the EcR protein clearly satisfies the definition of an ecdysone receptor.

Methods

Conditions for the DNA binding assay

A quantity of 0.2 fmole of digested, labelled plasmid DNA was mixed with 2 µg (dI/dC) in 10 µl of TE (10 mM Tris HCl, pH 8.0, 1 mM EDTA), and 90 µl of the MtEcRHy extract, diluted to 0.9 mg/ml in EcR buffer adjusted to 180 mM KCl, was added. After binding for 15 minutes at 25° C., 2 ml of affinity-purified anti-EcR antibody, diluted 1.5x in EcR, was added, and this incubation was continued at 25° C. for 40 minutes, when 50 µl of anti-rabbit Ig-coated magnetic beads (Dupont Magnasort-R), exchanged into 180 mM KCl EcR buffer, was added and the incubation continued for 15 minutes.

The beads were washed twice in 400 µl 180 mM KCl EcR buffer, and DNA was eluted from the beads by soaking twice in 200 µl 1% SDS in TE at 65° C. The eluted DNA was ethanol precipitated and run on an agarose gel, which was dried and autoradiographed. As controls, one half of the input DNA (0.1 fmole) was run on the gel for comparison, and the binding assay was carried out leaving out the antibody.

EXAMPLE IV

Receptor Gene Mutagenesis.

Mutations in the steroid receptor superfamily genes can alter their function in two ways. Most obviously, they alter the sequences encoding the receptor proteins and thus alter the receptor function. Alternatively, they can alter the expression of these genes—an alteration that can be at any level of that expression from transcription of the gene to the translation of its mRNA(s). Such mutations can change when the gene is expressed during development or change the tissue and cell distribution of that expression. Thus, they can profoundly change the course of development. Furthermore, these mutations provide information about the regulation of receptor gene expression, just as mutations that alter the structure of the receptors encoded by these genes provide information about the genes whose expression these receptor proteins control. In particular, mutations that alter receptor gene expression can lead to the identification of the proteins and other regulatory molecules that control that expression. Clearly, mutagenesis of insect steroid receptor superfamily genes provides an important avenue leading to an ability to interfere in a high specific manner with insect development and thus to control insect infestations deleterious to human health and agriculture.

We have carried out mutagenesis experiments for two Drosophila members of the steroid receptor superfamily genes, E75 and E74, that we have cloned and characterized with respect to their expression. In this experimental example, mutagenesis of the E75 gene is described.

A. Deletion Mutations

In Drosophila, genetic analysis for a given locus—in this case, the early puff locus at 75B that houses the E75 gene—generally depends upon the isolation of deletions of all or part of that locus. This is because such deletions greatly facilitate the subsequent isolation of point and other small mutations within the locus. By isolating mutations that are revertants to the neighboring dominant Wrinkled (W) mutations, we have isolated and molecularly mapped the boundaries within our chromosomal walk (see Experimental Example I) of two deletions, $W^{R4}$ and $W^{R10}$, generated by gamma ray mutagenesis, the preferred way of generating such large alterations of genomic structure. One of these, $W^{R10}$, extends distally from Wrinkled to cover the entire E75 gene; and the other, $W^{R4}$, extends to a point about 90 kb upstream of the 5' end of the 50 kb E75A transcription unit and does not include the E75 gene.

An F2 screen was then employed to screen for gamma ray-induced mutations mapping to the 200 kb distal region that is included in the $W^{R10}$ deletion but not the $W^{R4}$ deletion. This screen resulted in the isolation of five members of a single lethal complementation group that molecular mapping data demonstrate represents the E75 gene. The most useful of these five mutations is the $E75^{x48}$ mutation. Molecular mapping of this mutation demonstrated that it is a 105 kb region that includes all of the E75 gene. It is useful because it provides an extremely efficient method to screen for other E75 mutations, i.e., by screening for mutations that cannot complement this deletion mutation.

B. E75 Mutations Generated by Ethyl Methane Sulfonate

The chemical mutagen ethyl methane sulfonate, or EMS, was used for this screen, as it is the preferred method for generating point or small mutations. An F2 screen of 15,000 lines resulted in the isolation of 23 penetrant mutations within the 105 kb region of the $E75^{x48}$ deletion, all of which turned out to be alleles of E75. It appears that this 105 kb region was saturated by this screen in respect to lethal complementation groups, and hence, E75 appears to be the only lethal complementation group in this region. Adding the five E75 mutations described above, a total of 28 penetrant E75 alleles have thus been isolated, several of which are temperature-sensitive alleles.

Inter se complementation studies among these alleles and examination of their phenotypes reveal a complex complementation group—a complexity that probably results from the fact that the E75 gene contains two overlapping transcription units, a 50 kb E75A unit and a 20 kb E75B unit that occupies the 3' end of the E75A unit (see Experimental Example I and Table 1). These alleles can be roughly divided into two groups: (1) those that cause lethality in early development—during the latter part of embryogenesis or during early larval development, and (2) those that cause lethality late in development during the prepupal or pupal stages.

This division correlates with the stages when the E75A and E75B units are expressed. Thus, E75A transcription is associated with each of the six pulses of ecdysone, including those that mark the embryonic and early larval stages. By contrast, E75B mRNAs are not observed until the end of the last larval stage, being particularly abundant during the pupal stage. This correlation invites the speculation that the early lethal mutations affect the expression of the E75A unit and its E74A protein, and that the late lethal mutations specifically affect the expression of the E75B unit and its E75B protein. This proposition can be tested by detailed molecular mapping of these mutations and further examination of their phenotypes at the molecular level to determine the causes of lethality.

The mutants described here provide a foundation for the further genetic analysis of the E75 gene that will allow exploration of the requirements for appropriate E75 expression and function and will identify structural and functional domains of E75. Some of the future E75 studies will best be performed by its in vitro manipulation, followed by transformation of the constructs back into Drosophila. Finally, it will be desirable to identify interacting genetic loci—interactions that may occur at the level of regulation of E75 expression or at the level of interaction of the E75 proteins with those encoded by other genes. Such interactive genetic loci can be identified via the isolation of mutations that act as suppressors or enhancers of the E75 mutations.

Methods

Strains, markers and chromosomes

For this aspect of the invention, the following strains, markers and chromosomes were used. $Tu^2$ was described by Lindsley (Lindsley, 1973. *DIS* 50:21). All other strains and mutations are as described (Lindsley, and Grell, 1968. *Genetic Variation of Drosophila melanogaster*, Publication 627, Carnegie Institute of Washington, Washington, D.C.). ru h $W^{R4}$ $e^s$ ro ca was constructed by recombination between ru h $W^{R4}$ $sbd^2$ $Tu^2$ and st $sbd^2$ $e^s$ ro ca. The st in ri $p^{p\ sbd2}$ chromosome was constructed by recombination of st in ri $p^p$ with $sbd^2$, in order to allow marking of this chromosome over $W^{R4}$ and $W^{R10}$, and homozygosed by crossing to TM3, backcrossing to TM3, and mating of isogeneic sibling progeny. The homozygosed st $p^p$ e11 line was a kind gift of Ken Burtis. Matthew Scott provided $Antp^w$ and $ns^{Rc4}$. Allan Shearn provided the pupal lethals X19, g26, Q13B, 8m12, iX-14, 2612, m45, p4, q 30L, mz416, 13m115, 052 and wq49. All strains used to construct the strains described above and other strains were obtained from the Bowling Green and Caltech stock centers.

TM1, TM3 and TM6B (Lindsley, and Grell, 1968. *Genetic Variation of Drosophila melanogaster*, Publication 627, Carnegie Institute of Washington, Washington, D.C.) are balancer chromosomes carrying recessive lethal mutations along with multiple inversions to suppress recombination. This allows the maintenance, as a heterozygote, of a recessive lethal chromosome in its original state. These chromosomes are also marked with convenient visible markers.

Quantitative Southern blot mapping for detection of mutant lesions

DNA was prepared from adult flies (about 50) by douncing in 1 ml of 10 mM Tris HCl, pH 7.5, 60 mM NaCl, 10 mM EDTA, 0.15 mM spermine, 0.2 mg/ml proteinase K. The homogenate was added to an equal volume of 0.2 M Tris HCl, pH 9.0, 30 mM EDTA, 2% SDS, 0.2 mg/ml proteinase K, incubated at 37° C. for 1 hour, and then extracted twice with buffer-saturated phenol and once with 24:1 chloroform/isoamyl alcohol. DNA was EtOH precipitated twice, hooking the pellet out without centrifugation. Southern blot hybridization was as described (Segraves, W. et al., 1984. *J. Mol. Biol.* 175:1–17). Where restriction fragment length polymorphism was not used in order to distinguish the parental chromosome from the balancer chromosome, quantitation of band intensity on genomic Southerns was achieved using a scanning densitometer. By using a control probe outside the mutant region, the amount of DNA in each track was internally controlled. Comparison of deficiency heterozygote to wild type bands, when normalized to a control band in this way, gives little deviation from the expected 1:2 ratio.

Molecular cloning of mutant lesions

Restriction fragments of the appropriate size were isolated by preparative low melting agarose (FMC) electrophoresis of about 20 μg of restricted genomic DNA. The 6 kb $W^{R4}$ XhO I fragment was cloned into Xho I-cleaved λSE6ΔBam which is propagated as a plasmid in order to grow the vector and cannot be packaged without an insert. The 18 kb $W^{R10}$ SalI fragment was cloned into the SalI site of λEMBL3, cleaved also with EcoRI for the biochemical selection method of prevention of propagation of non-recombinant clones. The 7 kb EcoRI fragment containing the x37 breakpoint was cloned into EcoRI-cleaved A λ607. Plating of recombinants on the hflA strain RY1073 prevented plaque formation by non-recombinant phage. The 14 kb x48 EcoRI fragment was cloned into the EcoRI site of λEMBL4, which had been cleaved with BamHI to utilize the "biochemical selection" for recombinants. The breakpoint fragments of x44 and the recipient fragment were cloned into λSE6ΔBam. Libraries were packaged using λin vitro packaging extracts prepared as described in Hohn (Hohn, 1979. *Methods Enzymol.* 68:299–303). After demonstration that each of the libraries gave a significant number of plaques only when inserts were included in the ligation, they were screened using restriction fragments capable of detecting the breakpoint clones.

Gamma ray mutagenesis

Adult males of the strain ru h W $sbd^2$ $Tu^2$ or st in ri $p^p$ $sbd^2$ were irradiated in plastic vials with 5000 rad of gamma rays from a $Cs^{137}$ source at a dose rate of 4300 rad/minute. These were then mated to virgins of the appropriate strain which were allowed to lay eggs for five days.

EMS mutagenesis

The primary lesion in EMS-induced mutations of bacteria and yeast is an alkylation-induced transition of guanine to adenine; most EMS-induced point mutations in Drosophila can similarly be explained on this basis. This change would be expected to convert, on the complementary strand, a C in the opa repeat element to a T, creating an in-frame stop codon (CAGCAA to UAGCAA or CAGUAA). (Ethylnitrosourea, ENU, which has been reported to yield a higher number of mutations for a given amount of sterility, is also an alkylator; however, considerably more stringent precautions must be taken in handling this mutagen.)

EMS was administered at 0.025 M to unstarved 1.5–5 day-old males in 1% sucrose solution (1.5 ml on two slips of Whatman #2 in a 350 ml milk bottle). Starvation of the males for 8 hours before EMS administration resulted in unacceptable levels of sterility, and males of the st $p^p$ $e^{11}$ strain readily fed upon the EMS/sucrose solution without starvation. Mutagenesis was monitored by crossing mutagenized males to attached-X FMA3 females. Other mutants seen in this screen included a large number of .Ca alleles (many mosaic) seen over TM6B in the F1 and F2 generations, a dominant brown allele, and two new mutants, Wink, a third chromosome dominant mutation resembling Bar, and a third chromosome dominant Curly-like mutation. Wink is easily scored (RK1), has complete penetrance, and is quite healthy over TM6B.

In the initial screen, vials were scored as mutant if they had fewer than 25% as many deficiency heterozygote as balancer heterozygote flies. On retesting, this was revised to 50% of the level seen in control crosses. Balancer heterozygotes were approximately two thirds as viable as deficiency heterozygotes.

In situ hybridization and cytological analysis

In situ hybridization of polytene chromosomes was carried out as described in Experimental Example I (see Methods, section A). Cytological analysis was performed by squashing larval salivary glands in lactoacetic orcein (2% orcein, 50% acetic acid, 30% lactic acid).

Although the present invention has been described in some detail by way of illustration and example for purposes of clarity of understanding, it will be obvious that certain changes and modifications may be practiced within the scope of the claims.

We claim:

1. An isolated polynucleotide encoding a Drosophila ecdysone receptor having the 878 amino acid predicted amino acid sequence of FIG. 4 (A–C) and which has ecdysteroid-binding activity wherein said ecdysone receptor exhibits saturable binding to β-ecdysone or ecdysone analogues.

2. An isolated polynucleotide according to claim 1, wherein the ecdysone analogue is [$^{125}$I] iodoponasterone A.

3. An isolated polynucleotide according to claim 1, wherein the polynucleotide comprises the nucleotide sequence from nucleotide 1069 to 3705 of FIG. 4 (A–C).

4. An isolated polynucleotide according to claim 1, wherein the polynucleotide consists of the 5534 bp cDNA sequence of the *Drosophila genomic* EcR gene.

5. A transformed insect bacterial or mammalian host cell comprising a polynucleotide encoding a *Drosophila ecdysone* receptor consistinq of the 878 amino acid predicted amino acid sequence of FIG. 4 (A–C) operably linked to a promoter, wherein said promoter is not naturally associated with an ecdysone receptor gene in the germline of naturally occurring Drosophila.

6. A transformed host cell according to claim 5, wherein the host cell is a bacterium and the promoter is a bacterial promoter.

7. A transformed host cell according to claim 5, wherein the polynucleotide is the EcR expression plasmid pMTEcR and the host cell is a Drosophila cell.

8. A transformed host cell according to claim 5, wherein the promoter is a *Drosophila metallothionine* promoter ($P_{MT}$) and the host cell is a Schneider line 2 (Sch-2) cell grown in 20-OH ecdysone.

* * * * *